US008846370B2

(12) United States Patent
Brown et al.

(10) Patent No.: US 8,846,370 B2
(45) Date of Patent: *Sep. 30, 2014

(54) GENETICALLY ENGINEERED MICROORGANISMS COMPRISING 4-HYDROXYBENZOYL-COA THIOESTERASES AND METHODS OF USING THE SAME FOR PRODUCING FREE FATTY ACIDS AND FATTY ACID DERIVATIVES

(75) Inventors: Robert Christopher Brown, San Diego, CA (US); Rekha Seshadri, San Diego, CA (US); Carlos Chavez-Torres, San Diego, CA (US); Weidong Xu, San Diego, CA (US); Toby Richardson, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,607

(22) Filed: Dec. 13, 2011

(65) Prior Publication Data

US 2012/0164713 A1 Jun. 28, 2012

Related U.S. Application Data

(60) Provisional application No. 61/426,568, filed on Dec. 23, 2010.

(51) Int. Cl.
*C12N 1/20* (2006.01)
*C12N 1/12* (2006.01)
*C12P 7/64* (2006.01)
*C12N 1/00* (2006.01)
*C12N 9/00* (2006.01)
*C07H 21/04* (2006.01)

(52) U.S. Cl.
USPC ............. 435/252.3; 435/257.2; 435/134; 435/243; 435/183; 536/23.2

(58) Field of Classification Search
None
See application file for complete search history.

(56) References Cited

U.S. PATENT DOCUMENTS

| | | | |
|---|---|---|---|
| 5,447,858 A | 9/1995 | Key et al. | 435/172.3 |
| 5,451,513 A | 9/1995 | Maliga et al. | 435/172.3 |
| 5,455,167 A | 10/1995 | Voelker et al. | 435/172.3 |
| 5,545,817 A | 8/1996 | McBride et al. | 800/205 |
| 5,545,818 A | 8/1996 | McBride et al. | 800/205 |
| 5,639,952 A | 6/1997 | Quail et al. | 800/205 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,851,796 A | 12/1998 | Schatz | 435/69.1 |
| 6,379,945 B1 | 4/2002 | Jepson et al. | 435/243 |
| 6,410,828 B1 | 6/2002 | Armstrong et al. | 800/287 |
| 7,135,290 B2 | 11/2006 | Dillon | 435/6 |
| 7,294,506 B2 | 11/2007 | Daniell et al. | 435/320.1 |
| 8,530,207 B2 * | 9/2013 | Watts et al. | 435/134 |
| 2008/0050774 A1 | 2/2008 | Berka et al. | 435/69.1 |
| 2010/0154293 A1 | 6/2010 | Hom et al. | 44/385 |

FOREIGN PATENT DOCUMENTS

| | | | |
|---|---|---|---|
| WO | WO 95/16783 | 6/1995 | C12N 15/82 |
| WO | WO 00/62601 | 10/2000 | A01H 13/00 |
| WO | WO 03/091413 | 11/2003 | |
| WO | WO 2005/005643 | 1/2005 | C12N 15/82 |
| WO | WO 2007/133558 | 11/2007 | E21B 37/00 |
| WO | WO 2007/136762 | 11/2007 | C12N 1/00 |
| WO | WO 2008/100251 | 8/2008 | C12N 9/00 |
| WO | WO 2010/019813 | 2/2010 | C12P 7/64 |

OTHER PUBLICATIONS

Zhuang et al. Kinetic, Raman, NMR, and site-directed mutagenesis studies of the *Pseudomonas* sp. strain CBS3 4-hydroxybenzoyl-CoA thioesterase active site, Biochemistry (2002), 41: 11152-11160.*
UniProt Accession No. A8FDR5, 4-hydroxybenzoyl-CoA thioesterase, created, Nov. 13, 2007.*
Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Seffernick et al. Melamine deaminase and atrazine chlorohydrolase: 98 percent identical but functionally different, J Bacteriol. Apr. 2001;183(8):2405-10.*
Witkowski et al. Biochemistry 1999, 38, 11643-11650.*
Abe, J., et al. (2008), "Expression of exogenous genes under the control of endogenous HSP70 and CAB promoters in the closterium peracerosum-strigosum-littorale complex", *Plant Cell Physiol*, 49(4): 625-632.
Altschul, S., et al. (1997), "Gapped BLAST and PSI-BLAST: a new generation of protein database search programs", *Nucleic Acids Research*, 25(17): 3389-3402.
Angermayr, A., et al. (2009), "Energy biotechnology with cyanobacteria", *Current Opinion in Biotechnology*, 20: 257-263.
Bateman, A., et al. (2000), "The pfam protein families database", *Nucleic Acids Research*, 28(1):263-266.
Bateman, A., et al. (2004), "The pfam protein families database", *Nucleic Acids Research*, 32: Database Issue: D138-D141.
Cantu, D., et al. (2010), "Thioesterases: A new perspective based on their primary and tertiary structures", *Protein Science*, 19:1281-1295.

(Continued)

*Primary Examiner* — Iqbal H Chowdhury
(74) *Attorney, Agent, or Firm* — Harness, Dickey & Pierce, P.L.C.

(57) ABSTRACT

The described invention provides genetically engineered microorganisms, including photosynthetic microorganisms, expressing 4-hydroxybenzoyl-CoA thioesterases and methods of using the genetically engineered microorganisms for producing free fatty acids and/or fatty acid derivatives.

19 Claims, 6 Drawing Sheets

(56) References Cited

OTHER PUBLICATIONS

Chan, D., et al. (2010), "Current understanding of fatty acid biosynthesis and the acyl carrier protein", *Biochem J*. 430:1-19.
Chae, J. et al. (2008), "Identification of genes coding for hydrolytic dehalogenation in the metagenome derived from a denitrifying 4-chlorobenzoate degrading consortium", *FEMS Microbiol Lett*, 281: 283-209.
Cork, D., et al. (1991), "Microbial transformations of herbicides and pesticides", *Advances in Applied Microbiology*, 36:1-66.
Dillon, S., et al. (2004), "The hotdog fold: wrapping up a superfamily of thioesterases and dehydratases" *BMC Bioinformatics*, 5:109.
Dunahay-Mariano, T., et al. (1994), "On the origins and functions of the enzymes of the 4-chlorobenzoate to 4-hydroxybenzoate converting pathway" *Biodegradation*, 5: 259-276.
Finn, R., et al. (2006), "Pfam: clans, web tools and services", *Nucleic Acids Research*, 34: Database Issue 34:D247-D251.
Finn, R., et al. (2010), "The pham protein families database", *Nucleic Acids Research*, 38: Database Issue 38:D211-D222.
Furukawa, K., et al. (1994), "Molecular genetics and evolutionary relationship of PCB-degrading bacteria", *Biodegradation*, 5:289-300.
Häggblom, M., et al. (1992), "Microbial breakdown of halogenated aromatic pesticides and related compounds", *FEMS Microbiology Reviews*, 9:29-72.
Hallmann, A., et al. (1997), "Gene replacement by homologous recombination in the multicellular green alga *volvox carteri*" *Proc. Natl. Acad. Sci* USA, 94:7469-7474.
Henikoff, S., et al. (1992), "Amino acid substitution matrices from protein blocks", *Proc. Natl. Acad. Sci* USA, 89:10915-10919.
Higson, F., (1992), "Microbial degradation of biphenyl and its derivatives", *Advances in Applied Microbiology*, 37:135-164.
Hileman, B., et al. (1993), "Concerns broaden over chlorine and chlorinated hydrocarbons", *Chemical & Engineering News*, 71:11-20.
International Search Report for PCT/US11/64641 dated Jun. 13, 2012.
Iwai, M., et al. (2004), "Improved genetic transformation of the thermophilic cyanobacterium, thermosynechoccus elongates BP-1", *Plant Cell Physiol*. 45(2):171-175.
Kindle, K., et al. (1989), "Stable nuclear transformation of *chlamydomonas* using the *chlamydomonas* gene for nitrate reductase", *The Journal of Cell Biology*, 109 (6, Part 1), 2589-2601.
Mayer, K., et al. (2005), "A structural model of the plant acyl-acyl carrier protein thioesterase fatB comprises two helix/4-stranded sheet domains, the N-terminal domain containing residues that affect specificity and the C-terminal domain containing catalytic residues" *The Journal of Biological Chemistry*, 280(5):3621-3627.
Mayer, K., et al. (2007), "Identification of amino acid residues involved in substrate specificity of plant acyl-ACP thioesterases using a bioinformatics-guided approach", *BMC Plant Biology*, 7: 1-11.
McBride, K., et al. (1994), "Controlled expression of plastid transgenes in plants based on a nuclear DNA-encoded and plastid-targeted T7 RNA polymerase" *Proc. Natl. Acad. Sci*. USA, 91:7301-7305.

Méndez-Alvarez, S., et al. (1994), "Transformation of *chlorobium limicola* by a plasmid that confers the ability to utilize thiosulfate" *Journal of Bacteriology*,176(23):7395-7397.
Ohnuma M., et al. (2008), "Polyethylene glycol (PEG)-mediated transient gene expression in a red alga, *cyanidioschyzon merolae* 10D", *Plant Cell Physiol*. 49(1):117-120.
Pearson W., et al. (1988), "Improved tools for biological sequence comparison" *Proc. Natl. Acad. Sci*. USA, 85:2444-2448.
Pearson, W., et al. (1994), "Using the FASTA program to search protein and DNA sequence databases", *Methods in Molecular Biology*, 24:307-331.
Perrone, C., et al. (1998), "the *chlamydomonas* IDA7 locus encodes a 140 kDa dynein intermediate chain required to assemble the I1 inner arm complex", *Molecular biology of the Cell*, 9:3351-3365.
Ramesh, V., et al. (2004), "A simple method for chloroplast transformation in *chlamydomonas reinhardtii*" *Methods in Molecular Biology*, 274:301-307.
Ravindran, C., et al. (2006), "Electroporation as a tool to transfer the plasmid pRL489 in *Oscillatoria* MKU 277" *Journal of Microbiological Methods*, 66:174-176.
Schweizer, E., et al. (2004), "Microbial Type I Fatty Acid Synthases (FAS): major players in a network of Cellular FAS systems", *Microbiology and molecular biology reviews* 68(3):501-517.
Schroda, M., et al. (2000), "The HSP70A promoter as a tool for improved expression of transgenes in *Chlamydomonas*", *The plant journal* 21(2):121-131.
Smith, T., et al, (1981), "Comparison of biosequences", *Advances in Applied Mathematics* 2:482-489.
Sonnhammer, E., et al. (1998), "Pfam: multiple sequence alignments and HMM-profiles of protein domains" *Nucleic Acids Research* 26(1):320-322.
Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.
Sun, Y., et al. (2006), "Functional complementation of a nitrate reductase defective mutant of a green alga *dunaliella* viridis by introducing the nitrate reductase gene", *Gene* 377:140-149.
Tan, C., et al. (2005), "Establishment of a micro-particle bombardment transformation system for *dunaliella saline*", *The Journal of Microbiology* 43:361-365.
Uniprot Accession No. B61T13, Dec. 16, 2008 [online]. [Retrieved on Jun. 6, 2012]. Retrieved from the internet <URL: http://www.uniprot.org/uniprot/BGITI3txt?version=11>.
Voelker, T., et al. (1994), "Alteration of the specificity and regulation of fatty acid synthesis of *Escherichia coli* by expression of a plant medium-chain acyl-acyl carrier protein thioesterase" *Journal of Bacteriology* 176(23):7320-7327.
Zhuang, Z., et al. (2003) "Characterization of the 4-hydroxybenzoyl-coenzyme a thioesterase from *arthrobacter* sp. strain SU", *Applied and Environmental Microbiology* 69(5):2707-2711.
International Preliminary Report on Patentability and Written Opinion dated Mar. 6, 2014 issued in PCT Application No. PCT/US2011/064641.

\* cited by examiner

SEQUENCE LISTING

```
<160> NUMBER OF SEQ ID NOS: 52

<210> SEQ ID NO 1
<211> LENGTH: 138
<212> TYPE: PRT
<213> ORGANISM: unknown
<220> FEATURE:
<223> OTHER INFORMATION: 4-hydroxybenzoyl-CoA thioesterase from
      unspecified microorganism

<400> SEQUENCE: 1

Met Tyr Val Ser Lys Lys Glu Ile Glu Val Arg Tyr Ala Glu Thr Asp
1               5                   10                  15

Gln Met Gly Val Val Tyr His Ala Asn Tyr Leu Ile Trp Met Glu Val
            20                  25                  30

Gly Arg Thr Ala Leu Ile Lys Glu Leu Gly Phe Ser Tyr Ala Glu Met
        35                  40                  45
```

```
Glu Lys Asp Gly Ile Leu Ser Pro Val Val Asp Ile Asn Val Arg Tyr
    50                  55                  60

Val Lys Pro Leu Arg Tyr Gly Glu Thr Ala Thr Val His Thr Trp Ile
65                  70                  75                  80

Glu Glu Tyr Asn Gly Phe Lys Thr Val Tyr Gly Tyr Glu Ile Phe Asn
                85                  90                  95

Ser Ala Ser Glu Thr Ala Val Lys Ala Thr Ser His Ile Cys Val
            100                 105                 110

Asp Gly Asn Ser Phe Lys Pro Val Gln Phe Arg Lys Leu Tyr Pro Lys
            115                 120                 125

Trp His Glu Ala Tyr Glu Glu Ala Lys Lys
    130                 135

<210> SEQ ID NO 2
<211> LENGTH: 152
<212> TYPE: PRT
<213> ORGANISM: unknown
<220> FEATURE:
<223> OTHER INFORMATION: 4-hydroxybenzoyl-CoA thioesterase from
      unspecified microorganism

<400> SEQUENCE: 2

Met Ser Gly Ser Ala Met Ala Pro Val Pro Ala Gln Gly Val Ile Arg
1               5                   10                  15

Asp Gly Val His Val Phe Pro Val Arg Ile Tyr Tyr Glu Asp Thr Asp
                20                  25                  30

Ala Gly Gly Ile Val Tyr His Ala Arg Tyr Leu His Phe Thr Glu Arg
            35                  40                  45

Ala Arg Ser Glu Leu Met Arg Leu Cys Gly Tyr Asp Asn Arg Asp Leu
    50                  55                  60

Met Lys Asp Pro Gly Ile Ala Phe Ala Val Arg Lys Ala Thr Cys Asp
65                  70                  75                  80

Phe Arg Arg Pro Ala Val Leu Asp Asp Leu Leu Glu Val His Thr Thr
                85                  90                  95

Val Gly Lys Val Gly Gly Ala Ser Phe Glu Ala Val His Glu Ile Lys
            100                 105                 110

Arg Asp Gly Glu Ile Leu Val Arg Ile Asp Ile Lys Leu Ala Ser Met
        115                 120                 125

Ala Leu Ala Gly Gly Val Ala Arg Leu Pro Asp Ala Val Lys His Arg
    130                 135                 140

Leu Ala Gly Leu Leu Ser Gly Asp
145                 150

<210> SEQ ID NO 3
<211> LENGTH: 417
<212> TYPE: DNA
<213> ORGANISM: unknown
<220> FEATURE:
<223> OTHER INFORMATION: Gene coding for 4-hydroxybenzoyl-CoA
      thioesterase from unspecified microorganism

<400> SEQUENCE: 3
ttgtacgtct caaaaaaaga aatagaagtc cgctatgccg aaacagatca aatgggcgtc      60
gtctatcacg ccaattattt gatttggatg gaggtaggac ggacggcttt aattaaagaa     120
ctcggcttct cttacgccga aatggagaaa gacggcatcc tgtcgcctgt cgtggatatc     180
aatgtccgct acgtcaaacc tcttcgctac ggtgaaaccg cgacggtaca tacgtggatt     240
```

| | |
|---|---|
| gaagaatata acggctttaa aacggtatat gggtatgaaa tcttcaattc cgctagtgaa | 300 |
| accgctgtga aggccacatc gtcccatatt tgcgttgacg ggaacagctt caaaccggtt | 360 |
| cagttccgca agctttatcc aaagtggcat gaagcttatg aagaggccaa aaagtaa | 417 |

<210> SEQ ID NO 4
<211> LENGTH: 459
<212> TYPE: DNA
<213> ORGANISM: unknown
<220> FEATURE:
<223> OTHER INFORMATION: Gene coding for 4-hydroxybenzoyl-CoA
      thioesterase from unspecified microorganism

<400> SEQUENCE: 4

| | |
|---|---|
| atgagcggaa gcgcgatggc cccggtgccg gcgcagggcg tgatccgcga cggcgtgcac | 60 |
| gtctttccgg tgcggatcta ttacgaggac accgacgccg gcggcatcgt ctaccacgcc | 120 |
| cgctatctgc actttacgga acgggcgcgg tcggagttga tgcgcctgtg cggctacgac | 180 |
| aaccgggacc tcatgaagga ccccggcatc gccttcgccg tgcgcaaggc gacctgtgac | 240 |
| ttccgccgcc cggcggtgct ggacgacctg ctggaggtcc acaccaccgt cggcaaggtg | 300 |
| ggcgcgccct cgttcgaggc ggtgcacgag atcaagcgcg acggggagat cctcgtgcgc | 360 |
| atcgacatca agctggccag catggcgctg gccggaggcg tggcgcgcct gccggatgcc | 420 |
| gtgaagcatc gcctggcggg gctgctgagc ggagactag | 459 |

<210> SEQ ID NO 5
<211> LENGTH: 4619
<212> TYPE: DNA
<213> ORGANISM: Artificial Sequence
<220> FEATURE:
<223> OTHER INFORMATION: bacterial/cyanobacterial expression/integration
      vector RB-RS1

<400> SEQUENCE: 5

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagccata ttcaacggga aacgtcttgc tcgaggccgc | 240 |
| gattaaattc caacatggat gctgatttat atgggtataa atgggctcgc gataatgtcg | 300 |
| ggcaatcagg tgcgacaatc tatcgattgt atgggaagcc cgatgcgcca gagttgtttc | 360 |
| tgaaacatgg caaaggtagc gttgccaatg atgttacaga tgagatggtc agactaaact | 420 |
| ggctgacgga atttatgcct cttccgacca tcaagcattt tatccgtact cctgatgatg | 480 |
| catggttact caccactgcg atccccggga aaacagcatt ccaggtatta gaagaatatc | 540 |
| ctgattcagg tgaaaatatt gttgatgcgc tggcagtgtt cctgcgccgg ttgcattcga | 600 |
| ttcctgtttg taattgtcct tttaacagcg atcgcgtatt tcgtctcgct caggcgcaat | 660 |
| cacgaatgaa taacggtttg gttgatgcga gtgattttga tgacgagcgt aatggctggc | 720 |
| ctgttgaaca agtctggaaa gaaatgcata agcttttgcc attctcaccg gattcagtcg | 780 |
| tcactcatgg tgatttctca cttgataacc ttatttttga cgaggggaaa ttaataggtt | 840 |
| gtattgatgt tggacgagtc ggaatcgcag accgatacca ggatcttgcc atcctatgga | 900 |
| actgcctcgg tgagttttct ccttcattac agaaacggct ttttcaaaaa tatggtattg | 960 |
| ataatcctga tatgaataaa ttgcagtttc atttgatgct cgatgagttt ttctaaccga | 1020 |
| tatggatggc accgatgcgg aatcccaaca gattgccttt gacaacaatg tggcctggaa | 1080 |

```
taacctgggg gatttgtcca ccaccaccca acgggcctac acttcggcta ttagcacaga    1140
cacagtgcag agtgtttatg gcgttaatct ggaaaaaaac gataacattc ccattgtttt    1200
tgcgtggccc attttttccca ccaccttaa tcccacagat tttcaggtaa tgcttaacac    1260
gggggaaatt gtcaccccgg tgatcgcctc tttgattccc aacagtgaat acaacgaacg    1320
gcaaacggta gtaattacgg gcaattttgg taatcgttta accccaggca cggagggagc    1380
gatttatccc gtttccgtag gcacagtgtt ggacagtact cctttggaaa tggtgggacc    1440
caacggcccg gtcagtgcgg tgggtattac cattgatagt ctcaaccccct acgtggccgg    1500 caatggtccc aaaattgtcg ccgctaagtt agaccgcttc agtgacctgg gggaaggggc    1560
tcccctctgg ttagccacca atcaaaataa cagtggcggg gatttatatg gagaccaagc    1620
ccaatttcgt ttgcgaattt acaccagcgc cggttttttcc cccgatggca ttgccagttt    1680
actacccaca gaatttgaac ggtattttca actccaagcg gaagatatta cgggacggac    1740
agttatccta acccaaactg gtgttgatta tgaaattccc ggctttggtc tggtgcaggt    1800
gttggggctg gcggatttgg ccgggggttca ggacagctat gacctgactt acatcgaaga    1860
tcatgacaac tattacgaca ttatcctcaa aggggacgaa gccgcagttc gccaaattaa    1920
gagggttgct ttgccctccg aaggggatta ttcggcggtt tataatcccg gtggccccgg    1980
caatgatcca gagaatggtc ccccactgtc agaccaagtt tactcatata tactttagat    2040
tgatttaaaa cttcatttt aatttaaaag gatctaggtg aagatccttt ttgataatct    2100
catgaccaaa atcccttaac gtgagttttc gttccactga gcgtcagacc ccgtagaaaa    2160
gatcaaagga tcttcttgag atcctttttt tctgcgcgta atctgctgct tgcaaacaaa    2220
aaaaccaccg ctaccagcgg tggtttgttt gccggatcaa gagctaccaa ctctttttcc    2280
gaaggtaact ggcttcagca gagcgcagat accaaatact gtccttctag tgtagccgta    2340
gttaggccac cacttcaaga actctgtagc accgcctaca tacctcgctc tgctaatcct    2400
gttaccagtg gctgctgcca gtggcgataa gtcgtgtctt accgggttgg actcaagacg    2460
atagttaccg gataaggcgc agcggtcggg ctgaacgggg ggttcgtgca cacagcccag    2520
cttggagcga acgacctaca ccgaactgag atacctacag cgtgagctat gagaaagcgc    2580
cacgcttccc gaagggagaa aggcggacag gtatccggta agcggcaggg tcggaacagg    2640
agagcgcacg agggagcttc caggggggaaa cgcctggtat ctttatagtc ctgtcgggtt    2700
tcgccacctc tgacttgagc gtcgattttt gtgatgctcg tcaggggggc ggagcctatg    2760
gaaaaacgcc agcaacgcgg cctttttacg gttcctggcc ttttgctggc cttttgctca    2820
catgttcttt cctgcgttat cccctgattc tgtggataac cgtattaccg cctttgagtg    2880
agctgatacc gctcgccgca gccgaacgac cgagcgcagc gagtcagtga gcgaggaagc    2940
ggaagagcgc ccaatacgca aaccgcctct ccccgcgcgt tggccgattc attaatgcag    3000
ctggcacgac aggtttcccg actggaaagc gggcagtgaa ttgctgaagc ggaatccctg    3060
gttaatgccg ccgccgatgc caattgcatt ctccaagtgg ggcacattga acgcttcaac    3120
ccggcatttt tagagctaac caaaattctc aaaacggaag agttattggc gatcgaagcc    3180
catcgcatga gtccctattc ccagcgggcc aatgatgtct ccgtggtatt ggatttgatg    3240
atccatgaca ttgacctgtt gctggaattg gtgggttcgg aagtggttaa actgtccgcc    3300
agtggcagtc gggcttctgg gtcaggatat ttgattatg tcaccgctac gttaggcttc    3360
tcctccggca ttgtggccac cctcaccgcc agtaaggtca cccatcgtaa aattcgttcc    3420
```

```
atcgccgccc actgcaaaaa ttccctcacc gaagcggatt ttctcaataa cgaaattttg    3480
atccatcgcc aaaccaccgc tgattggagc gcggactatg ccaggtatt gtatcgccag    3540 gatggtctaa tcgaaaaggt ttacaccagt aatattgaac ctctccacgc tgaattagaa    3600
cattttattc attgtgttag gggaggtgat caaccctcag tgggggggaga acaggccctc    3660 aaggccctga agttagccag tttaattgaa gaaatggccc tggacagtca ggaatggcat    3720
gggggggaag ttgtgacaga atatcaagat gccaccctgg ccctcagtgc gagtgtttaa    3780
atcaacttaa ttaatgcaat tattgcgagt tcaaactcga taactttgtg aaatattact    3840
gttgaattaa tctatgacta ttcaatacac ccccctagcc gatcgcctgt tggcctacct    3900
cgccgccgat cgcctaaatc tcagcgccaa gagtagttcc ctcaacacca gtattctgct    3960
cagcagtgac ctattcaatc aggaagggg aattgtaaca gccaactatg ctttgatgg     4020 ttatatgggc gcaacgcaat taatgtgagt tagctcactc attaggcacc ccaggcttta    4080
cactttatgc ttccggctcg tatgttgtgt ggaattgtga gcggataaca atttcacaca    4140
ggaaacagct atgaccatga ttacgccaag cttgcatgcc tgcaggtcga ctctagagga    4200
tccccgggta ccgagctcga attcactggc cgtcgtttta caacgtcgtg actgggaaaa    4260
ccctggcgtt acccaactta atcgccttgc agcacatccc cctttcgcca gctggcgtaa    4320
tagcgaagag gcccgcaccg atcgcccttc ccaacagttg cgcagcctga atggcgaatg    4380
gcgcctgatg cggtattttc tccttacgca tctgtgcggt atttcacacc gcatatggtg    4440
cactctcagt acaatctgct ctgatgccgc atagttaagc cagccccgac acccgccaac    4500
acccgctgac gcgccctgac gggcttgtct gctcccggca tccgcttaca gacaagctgt    4560
gaccgtctcc gggagctgca tgtgtcagag gttttcaccg tcatcaccga aacgcgcga     4619
```

<210> SEQ ID NO 6
<211> LENGTH: 138
<212> TYPE: PRT
<213> ORGANISM: Bacillus licheniformis ATCC 14580

<400> SEQUENCE: 6

Met Tyr Val Ser Lys Lys Glu Ile Glu Val Arg Tyr Ala Glu Thr Asp
1               5                   10                  15

Gln Met Gly Val Val Tyr His Ala Asn Tyr Leu Ile Trp Met Glu Val
            20                  25                  30

Gly Arg Thr Ala Leu Ile Lys Glu Leu Gly Phe Ser Tyr Ala Glu Met
        35                  40                  45

Glu Lys Asp Gly Ile Leu Ser Pro Val Asp Ile Asn Val Arg Tyr
    50                  55                  60

Val Lys Pro Leu Arg Tyr Gly Glu Thr Ala Thr Val His Thr Trp Ile
65                  70                  75                  80

Glu Asp Tyr Asn Gly Phe Lys Thr Val Tyr Gly Tyr Glu Ile Phe Asn
                85                  90                  95

Ser Ala Gly Glu Thr Ala Val Lys Gly Thr Ser His Ile Cys Val
            100                 105                 110

Asp Gly Asp Ser Phe Lys Pro Val Gln Phe Arg Lys Leu Tyr Pro Lys
        115                 120                 125

Trp His Glu Ala Tyr Glu Ala Lys Lys
    130                 135

<210> SEQ ID NO 7
<211> LENGTH: 138
<212> TYPE: PRT

<213> ORGANISM: Bacillus subtilis subsp. natto BEST195

<400> SEQUENCE: 7

```
Met His Val Ser Lys Lys Glu Ile Glu Val Arg Tyr Ala Glu Thr Asp
1               5                   10                  15

Gln Met Gly Ile Val Tyr His Ala Asn Tyr Leu Val Trp Met Glu Val
            20                  25                  30

Gly Arg Thr Ala Leu Ile Lys Asp Leu Gly Phe Leu Tyr Ser Asp Met
        35                  40                  45

Glu Lys Lys Gly Ile Leu Ser Pro Val Val Asp Ile Asn Ile Ser Tyr
50                  55                  60

Lys Lys Pro Leu His Tyr Gly Glu Thr Ala Val Val His Thr Trp Ile
65                  70                  75                  80

Glu Glu Tyr Asn Gly Phe Lys Thr Val Tyr Gly Tyr His Ile Tyr Asn
                85                  90                  95

Pro Ala Gly Glu Leu Ser Ile Lys Ala Thr Ser Ser His Ile Cys Val
            100                 105                 110

Asp Lys Glu Ser Phe Lys Pro Ile Gln Phe Arg Lys Ala Phe Pro Asp
        115                 120                 125

Trp His Thr Ser Tyr Glu Lys Ala Lys Lys
    130                 135
```

<210> SEQ ID NO 8
<211> LENGTH: 138
<212> TYPE: PRT
<213> ORGANISM: Bacillus subtilis

<400> SEQUENCE: 8

```
Met His Val Ser Lys Lys Glu Ile Glu Val Arg Tyr Ala Glu Thr Asp
1               5                   10                  15

Gln Met Gly Ile Val Tyr His Ala Asn Tyr Leu Val Trp Met Glu Val
            20                  25                  30

Gly Arg Thr Ala Leu Ile Lys Asp Leu Gly Phe Leu Tyr Ser Asp Met
        35                  40                  45

Glu Lys Lys Gly Val Leu Ser Pro Val Val Asp Ile Asn Ile Ser Tyr
50                  55                  60

Lys Lys Pro Leu His Tyr Gly Glu Thr Ala Val Val His Thr Trp Ile
65                  70                  75                  80

Glu Asp Tyr Asn Gly Phe Lys Thr Val Tyr Gly Tyr His Ile Tyr Asn
                85                  90                  95

Pro Ala Gly Glu Leu Ser Ile Lys Ala Thr Ser Ser His Ile Cys Val
            100                 105                 110

Asp Lys Glu Ser Phe Lys Pro Ile Gln Phe Arg Lys Ala Phe Pro Asp
        115                 120                 125

Trp His Thr Ala Tyr Glu Lys Ala Lys Lys
    130                 135
```

<210> SEQ ID NO 9
<211> LENGTH: 138
<212> TYPE: PRT
<213> ORGANISM: Bacillus subtilis subsp. spizizenii str. W23

<400> SEQUENCE: 9

```
Met His Val Ser Lys Lys Glu Ile Glu Val Arg Tyr Ala Glu Thr Asp
1               5                   10                  15

Gln Met Gly Ile Val Tyr His Ala Asn Tyr Leu Val Trp Met Glu Val
            20                  25                  30
```

```
Gly Arg Thr Ala Leu Ile Lys Asp Leu Gly Phe Leu Tyr Ser Asp Met
         35                  40                  45

Glu Lys Lys Gly Val Leu Ser Pro Val Val Asp Ile Asn Ile Ser Tyr
 50                  55                  60

Lys Lys Pro Leu His Tyr Gly Glu Thr Ala Val Val His Thr Trp Ile
 65                  70                  75                  80

Glu Glu Tyr Asn Gly Phe Lys Thr Ile Tyr Gly Tyr His Ile Tyr Asn
                 85                  90                  95

Pro Ala Gly Val Leu Ser Ile Glu Ala Thr Ser Ser His Ile Cys Val
                100                 105                 110

Asp Lys Glu Ser Phe Lys Pro Ile Gln Phe Arg Lys Ala Phe Pro Asp
            115                 120                 125

Trp His Glu Ala Tyr Glu Lys Ala Lys Lys
            130                 135

<210> SEQ ID NO 10
<211> LENGTH: 138
<212> TYPE: PRT
<213> ORGANISM: Bacillus amyloliquefaciens DSM7

<400> SEQUENCE: 10

Met His Val Ser Lys Lys Glu Ile Glu Val Arg Tyr Ala Glu Thr Asp
 1               5                  10                  15

Gln Met Gly Ile Val Tyr His Ala Asn Tyr Leu Val Trp Met Glu Val
                 20                  25                  30

Gly Arg Thr Ala Leu Ile Lys Asp Leu Gly Phe Leu Tyr Lys Asp Met
         35                  40                  45

Glu Glu Arg Gly Val Leu Ser Pro Val Val Asp Ile Ser Ile Ser Tyr
 50                  55                  60

Lys Lys Pro Leu Arg Tyr Gly Glu Thr Ala Val Val His Thr Trp Ile
 65                  70                  75                  80

Glu Glu Tyr Asn Gly Phe Lys Thr Val Tyr Gly Tyr His Ile Tyr Asn
                 85                  90                  95

Pro Asp Gln Glu Leu Ala Ile Glu Ala Thr Ser Ser His Ile Cys Val
                100                 105                 110

Asp Lys Gln Ser Phe Lys Pro Ile Gln Phe Arg Lys Ala Phe Pro Asp
            115                 120                 125

Trp His Ala Ala Tyr Glu Lys Ala Lys Lys
            130                 135

<210> SEQ ID NO 11
<211> LENGTH: 138
<212> TYPE: PRT
<213> ORGANISM: Bacillus amyloliquefaciens FZB42

<400> SEQUENCE: 11

Met His Val Ser Lys Lys Glu Ile Glu Val Arg Tyr Ala Glu Thr Asp
 1               5                  10                  15

Gln Met Gly Ile Val Tyr His Ala Asn Tyr Leu Val Trp Met Glu Val
                 20                  25                  30

Gly Arg Thr Ala Leu Ile Lys Glu Leu Gly Phe Leu Tyr Lys Asp Met
         35                  40                  45

Glu Asp Arg Gly Val Leu Ser Pro Val Leu Asp Ile Ser Ile Ser Tyr
 50                  55                  60

Lys Lys Pro Leu Arg Tyr Gly Glu Thr Ala Val Val His Thr Trp Ile
 65                  70                  75                  80
```

```
Glu Glu Ser Asn Gly Phe Lys Thr Val Tyr Gly Tyr His Ile Tyr Asn
                85                  90                  95

Pro Asp Gln Glu Leu Ala Ile Lys Ala Thr Ser Ser His Ile Cys Val
            100                 105                 110

Asp Lys Glu Ser Phe Lys Pro Ile Gln Phe Arg Lys Ala Phe Pro Asp
        115                 120                 125

Trp His Ala Ala Tyr Glu Lys Ala Lys Lys
    130                 135

<210> SEQ ID NO 12
<211> LENGTH: 121
<212> TYPE: PRT
<213> ORGANISM: Bacillus subtilis subsp. subtilis str. 168

<400> SEQUENCE: 12

Met Gly Ile Val Tyr His Ala Asn Tyr Leu Val Trp Met Glu Val Gly
1               5                   10                  15

Arg Thr Ala Leu Ile Lys Asp Leu Gly Phe Leu Tyr Ser Asp Met Glu
            20                  25                  30

Lys Lys Gly Val Leu Ser Pro Val Val Asp Ile Asn Ile Ser Tyr Lys
        35                  40                  45

Lys Pro Leu His Tyr Gly Glu Thr Ala Val Val His Thr Trp Ile Glu
    50                  55                  60

Asp Tyr Asn Gly Phe Lys Thr Val Tyr Gly Tyr His Ile Tyr Asn Pro
65                  70                  75                  80

Ala Gly Glu Leu Ser Ile Lys Ala Thr Ser Ser His Ile Cys Val Asp
                85                  90                  95

Lys Glu Ser Phe Lys Pro Ile Gln Phe Arg Lys Ala Phe Pro Asp Trp
            100                 105                 110

His Thr Ala Tyr Glu Lys Ala Lys Lys
        115                 120

<210> SEQ ID NO 13
<211> LENGTH: 138
<212> TYPE: PRT
<213> ORGANISM: Bacillus atrophaeus 1942

<400> SEQUENCE: 13

Met His Val Ser Lys Lys Glu Ile Glu Val Arg Tyr Ser Glu Thr Asp
1               5                   10                  15

Gln Met Gly Ile Val Tyr His Ala Asn Tyr Leu Val Trp Met Glu Val
            20                  25                  30

Gly Arg Thr Ala Leu Ile Lys Asp Leu Gly Phe Leu Tyr Ser Asp Met
        35                  40                  45

Glu Lys Lys Gly Val Leu Ser Pro Val Val Asp Ile Asn Ile Ser Tyr
    50                  55                  60

Lys Lys Pro Leu His Tyr Gly Glu Thr Ala Val Val His Thr Trp Ile
65                  70                  75                  80

Glu Glu Tyr Asn Gly Phe Lys Thr Val Tyr Gly Tyr His Ile Leu Asn
                85                  90                  95

Pro Glu Gly Asp Val Ser Ile Thr Ala Lys Ser Ser His Ile Cys Val
            100                 105                 110

Asp Lys Glu Ser Phe Lys Pro Ile Gln Phe Arg Lys Ala Phe Pro Asp
        115                 120                 125

Trp His Lys Ala Tyr Glu Lys Ala Lys Lys
    130                 135
```

<210> SEQ ID NO 14
<211> LENGTH: 140
<212> TYPE: PRT
<213> ORGANISM: Bacillus pumilus ATCC 7061

<400> SEQUENCE: 14

Met Tyr Val Ser Lys Lys Glu Ile Glu Val Arg Tyr Ala Glu Thr Asp
1               5                   10                  15

Gln Met Gly Ile Val Tyr His Ala Asn Tyr Leu Ile Trp Met Glu Val
            20                  25                  30

Gly Arg Thr Ala Leu Ile Lys Glu Leu Gly Phe Ser Tyr Ala Gln Leu
        35                  40                  45

Glu Ala Asp Gly Ala Leu Ala Pro Val Ile Asp Leu Gln Val Lys Tyr
    50                  55                  60

Lys Lys Pro Leu Leu Tyr Gly Glu Thr Ala Thr Val His Thr Trp Ile
65                  70                  75                  80

Glu Glu Tyr Asn Gly Leu Lys Thr Val Tyr Gly Tyr Glu Ile Gln Lys
                85                  90                  95

Pro Asp Gly Gln Thr Ala Ile Thr Gly Thr Thr Ser His Ile Cys Val
            100                 105                 110

Asp Lys Asp Thr Phe Arg Pro Ile Gln Phe Arg Lys Ala Phe Pro Ala
        115                 120                 125

Trp His Lys Val Tyr Glu Gln Ser Lys Lys Gln Val
    130                 135                 140

<210> SEQ ID NO 15
<211> LENGTH: 140
<212> TYPE: PRT
<213> ORGANISM: Bacillus pumilus SAFR-032

<400> SEQUENCE: 15

Met Tyr Val Ser Lys Lys Glu Ile Glu Val Arg Tyr Ala Glu Thr Asp
1               5                   10                  15

Gln Met Gly Ile Val Tyr His Ala Asn Tyr Leu Ile Trp Met Glu Val
            20                  25                  30

Gly Arg Thr Ala Leu Ile Lys Glu Leu Gly Phe Ser Tyr Ala Gln Leu
        35                  40                  45

Glu Ala Glu Gly Ala Leu Ala Pro Val Ile Asp Leu Gln Val Lys Tyr
    50                  55                  60

Lys Lys Pro Leu Leu Tyr Gly Glu Thr Ala Thr Val His Thr Trp Ile
65                  70                  75                  80

Glu Glu Tyr Asn Gly Leu Lys Thr Val Tyr Gly Tyr Glu Ile Gln Lys
                85                  90                  95

Pro Asp Gly Lys Thr Ala Ile Thr Gly Thr Thr Ser His Ile Cys Val
            100                 105                 110

Asp Lys Asp Thr Phe Arg Pro Ile Gln Phe Arg Lys Ala Phe Pro Ala
        115                 120                 125

Trp His Lys Val Tyr Glu Gln Ser Lys Lys Gln Val
    130                 135                 140

<210> SEQ ID NO 16
<211> LENGTH: 98
<212> TYPE: PRT
<213> ORGANISM: Bacillus sp. SG-1

<400> SEQUENCE: 16

```
Met Tyr Ile Ser Glu Lys Ser Ile Glu Val Arg Tyr Ala Glu Thr Asp
1               5                   10                  15

Gln Met Gly Val Val Tyr His Ala Asn Tyr Leu Val Trp Met Glu Leu
            20                  25                  30

Gly Arg Thr Lys Leu Ile Glu Asp Leu Gly Phe Arg Tyr Ala Asp Met
            35                  40                  45

Glu Lys Asp Gly Ile Ile Ser Pro Val Ile Asp Ile Glu Ile Ser Tyr
50                  55                  60

Lys Ser Pro Val Arg Tyr Gly Glu Lys Ala Phe Val Lys Thr Trp Ile
65                  70                  75                  80

Glu Ser Tyr Asp Gly Leu Arg Val Thr Tyr Gly Tyr Glu Ile Leu Asn
            85                  90                  95

Glu Lys

<210> SEQ ID NO 17
<211> LENGTH: 140
<212> TYPE: PRT
<213> ORGANISM: Bacillus megaterium DSM 319

<400> SEQUENCE: 17

Met Leu Val Ser Thr Lys Glu Ile Glu Val Arg Tyr Ala Glu Thr Asp
1               5                   10                  15

Gln Met Gly Val Val Tyr His Ala Asn Tyr Leu Val Trp Met Glu Ile
            20                  25                  30

Gly Arg Thr Gln Phe Ile Ser Asp Leu Gly Phe Ser Tyr Ala Gln Met
            35                  40                  45

Glu Arg Asp Gly Val Leu Ser Pro Val Ile Asp Ile Gln Ala Ser Tyr
50                  55                  60

Lys Lys Pro Leu His Tyr Gly Glu Thr Ala Val Val His Thr Trp Val
65                  70                  75                  80

Glu Asn Tyr Asp Gly Leu Arg Val Val Tyr Gly Tyr Glu Ile Phe Asn
            85                  90                  95

Ser Asn Glu Glu Leu Ala Leu Thr Gly Thr Ser Ser His Val Cys Val
            100                 105                 110

Lys Lys Glu Asn Phe Lys Pro Ile Ser Ile Arg Arg Asn Tyr Pro Glu
            115                 120                 125

Trp His Lys Ala Tyr Glu Glu Ala Lys Lys Gln Gly
            130                 135             140

<210> SEQ ID NO 18
<211> LENGTH: 144
<212> TYPE: PRT
<213> ORGANISM: Bacillus megaterium QM B1551

<400> SEQUENCE: 18

Met Leu Val Ser Lys Lys Glu Ile Glu Val Arg Tyr Ala Glu Thr Asp
1               5                   10                  15

Gln Met Gly Val Val Tyr His Ala Asn Tyr Leu Val Trp Met Glu Ile
            20                  25                  30

Gly Arg Thr Gln Phe Ile Ser Asp Leu Gly Phe Ser Tyr Ala Gln Met
            35                  40                  45

Glu Arg Asp Gly Val Leu Ser Pro Val Ile Asp Ile Gln Ala Ser Tyr
50                  55                  60

Lys Lys Pro Leu His Tyr Gly Glu Thr Ala Val Val His Thr Trp Val
65                  70                  75                  80
```

```
Glu Asn Tyr Asp Gly Leu Arg Val Val Tyr Gly Tyr Glu Ile Phe Asn
                85                  90                  95

Ser Asn Glu Glu Leu Ala Leu Thr Gly Thr Ser Ser His Val Cys Val
            100                 105                 110

Lys Lys Glu Asn Phe Lys Pro Ile Ser Ile Arg Arg Asn Tyr Pro Glu
        115                 120                 125

Trp His Lys Ala Tyr Glu Asp Ala Lys Lys Gln Gly Gln Ser Gln Glu
    130                 135                 140
```

<210> SEQ ID NO 19
<211> LENGTH: 139
<212> TYPE: PRT
<213> ORGANISM: Bacillus coagulans 36D1

<400> SEQUENCE: 19

```
Met Phe Val Ser Glu Thr Glu Val Lys Val Arg Tyr Ala Glu Thr Asp
1               5                   10                  15

Gln Met Gly Val Val Tyr His Ala Asn Tyr Leu Ile Trp Met Glu Val
            20                  25                  30

Gly Arg Thr Lys Leu Ile Glu Asp Leu Gly Phe Arg Tyr Ala Asp Met
        35                  40                  45

Glu Lys Asp Gly Ile Leu Ser Pro Val Ile Asp Ile Gln Ile Ser Tyr
    50                  55                  60

Lys Lys Pro Ala Arg Tyr Gly Glu Thr Val Thr Val Lys Thr Trp Val
65                  70                  75                  80

Asp Ala Tyr Asp Gly Leu Arg Val Thr Tyr Gly Tyr Glu Ile Tyr Thr
                85                  90                  95

Glu Thr Gly Asp Leu Ala Val Ala Ala Ser Ser Thr His Val Cys Val
            100                 105                 110

Lys Lys Asp Ser Phe Arg Pro Val Ser Phe Arg Arg Leu Tyr Pro Lys
        115                 120                 125

Trp His Glu Ala Tyr Gly Lys Ala Lys Lys Ser
    130                 135
```

<210> SEQ ID NO 20
<211> LENGTH: 138
<212> TYPE: PRT
<213> ORGANISM: Geobacillus thermoglucosidasius C56-YS93

<400> SEQUENCE: 20

```
Met Lys Val Val Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Asp Met
        35                  40                  45

Glu Lys Glu Gly Ile Ile Ser Pro Val Val Asp Leu Gln Val Ser Tyr
    50                  55                  60

Lys Lys Pro Leu His Tyr Gly Glu Thr Ala Thr Val Arg Thr Trp Ile
65                  70                  75                  80

Glu Ser Tyr Asp Gly Ile Arg Val Thr Tyr Gly Tyr Glu Ile Leu Thr
                85                  90                  95

Pro Asp Gly Glu Ile Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125
```

Trp His Glu Ala Tyr Glu Arg Ala Lys Lys
    130                 135

<210> SEQ ID NO 21
<211> LENGTH: 138
<212> TYPE: PRT
<213> ORGANISM: Geobacillus sp. C56-T3

<400> SEQUENCE: 21

Met Lys Val Ala Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Asp Met
        35                  40                  45

Glu Lys Glu Gly Ile Ile Ser Pro Val Val Asp Leu Gln Val Ser Tyr
    50                  55                  60

Lys Lys Pro Leu Arg Tyr Gly Glu Thr Ala Thr Val Arg Thr Trp Ile
65                  70                  75                  80

Asp Ala Tyr Asp Gly Ile Arg Val Thr Tyr Gly Tyr Glu Ile Leu Ala
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala Tyr Glu Arg Ala Lys Arg
    130                 135

<210> SEQ ID NO 22
<211> LENGTH: 138
<212> TYPE: PRT
<213> ORGANISM: Geobacillus sp. Y412MC61

<400> SEQUENCE: 22

Met Lys Val Ala Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Asp Met
        35                  40                  45

Glu Lys Glu Gly Ile Ile Ser Pro Val Val Asp Leu Gln Val Ser Tyr
    50                  55                  60

Lys Lys Pro Leu Arg Tyr Gly Glu Thr Ala Thr Val Arg Thr Trp Ile
65                  70                  75                  80

Asp Ala Tyr Asp Gly Ile Arg Val Thr Tyr Gly Tyr Glu Ile Leu Ala
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala Tyr Glu Arg Ala Lys Arg
    130                 135

<210> SEQ ID NO 23
<211> LENGTH: 138
<212> TYPE: PRT
<213> ORGANISM: Geobacillus sp. WCH70

<400> SEQUENCE: 23

Met Lys Val Ala Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Asp Met
        35                  40                  45

Glu Lys Gln Gly Ile Ile Ser Pro Val Val Asp Leu Gln Val Ser Tyr
    50                  55                  60

Lys Lys Pro Leu His Tyr Gly Glu Thr Ala Thr Val Arg Thr Trp Ile
65                  70                  75                  80

Asp Ala Tyr Asp Gly Ile Arg Val Thr Tyr Gly Tyr Glu Ile Leu Thr
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala Tyr Glu Arg Ala Lys Lys
    130                 135

<210> SEQ ID NO 24
<211> LENGTH: 138
<212> TYPE: PRT
<213> ORGANISM: Geobacillus kaustophilus HTA426

<400> SEQUENCE: 24

Met Lys Val Ala Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Asp Met
        35                  40                  45

Glu Lys Glu Gly Ile Ile Ser Pro Val Val Asp Leu Gln Val Ser Tyr
    50                  55                  60

Lys Lys Pro Leu His Tyr Gly Glu Thr Ala Thr Val Arg Thr Trp Ile
65                  70                  75                  80

Asp Ala Tyr Asp Gly Ile Arg Val Thr Tyr Gly Tyr Glu Ile Leu Ala
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala Tyr Glu Arg Ala Lys Arg
    130                 135

<210> SEQ ID NO 25
<211> LENGTH: 138
<212> TYPE: PRT
<213> ORGANISM: Geobacillus sp. G11MC16

<400> SEQUENCE: 25

Met Lys Val Ala Glu Lys Gln Ile Glu Val Arg Tyr Ala Glu Thr Asp
1               5                   10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Glu Met
            35                  40                  45

Glu Lys Glu Gly Val Ile Ser Pro Val Ile Asp Leu Gln Val Ser Tyr
 50                  55                  60

Lys Lys Pro Leu His Tyr Gly Glu Thr Ala Thr Val Arg Thr Trp Ile
 65                  70                  75                  80

Asp Ala Tyr Asp Gly Ile Arg Val Thr Tyr Gly Tyr Glu Ile Leu Ala
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala Tyr Glu Arg Ala Lys Arg
    130                 135

<210> SEQ ID NO 26
<211> LENGTH: 132
<212> TYPE: PRT
<213> ORGANISM: Geobacillus thermodenitrificans NG80-2

<400> SEQUENCE: 26

Met Lys Val Ala Glu Lys Gln Ile Glu Val Arg Tyr Ala Glu Thr Asp
 1               5                  10                  15

Gln Met Gly Val Val Tyr His Ala Asn Tyr Leu Val Trp Met Glu Val
            20                  25                  30

Gly Arg Thr Glu Leu Ile Lys Gln Leu Gly Phe His Tyr Ala Glu Met
            35                  40                  45

Glu Lys Glu Gly Val Ile Ser Pro Val Ile Asp Leu Gln Val Ser Tyr
 50                  55                  60

Lys Lys Pro Leu His Tyr Gly Glu Thr Ala Thr Val Arg Thr Trp Ile
 65                  70                  75                  80

Asp Ala Tyr Asp Gly Ile Arg Val Thr Tyr Gly Tyr Glu Ile Leu Ala
                85                  90                  95

Pro Asp Gly Glu Val Ala Val Thr Gly Lys Ser Gln His Val Cys Val
            100                 105                 110

Lys Arg Asp Thr Phe Arg Pro Ile Val Ile Arg Lys Tyr Phe Pro Asp
        115                 120                 125

Trp His Glu Ala
    130

<210> SEQ ID NO 27
<211> LENGTH: 144
<212> TYPE: PRT
<213> ORGANISM: Bacillus sp. NRRL B-14911

<400> SEQUENCE: 27

Met Leu Ile Ser Thr Lys Glu Ile Glu Val Arg Tyr Ala Glu Thr Asp
 1               5                  10                  15

Gln Met Gly Val Val Tyr His Ala Asn Tyr Leu Val Trp Met Glu Leu
            20                  25                  30

Gly Arg Thr Arg Leu Ile Glu Glu Leu Gly Phe Asn Tyr Ala Glu Leu
            35                  40                  45

Glu Lys Asp Gly Ile Ile Ser Pro Val Ile Asp Ile Ala Ala Ser Tyr
 50                  55                  60

Lys Lys Pro Val Arg Tyr Gly Leu Lys Ala Val Ile Arg Thr Trp Ile
 65                  70                  75                  80

```
Glu Glu Tyr Asp Gly Phe Arg Val Thr Tyr Gly Tyr Glu Ile Leu Thr
                85                  90                  95

Glu Gly Gly Glu Leu Ser Val Gly Ile Ser Lys His Val Cys Val
            100                 105                 110

Lys Lys Glu Asn Phe Arg Pro Ile Ser Ile Lys Arg Lys Tyr Pro Asp
        115                 120                 125

Trp His Glu Ala Tyr Glu Lys Ala Lys Lys Ala Pro Glu Ala Ala Glu
130                 135                 140
```

<210> SEQ ID NO 28
<211> LENGTH: 193
<212> TYPE: PRT
<213> ORGANISM: Magnetospirillum magneticum AMB-1

<400> SEQUENCE: 28

```
Met Arg Arg Gly Asn Asp Gly Asp Gly Asp Ser His Pro Asp Asp Gln
1               5                   10                  15

Arg Glu Glu Gly Ser His Pro Ala Pro Pro Cys Arg Gly Arg His His
            20                  25                  30

Arg Ser Arg Arg Arg Ser Leu Ala Cys Ala Arg Asp Asp Arg Leu Gly
        35                  40                  45

Gly Arg Leu Val Ala Val Asn Ala His Thr Phe Pro Val Arg Val Tyr
50                  55                  60

Tyr Glu Asp Thr Asp Ala Gly Gly Ile Val Tyr His Ser Asn Tyr Leu
65                  70                  75                  80

Lys Phe Ala Glu Arg Ala Arg Thr Glu Met Val Arg Glu Leu Gly Ile
                85                  90                  95

Ser Gln Arg Ala Met Leu Glu Asp Gly Glu Gly Thr Ala Phe Ala Val
            100                 105                 110

Arg Ser Ala Asn Leu Asp Phe Arg Pro Ala Lys Leu Asp Asp Leu
        115                 120                 125

Leu Ser Val Glu Thr Gln Val Ile Ser Ile Gly Ala Ser Ile Glu
130                 135                 140

Leu Asp Gln Arg Ile Val Arg Val Asp Asp Gly Thr Glu Leu Val His
145                 150                 155                 160

Leu Glu Val Arg Leu Gly Tyr Ile Thr Leu Ser Gly Lys Pro Ala Arg
                165                 170                 175

Ile Pro Ala Pro Val Arg Asp Leu Phe Ala Asn Arg Ile Ser Glu Arg
            180                 185                 190

Arg
```

<210> SEQ ID NO 29
<211> LENGTH: 139
<212> TYPE: PRT
<213> ORGANISM: Magnetospirillum magnetotacticum MS-1

<400> SEQUENCE: 29

```
Met Thr His Thr Phe Pro Ile Arg Val Tyr Tyr Glu Asp Thr Asp Ala
1               5                   10                  15

Gly Gly Ile Val Tyr His Ser Asn Tyr Leu Asn Phe Ala Glu Arg Ala
            20                  25                  30

Arg Thr Glu Met Val Arg Glu Leu Gly Ile Ser Gln Arg Ala Met Leu
        35                  40                  45

Glu Asp Gly Glu Gly Thr Ala Phe Ala Val Arg Ser Ala His Leu Asp
50                  55                  60
```

```
Phe Leu Arg Pro Ala Arg Leu Asp Asp Leu Leu Ser Val Glu Thr Gln
 65                  70                  75                  80

Val Ile Ser Ile Gly Gly Ala Ser Ile Glu Leu Asp Gln Arg Ile Leu
                 85                  90                  95

Arg Val Glu Asp Gly Thr Glu Leu Val Arg Leu Gly Val Arg Leu Gly
            100                 105                 110

Tyr Ile Thr Leu Ser Gly Lys Pro Ala Arg Ile Pro Ala Pro Val Arg
        115                 120                 125

Glu Leu Phe Ala Lys Arg Ile Ser Glu Arg Arg
130                 135

<210> SEQ ID NO 30
<211> LENGTH: 161
<212> TYPE: PRT
<213> ORGANISM: Burkholderia cenocepacia MC0-3

<400> SEQUENCE: 30

Met Arg Ala Met Thr Gln Pro Thr Arg Ser Pro Glu Ala Pro Ser Gly
 1               5                  10                  15

Phe Thr Trp Pro Val Arg Val Tyr Tyr Glu Asp Thr Asp Ala Gly Gly
                20                  25                  30

Ile Val Phe Tyr Ala Asn Tyr Leu Lys Phe Phe Glu Arg Ala Arg Thr
             35                  40                  45

Glu Trp Leu Arg Ala Cys Gly Val Asp Gln Arg Leu Ala Asp Asp
 50                  55                  60

Thr Gly Ala Ile Phe Ile Val Arg Ser Thr Ser Leu Asp Tyr Arg Ala
 65                  70                  75                  80

Pro Ala Arg Leu Asp Asp Thr Leu Thr Val Thr Ser Arg Pro Gly Arg
                 85                  90                  95

Ile Gly Arg Ala Ser Val Glu Phe Thr Gln Glu Ala Trp Cys Asp Asp
            100                 105                 110

Thr Leu Leu Val Ala Gly His Ile Arg Leu Gly Cys Val Asp Arg His
        115                 120                 125

Gly Ile Arg Pro Ala Ala Ile Pro Pro Val Val Leu Asp Ala Leu Gln
    130                 135                 140

Arg Gly Pro Val Ile Asp Ala Gly Gln Thr Gly Leu Ser Thr Lys Arg
145                 150                 155                 160

Ala

<210> SEQ ID NO 31
<211> LENGTH: 204
<212> TYPE: PRT
<213> ORGANISM: Rhodopseudomonas palustris BisA53

<400> SEQUENCE: 31

Met Ser Ala Ser Thr Pro Gly Arg Lys Thr Pro Arg Phe Leu Met Ile
 1               5                  10                  15

Asp Gly Ala Arg Gly Val Asp Met Pro Lys Pro Lys Gly Trp Pro Thr
                20                  25                  30

Pro Leu Pro Ser His Val Gln Leu Asp Gly Glu Ile Arg Asp Gly Ser
             35                  40                  45

His Arg Met Leu Val Arg Val Tyr Tyr Glu Asp Thr Asp Phe Ser Gly
 50                  55                  60

Ile Val Tyr His Ala Asn Tyr Leu Arg Phe Ile Glu Arg Gly Arg Ser
 65                  70                  75                  80
```

Asn Tyr Leu Arg Leu Leu Gly Ala Asp Gln Arg Ala Leu Phe Ala Asp
                85                  90                  95

Gly Ser Gly Ala Pro Gly Tyr Ala Phe Val Val Arg Gly Met Gln Leu
            100                 105                 110

Asp Phe Leu Lys Ser Ala Arg Met Asp Asp Val Leu Glu Val Val Thr
        115                 120                 125

Thr Pro Leu Asp Val Lys Gly Ala Ser Ile Thr Met Gly Gln Gln Ile
    130                 135                 140

Arg Arg Gly Gly Ile Val Leu Phe Asp Ala Lys Val Lys Ile Ala Phe
145                 150                 155                 160

Val Thr Gly Gly Arg Pro Arg Pro Ile Pro Lys Asn Ile Arg Thr Ala
                165                 170                 175

Met Thr Ala Asp Ser Thr Ala Pro Ser Ser Ala Asn Ser Ile Ala Ile
            180                 185                 190

Pro Asp His Ser His Phe Ala Gly Glu Leu Pro Cys
        195                 200

<210> SEQ ID NO 32
<211> LENGTH: 161
<212> TYPE: PRT
<213> ORGANISM: Burkholderia cenocepacia HI2424

<400> SEQUENCE: 32

Met Arg Ala Met Thr Gln Pro Thr Arg Ser Pro Glu Ala Pro Ser Gly
1               5                   10                  15

Phe Thr Trp Pro Val Arg Val Tyr Tyr Glu Asp Thr Asp Ala Gly Gly
            20                  25                  30

Ile Val Phe Tyr Ala Asn Tyr Leu Lys Phe Phe Glu Arg Ala Arg Thr
        35                  40                  45

Glu Trp Leu Arg Ala Cys Gly Val Asp Gln Arg Leu Ala Asp Asp
    50                  55                  60

Thr Gly Ala Ile Phe Ile Val Arg Ser Thr Ser Leu Asp Tyr Arg Ala
65                  70                  75                  80

Pro Ala Arg Leu Asp Asp Thr Leu Thr Ile Thr Ser Arg Pro Gly Arg
                85                  90                  95

Ile Gly Arg Ala Ser Val Glu Phe Thr Gln Glu Ala Trp Cys Gly Asp
            100                 105                 110

Thr Leu Leu Val Ala Gly His Ile Arg Leu Gly Cys Val Asp Arg His
        115                 120                 125

Gly Ile Arg Pro Ala Ala Ile Pro Pro Val Val Asp Ala Leu Gln
    130                 135                 140

Arg Gly Pro Val Ile Asp Ala Gly Gln Thr Gly Leu Ser Thr Lys Arg
145                 150                 155                 160

Ala

<210> SEQ ID NO 33
<211> LENGTH: 161
<212> TYPE: PRT
<213> ORGANISM: Burkholderia cenocepacia PC184

<400> SEQUENCE: 33

Met Arg Ala Met Thr Gln Pro Thr Arg Ser Pro Glu Ala Pro Ser Gly
1               5                   10                  15

Phe Thr Trp Pro Val Arg Val Tyr Tyr Glu Asp Thr Asp Ala Gly Gly
            20                  25                  30

```
Ile Val Phe Tyr Ala Asn Tyr Leu Lys Phe Phe Glu Arg Ala Arg Thr
            35                  40                  45

Glu Trp Leu Arg Ala Cys Gly Val Asp Gln Arg Leu Ala Asp Asp
 50                  55                  60

Thr Gly Ala Ile Phe Ile Val Arg Ser Thr Ser Leu Asp Tyr Arg Ala
 65                  70                  75                  80

Pro Ala Arg Leu Asp Asp Thr Leu Thr Ile Thr Ser Arg Pro Gly Arg
                 85                  90                  95

Ile Gly Arg Ala Ser Val Glu Phe Thr Gln Ala Trp Cys Gly Asp
            100                 105                 110

Thr Leu Leu Val Ala Gly His Ile Arg Leu Gly Cys Val Asp Arg His
                115                 120                 125

Gly Ile Arg Pro Ala Ala Ile Pro Pro Val Val Leu Asp Ala Leu Gln
130                 135                 140

Arg Gly Pro Val Ile Asp Ala Gly Gln Ser Gly Leu Ser Thr Lys Arg
145                 150                 155                 160

Ala
```

<210> SEQ ID NO 34
<211> LENGTH: 141
<212> TYPE: PRT
<213> ORGANISM: Magnetospirillum gryphiswaldense MSR-1

<400> SEQUENCE: 34

```
Met Ser Pro His Leu His Gln Ile Arg Val Tyr Trp Glu Asp Thr Asp
 1               5                  10                  15

Ala Gly Gly Ile Val Tyr His Ser Asn Tyr Leu Asn Phe Ala Glu Arg
                20                  25                  30

Ala Arg Thr Glu Met Val Arg Ala Met Gly Leu Lys Gln Ser Glu Leu
            35                  40                  45

Ala Asn Ala Gly Lys Gly His Val Phe Ala Val Arg Arg Ala Glu Ile
         50                  55                  60

Asp Phe Leu Lys Pro Ala Arg Leu Asp Leu Leu Gln Val Glu Thr
 65                  70                  75                  80

Thr Val Thr Ala Leu Gly Gly Ala Ser Met Glu Leu Ser Gln Thr Ile
                 85                  90                  95

Arg Arg Leu Asp Asp Gly Ala Asp Leu Ala Cys Leu His Ile Lys Leu
                100                 105                 110

Ala Phe Ile Thr Leu Asp Asp Gly Arg Pro Ala Arg Ile Pro Gly Trp
            115                 120                 125

Met Lys Asp Gln Leu Arg Asp Leu Glu Ser Glu Arg Arg
            130                 135                 140
```

<210> SEQ ID NO 35
<211> LENGTH: 158
<212> TYPE: PRT
<213> ORGANISM: Burkholderia ambifaria MEX-5

<400> SEQUENCE: 35

```
Met Thr Gln Pro Thr Arg Ser Pro Asp Ala Pro Ser Gly Phe Thr Trp
 1               5                  10                  15

Pro Val Arg Val Tyr Tyr Glu Asp Thr Asp Ala Gly Gly Ile Val Phe
                20                  25                  30

Tyr Ala Asn Tyr Leu Lys Phe Phe Glu Arg Ala Arg Thr Glu Trp Leu
            35                  40                  45
```

Arg Ala Cys Gly Ile Asp Gln Arg Arg Leu Ala Asp Asp Thr Gly Ala
            50                  55                  60

Ile Phe Ile Val Arg Ser Thr Ser Leu Asp Tyr Arg Ala Pro Ala Arg
65                  70                  75                  80

Leu Asp Asp Ala Leu Thr Val Thr Ser Arg Pro Gly Arg Ile Gly Arg
                    85                  90                  95

Ala Ser Val Glu Phe Thr Gln Glu Ala Trp Arg Gly Asp Thr Leu Leu
                100                 105                 110

Val Thr Gly His Ile Arg Leu Gly Cys Val Glu Arg Thr Gly Ile Arg
                115                 120                 125

Pro Ala Ala Ile Pro Gln Val Val Leu Asp Ala Leu Gln Arg Gly Pro
130                 135                 140

Val Thr Asp Ala Gly Gln Thr Val Leu Ser Thr Lys Leu Ala
145                 150                 155

<210> SEQ ID NO 36
<211> LENGTH: 161
<212> TYPE: PRT
<213> ORGANISM: Burkholderia ambifaria MC40-6

<400> SEQUENCE: 36

Met Arg Ala Met Thr Gln Pro Thr Arg Ser Pro Asp Ala Pro Ser Gly
1               5                   10                  15

Phe Thr Trp Pro Val Arg Val Tyr Tyr Glu Asp Thr Asp Ala Gly Gly
                20                  25                  30

Ile Val Phe Tyr Ala Asn Tyr Leu Lys Phe Phe Glu Arg Ala Arg Thr
                35                  40                  45

Glu Trp Leu Arg Ala Cys Gly Ile Asp Gln Arg Gln Leu Ala Asp Asp
            50                  55                  60

Thr Gly Ala Ile Phe Ile Val Arg Ser Thr Ser Leu Asp Tyr Arg Ala
65                  70                  75                  80

Pro Ala Arg Leu Asp Asp Ala Leu Thr Val Thr Ser Arg Pro Gly Arg
                    85                  90                  95

Ile Gly Arg Ala Ser Val Glu Phe Thr Gln Glu Ala Trp Arg Gly Asp
                100                 105                 110

Thr Leu Leu Val Thr Gly His Ile Arg Leu Gly Cys Val Asp Arg Thr
                115                 120                 125

Gly Ile Arg Pro Ala Ala Ile Pro Pro Val Val Leu Asp Ala Leu Gln
            130                 135                 140

Arg Gly Pro Val Thr Asp Ala Gly Gln Thr Val Leu Ser Thr Lys Leu
145                 150                 155                 160

Ala

<210> SEQ ID NO 37
<211> LENGTH: 160
<212> TYPE: PRT
<213> ORGANISM: Burkholderia ambifaria AMMD

<400> SEQUENCE: 37

Met Arg Ala Met Thr Gln Pro Thr Arg Ser Pro Asp Ala Pro Ser Gly
1               5                   10                  15

Phe Thr Trp Pro Val Arg Val Tyr Tyr Glu Asp Thr Asp Ala Gly Gly
                20                  25                  30

Ile Val Phe Tyr Ala Asn Tyr Leu Lys Phe Phe Glu Arg Ala Arg Thr
                35                  40                  45

```
Glu Trp Leu Arg Ala Cys Gly Ile Asp Gln Arg Arg Leu Ala Asp Asp
 50                  55                  60

Thr Gly Ala Ile Phe Ile Val Arg Ser Thr Ser Leu Asp Tyr Arg Ala
 65                  70                  75                  80

Pro Ala Arg Leu Asp Asp Ala Leu Thr Val Thr Ser Arg Pro Gly Arg
                 85                  90                  95

Ile Gly Arg Ala Ser Val Glu Phe Thr Gln Glu Ala Trp Arg Gly Asp
                100                 105                 110

Thr Leu Val Thr Gly His Ile Arg Leu Gly Cys Val Asp Arg Thr
            115                 120                 125

Gly Ile Arg Pro Ala Ala Ile Pro Pro Val Val Leu Asp Ala Leu Gln
130                 135                 140

Arg Gly Pro Val Thr Asp Ala Gly Gln Thr Val Leu Ser Thr Lys Leu
145                 150                 155                 160

<210> SEQ ID NO 38
<211> LENGTH: 151
<212> TYPE: PRT
<213> ORGANISM: Granulibacter bethesdensis CGDNIH1

<400> SEQUENCE: 38

Met Ile Met Glu Gly Arg His His Tyr Pro Val Arg Ile Tyr Tyr Glu
  1               5                  10                  15

Asp Thr Asp Ala Gly Gly Ile Val Tyr His Ala Asn Tyr Leu Arg Phe
                 20                  25                  30

Ala Glu Arg Ala Arg Thr Glu Met Leu Arg Asp Cys Gly Val Pro His
             35                  40                  45

Ala Glu Leu Thr Asp Asp His Gly Leu Met Phe Val Val Arg Arg Val
 50                  55                  60

Arg Ile Asp Tyr Arg Arg Pro Ala Leu Leu Asp Asp Leu Leu Thr Val
 65                  70                  75                  80

Val Thr Arg Val Glu Ser Met Gly Ala Ala Ser Ala Glu Leu Glu Gln
                 85                  90                  95

Arg Val Glu Gly Pro Glu Gly Glu Leu Arg Ala Leu Leu Arg Ile Gly
                100                 105                 110

Leu Ala Cys Val Lys Ile Asp Asp Gln Lys Pro Ala Arg Val Pro Asp
            115                 120                 125

Arg Trp Lys Glu Ala Leu Asp Glu Leu Ser Arg Ser Gly Thr Ser Pro
130                 135                 140

Val Pro Thr Leu Gly Glu Gln
145                 150

<210> SEQ ID NO 39
<211> LENGTH: 141
<212> TYPE: PRT
<213> ORGANISM: Haemophilus somnus 129PT

<400> SEQUENCE: 39

Met Pro Val Phe Lys Leu Pro Val Arg Val Tyr Tyr Glu Asp Thr Asp
  1               5                  10                  15

Ala Gly Gly Val Val Tyr His Ala Arg Tyr Leu His Phe Phe Glu Arg
                 20                  25                  30

Ala Arg Thr Glu Tyr Leu Arg Thr Leu Asn Phe Ser Gln Gln Asn Leu
             35                  40                  45

Leu Asn Glu Arg Lys Val Ala Phe Val Val Lys Ser Ile Gln Ile Asp
 50                  55                  60
```

Tyr Cys Val Pro Ala Lys Leu Asp Asp Leu Leu Ile Val Glu Thr Tyr
 65                  70                  75                  80

Val Val Ala Ile Lys Gly Ala Ser Ile Val Phe Ser Gln Ile Leu Lys
                 85                  90                  95

Arg Asp Asp Glu Ile Ile Ser Gln Ala Val Val Lys Val Ala Ser Val
            100                 105                 110

Asp Leu Val Lys Met Arg Pro Val Ala Ile Pro Gln Glu Ile Lys Ala
        115                 120                 125

Glu Ile Lys Leu Asn Asp Asn Ile Phe Gly Val Met Ser
    130                 135                 140

<210> SEQ ID NO 40
<211> LENGTH: 141
<212> TYPE: PRT
<213> ORGANISM: Haemophilus somnus 2336

<400> SEQUENCE: 40

Met Pro Val Phe Lys Leu Pro Val Arg Val Tyr Tyr Glu Asp Thr Asp
1               5                   10                  15

Ala Gly Gly Val Val Tyr His Ala Arg Tyr Leu His Phe Phe Glu Arg
            20                  25                  30

Ala Arg Thr Glu Tyr Leu Arg Thr Leu Asn Phe Ser Gln Gln Asn Leu
        35                  40                  45

Leu Asn Glu Arg Lys Val Ala Phe Val Val Lys Ser Met Gln Ile Asp
    50                  55                  60

Tyr Cys Val Pro Ala Lys Leu Asp Asp Leu Leu Ile Val Glu Thr Tyr
 65                  70                  75                  80

Val Val Ala Ile Lys Gly Ala Ser Ile Val Phe Ser Gln Ile Leu Lys
                 85                  90                  95

Arg Asp Asp Glu Ile Ile Ser Gln Ala Val Val Lys Val Ala Ser Val
            100                 105                 110

Asp Leu Val Lys Met Arg Pro Val Ala Ile Pro Gln Glu Ile Lys Ala
        115                 120                 125

Glu Ile Lys Leu Asn Asp Asn Ile Phe Gly Val Met Ser
    130                 135                 140

<210> SEQ ID NO 41
<211> LENGTH: 131
<212> TYPE: PRT
<213> ORGANISM: Proteus mirabilis HI4320

<400> SEQUENCE: 41

Met Arg Phe Leu Trp Pro Val Arg Val Tyr Tyr Glu Asp Thr Asp Ala
1               5                   10                  15

Gly Gly Val Val Tyr His Ala Ser Tyr Leu Lys Tyr Phe Glu Arg Ala
            20                  25                  30

Arg Thr Glu Leu Leu Arg Glu Lys Gly Phe Tyr Gln His Asp Leu Arg
        35                  40                  45

Glu Tyr Asp His Val Ala Phe Val Val Arg Lys Leu Thr Ile Asp Tyr
    50                  55                  60

Ile Ala Pro Ala Arg Leu Asp Glu Leu Leu Lys Val Glu Ser Glu Ile
 65                  70                  75                  80

Thr Thr Leu Arg Gly Ala Ser Met Thr Phe Ser Gln Lys Leu Ile Asn
                 85                  90                  95

Gln Asp Gly Val Val Leu Cys Arg Ala Asp Val Leu Val Cys Val
            100                 105                 110

Asp Ser Leu Lys Met Lys Pro Val Gly Leu Pro Lys Ser Ile Ile Ala
            115                 120                 125

Glu Phe Lys
    130

<210> SEQ ID NO 42
<211> LENGTH: 158
<212> TYPE: PRT
<213> ORGANISM: Burkholderia ambifaria IOP40-10

<400> SEQUENCE: 42

Met Thr Gln Pro Thr Arg Ser Pro Asp Ala Pro Ser Gly Phe Thr Trp
1               5                   10                  15

Pro Val Arg Val Tyr Tyr Glu Asp Thr Asp Ala Gly Gly Ile Val Phe
            20                  25                  30

Tyr Ala Asn Tyr Leu Lys Phe Phe Glu Arg Ala Arg Thr Glu Trp Leu
        35                  40                  45

Arg Ala Cys Gly Ile Asp Gln Arg Arg Leu Ala Asp Val Thr Gly Ala
    50                  55                  60

Ile Phe Ile Val Arg Ser Thr Ser Leu Asp Tyr Arg Ala Pro Ala Arg
65                  70                  75                  80

Leu Asp Asp Ala Leu Thr Val Thr Ser Arg Pro Gly Arg Ile Gly Arg
                85                  90                  95

Ala Ser Val Glu Phe Thr Gln Glu Ala Trp Arg Gly Asp Thr Leu Leu
            100                 105                 110

Val Thr Gly His Ile Arg Leu Gly Cys Val Asp Arg Thr Gly Ile Arg
        115                 120                 125

Pro Ala Ala Ile Pro Pro Val Val Leu Asp Ala Leu Gln Arg Gly Pro
    130                 135                 140

Val Thr Asp Ala Gly Gln Thr Val Leu Ser Thr Lys Leu Ala
145                 150                 155

<210> SEQ ID NO 43
<211> LENGTH: 142
<212> TYPE: PRT
<213> ORGANISM: Proteus mirabilis ATCC 29906

<400> SEQUENCE: 43

Met Gly Leu Leu Lys Glu Cys Lys Asp Gly Ile Met Arg Phe Leu Trp
1               5                   10                  15

Pro Val Arg Val Tyr Tyr Glu Asp Thr Asp Ala Gly Gly Val Val Tyr
            20                  25                  30

His Ala Ser Tyr Leu Lys Tyr Phe Glu Arg Ala Arg Thr Glu Leu Leu
        35                  40                  45

Arg Glu Lys Gly Phe Tyr Gln His Asp Leu Arg Glu Tyr Asp His Val
    50                  55                  60

Ala Phe Val Val Arg Lys Leu Thr Ile Asp Tyr Ile Ala Pro Ala Arg
65                  70                  75                  80

Leu Asp Glu Leu Leu Lys Val Glu Ser Glu Ile Thr Thr Leu Arg Gly
                85                  90                  95

Ala Ser Met Thr Phe Ser Gln Lys Leu Ile Asn Gln Asp Gly Val Val
            100                 105                 110

Leu Cys Arg Ala Asp Val Leu Val Cys Val Asp Ser Leu Lys Met
        115                 120                 125

Lys Pro Val Gly Leu Pro Lys Ser Ile Ile Ala Glu Phe Lys
    130                 135                 140

<210> SEQ ID NO 44
<211> LENGTH: 191
<212> TYPE: PRT
<213> ORGANISM: Rhodopseudomonas palustris BisB18

<400> SEQUENCE: 44

```
Met Phe Asp Gly Ala His Gly Ile Asp Leu Pro Lys Pro His Val Ala
1               5                   10                  15
Ser Thr Pro Ala Ala Pro Ser His Ala His Leu Asp Gly Glu Ile Cys
            20                  25                  30
Asp Gly Gly His Arg Met Leu Val Arg Val Tyr Tyr Glu Asp Thr Asp
        35                  40                  45
Phe Ser Gly Ile Val Tyr His Ala Asn Tyr Leu Arg Phe Leu Glu Arg
    50                  55                  60
Gly Arg Ser Asn Tyr Leu Arg Leu Gly Ala Asp Gln Arg Ala Leu
65                  70                  75                  80
Phe Ser Asp Gly Val Gly Glu Ala Pro Gly Tyr Ala Phe Val Val Arg
                85                  90                  95
Ala Met Gln Leu Glu Phe Leu Arg Ser Ala Arg Met Asp Asp Leu Leu
            100                 105                 110
Glu Val Glu Thr Arg Pro Leu Glu Val Lys Gly Ala Ser Ile Thr Met
        115                 120                 125
Gly Gln Arg Ile Leu Arg Asp Gly Thr Val Leu Phe Glu Ala Lys Val
    130                 135                 140
Lys Val Ala Phe Val Ser Gly Gly Arg Pro Arg Pro Ile Pro Lys Ala
145                 150                 155                 160
Ile Arg Thr Ala Met Ser Ala Asp Gly Ala Gly Pro Asp Phe Ala Ser
                165                 170                 175
Ser Asn Val Met Ala Ser Lys Ser Ile Ser Gly Asp Glu Pro Cys
            180                 185                 190
```

<210> SEQ ID NO 45
<211> LENGTH: 160
<212> TYPE: PRT
<213> ORGANISM: Azospirillum sp. B510

<400> SEQUENCE: 45

```
Met Ser Asp Ala Ala Pro Ser Leu Ser Gly Cys Phe Ala Glu Asp Gly
1               5                   10                  15
Thr His Arg Tyr Arg Leu Arg Val Tyr Tyr Glu Asp Thr Asp Ala Gly
            20                  25                  30
Gly Ile Val Tyr His Ala Asn Tyr Leu Arg Phe Ala Glu Arg Ala Arg
        35                  40                  45
Thr Glu Met Leu Phe Leu Leu Gly Phe Arg Gln Arg Glu Met Ala Gln
    50                  55                  60
Gly Ser Gly Asp Val Thr Gly Val Ser Phe Ala Val Arg Arg Leu Thr
65                  70                  75                  80
Ile Asp Phe Asp Ala Pro Ala Lys Leu Glu Asp Thr Leu Glu Val Glu
                85                  90                  95
Thr Arg Ile Val Asp Ile Arg Gly Ala Ser Phe Ala Val Ala Gln Val
            100                 105                 110
Ile Arg Arg Asp Gly Arg Ala Leu Ala Arg Asp Leu Gln Leu Val
        115                 120                 125
Thr Ile Asn Arg Ala Gly Arg Ala Val Arg Leu Pro Glu Pro Val Lys
    130                 135                 140
```

```
Ala Ala Met Glu Thr Leu His Ala Lys Gln Thr Ala Ala Lys Pro Ser
145                 150                 155                 160
```

```
<210> SEQ ID NO 46
<211> LENGTH: 148
<212> TYPE: PRT
<213> ORGANISM: Rhodopseudomonas palustris DX-1

<400> SEQUENCE: 46
```

```
Met Pro His Pro Leu Asp Gly Ala Ile Ile Asp Gly Ala His His Met
1               5                   10                  15

His Val Arg Val Tyr Tyr Glu Asp Thr Asp Phe Ser Gly Ile Val Tyr
                20                  25                  30

His Ala Asn Tyr Leu Arg Phe Met Glu Arg Gly Arg Thr Asn Tyr Leu
            35                  40                  45

Arg Leu Leu Gly Ala Ala Gln Ser Glu Leu Phe Glu Glu Ala Glu Asn
    50                  55                  60

Glu Thr Pro Gly Phe Ala Phe Val Val Arg Ala Met Gln Leu Asp Phe
65                  70                  75                  80

Leu Arg Ser Ala Lys Met Asp Asp Leu Leu Glu Val Ile Thr Arg Pro
                85                  90                  95

Ile Glu Val Arg Gly Ala Ser Ile Thr Met Gln Gln Gln Ile Lys Arg
                100                 105                 110

Gly Asp Leu Val Leu Met Glu Ala Lys Val Lys Val Ala Phe Val Ser
            115                 120                 125

Gly Gly Arg Ala Arg Pro Ile Pro Val Pro Leu Arg Leu Ala Met Lys
    130                 135                 140

Ala Asp Val Asn
145
```

```
<210> SEQ ID NO 47
<211> LENGTH: 149
<212> TYPE: PRT
<213> ORGANISM: Bradyrhizobium sp. BTAi1

<400> SEQUENCE: 47
```

```
Met Thr His Gln His Leu Asp Gly Glu Ile Arg Asp Gly Arg His His
1               5                   10                  15

Met Gln Val Arg Val Tyr Tyr Glu Asp Thr Asp Phe Ser Gly Ile Val
                20                  25                  30

Tyr His Ala Asn Tyr Leu Arg Phe Met Glu Arg Gly Arg Thr Asn His
            35                  40                  45

Leu Arg Leu Met Gly Ala Glu Gln His Ala Leu Phe Ala Glu Ala Ala
    50                  55                  60

Ser Glu Ala Pro Gly Phe Ala Phe Val Val Arg Ser Met Thr Leu Asp
65                  70                  75                  80

Phe Leu Arg Pro Ala Arg Met Asp Asp Val Leu Asp Val Val Thr Trp
                85                  90                  95

Pro Ile Ala Val Lys Gly Ala Ser Ile Thr Leu Ala Gln Glu Val Arg
                100                 105                 110

Arg Gly Glu Glu Val Leu Val Lys Ala Asp Val Arg Val Ala Phe Ile
            115                 120                 125

Ser Gly Gly Lys Ala Gln Pro Ile Pro Arg Pro Leu Arg Asp Leu Met
    130                 135                 140

Lys Ala Asp Leu Ala
145
```

<210> SEQ ID NO 48
<211> LENGTH: 172
<212> TYPE: PRT
<213> ORGANISM: Rhodospirillum centenum SW

<400> SEQUENCE: 48

Met Ser Asp Gly Pro Glu Ala Pro Arg Gly Pro Ala Thr Gly His Leu
1               5                   10                  15

Val Gly Pro Leu His Val Tyr Pro Cys Arg Val Tyr Tyr Glu Asp Thr
            20                  25                  30

Asp Ala Gly Gly Ile Val Tyr His Ala Thr Tyr Leu Arg Tyr Cys Glu
        35                  40                  45

Arg Ala Arg Thr Glu Met Met Arg Leu Leu Gly Val Pro His Ser Ala
50                  55                  60

Met Val Ala Glu Ser Gly Val Ala Phe Ala Val Arg Arg Cys Glu Ile
65                  70                  75                  80

Asp Tyr Leu Arg Pro Ala Arg Leu Asp Asp Ala Leu Glu Val His Thr
                85                  90                  95

Glu Ile Ser Asp Ile Gly Gly Ala Thr Leu Asp Ala Val Gln Ile Ile
            100                 105                 110

Arg Arg Thr Phe Ala Thr Gly Ala Gly Tyr Ala Asp Gly Ser Ala Gly
        115                 120                 125

Ser Ala Thr Asp Gly Asp Val Leu Val His Val Arg Leu Arg Leu Ala
130                 135                 140

Cys Ile Asn Gln Ser Gly Arg Pro Ala Arg Leu Pro Asn Ala Val Arg
145                 150                 155                 160

Thr Ala Leu Lys Pro Leu Phe Pro Arg Pro Ala Pro
                165                 170

<210> SEQ ID NO 49
<211> LENGTH: 144
<212> TYPE: PRT
<213> ORGANISM: Methylosinus trichosporium OB3b

<400> SEQUENCE: 49

Met Ile Ala Pro Val Pro His Arg Leu Ser Val Arg Val Tyr Tyr Glu
1               5                   10                  15

Asp Thr Asp Phe Ser Gly Leu Val Tyr His Ala Ser His Leu Arg Phe
            20                  25                  30

Met Glu Arg Gly Arg Thr Glu Leu Leu Arg Asp Leu Gly Ile Phe Gln
        35                  40                  45

Arg Ala Leu Leu Glu Ser Pro Gly Gly Leu Phe Val Val Arg
50                  55                  60

Ala Ile Thr Ile Asp Phe Arg Arg Pro Ala Leu Met Asp Asp Leu Leu
65                  70                  75                  80

Thr Val Glu Thr Arg Val Glu Gln Val Ala Gly Ala Ser Val Asp Leu
                85                  90                  95

Ala Gln Arg Val Leu Arg Gly Glu Glu Pro Leu Val Thr Ala Leu Val
            100                 105                 110

Lys Val Ala Ala Val Glu Gly Gly Lys Ala Arg Arg Leu Pro Ala Asp
        115                 120                 125

Val Arg Gln Lys Phe Glu Ser Ala Leu Ala Pro Ala Pro Pro Pro
130                 135                 140

<210> SEQ ID NO 50
<211> LENGTH: 163

<212> TYPE: PRT
<213> ORGANISM: Rhodopseudomonas palustris HaA2

<400> SEQUENCE: 50

```
Met Thr Thr Leu Ile Ala Ser Ala Ser Ala Ile Gln Val Glu Gln Val
1               5                   10                  15

Ser His Pro Leu Asp Gly Ala Ile Ile Asp Gly Ala His His Met Gln
            20                  25                  30

Val Arg Val Tyr Tyr Glu Asp Thr Asp Phe Ser Gly Ile Val Tyr His
        35                  40                  45

Ala Asn Tyr Leu Arg Phe Met Glu Arg Gly Arg Thr Asn Tyr Leu Arg
    50                  55                  60

Leu Leu Gly Ala Ala Gln Ser Glu Leu Phe Ala Glu Ala Glu Ser Glu
65                  70                  75                  80

Thr Pro Gly Phe Ala Phe Val Val Arg Ala Met Gln Leu Asp Phe Leu
                85                  90                  95

Lys Ser Ala Lys Met Asp Asp Leu Leu Asp Val Ile Thr Arg Pro Val
            100                 105                 110

Glu Val Arg Gly Ala Ser Ile Thr Met Gln Gln Glu Ile Arg Arg Asp
        115                 120                 125

Glu Leu Leu Leu Leu Lys Ala Ser Val Lys Val Ala Phe Val Ser Gly
    130                 135                 140

Gly Arg Ala Arg Pro Ile Pro Val Pro Leu Arg Val Ala Met Lys Ala
145                 150                 155                 160

Asp Val Ala
```

<210> SEQ ID NO 51
<211> LENGTH: 153
<212> TYPE: PRT
<213> ORGANISM: Methylobacterium extorquens PA1

<400> SEQUENCE: 51

```
Met Thr Gly Ser Pro Arg Thr Arg Thr Ser Met Asp Pro Thr Thr Gly
1               5                   10                  15

Ala Asp Ala His Arg Leu Pro Leu Arg Ile Tyr Tyr Glu Asp Thr Asp
            20                  25                  30

Phe Ser Gly Phe Val Tyr His Ala Ser Tyr Leu Arg Phe Met Glu Arg
        35                  40                  45

Gly Arg Thr Glu Leu Leu Arg Thr Leu Ala Gly Asp Gln Ser Glu Met
    50                  55                  60

His Ala Glu Gly Thr Gly Leu Val Phe Val Arg Lys Met Thr Leu
65                  70                  75                  80

Asp Phe Leu Lys Pro Ala Arg Met Asp Asp Trp Ile Glu Val His Thr
                85                  90                  95

Arg Ser Ser Glu Leu Arg Gly Ala Ser Met His Leu Ala Gln Val
            100                 105                 110

Arg Arg Gly Asp Glu Val Leu Val Arg Ala Asp Val Val Ala Cys
        115                 120                 125

Val Arg Asp Gly Arg Ala Ile Arg Leu Pro Glu Gly Leu Arg Arg Ala
    130                 135                 140

Leu Thr Pro Ala Gly Leu Arg Ser Ala
145                 150
```

<210> SEQ ID NO 52
<211> LENGTH: 90
<212> TYPE: DNA

```
<213> ORGANISM: Artificial Sequence
<220> FEATURE:
<223> OTHER INFORMATION: IPTG-inducible trcY promoter

<400> SEQUENCE: 52
ctgaaatgag ctgttgacaa ttaatcatcc ggctcgtata atgtgtggaa ttgtgagcgg      60
ataacaattt cacactaagg aggaaaaaaa                                       90
```

GENETICALLY ENGINEERED MICROORGANISMS COMPRISING 4-HYDROXYBENZOYL-COA THIOESTERASES AND METHODS OF USING THE SAME FOR PRODUCING FREE FATTY ACIDS AND FATTY ACID DERIVATIVES

CROSS-REFERENCE TO RELATED APPLICATIONS

This application claims benefit of priority to U.S. provisional patent application 61/426,568 of the same title filed Dec. 23, 2010, which is hereby incorporated by reference in its entirety.

REFERENCE TO A SEQUENCE LISTING

This application contains references to amino acid sequences and/or nucleic acid sequences which have been submitted concurrently herewith as the sequence listing text file entitled "2010EM383 (PM0010) sequences.TXT", file size 71.1 KiloBytes (KB), created on Dec. 12, 2011. The aforementioned sequence listing is hereby incorporated by reference in its entirety pursuant to 37 C.F.R. §1.52(e)(5).

FIELD OF THE INVENTION

The invention relates to compositions and methods for producing free fatty acids and fatty acid derivatives in microorganisms, including photosynthetic microorganisms such as cyanobacteria and microalgae.

BACKGROUND OF THE INVENTION

Biofuels

Biofuels represent renewable energy sources from living organisms, such as higher plants, fungi, or bacteria. Photosynthetic life forms capture light energy and subsequently convert it into the free energy of organic compounds based on fixed $CO_2$, using water as the ultimate electron donor. Currently, two major technologies are employed for generating biofuels using phototrophic organisms: first, plant-based biofuel production via fermentation of the plant's sugar content to ethanol and, second, to a much lesser extent, algae-derived biodiesel production through lipid extraction of biomass from large-scale cultures (Angermayr et al., 2009, *Curr Opin Biotechnol*, 20(3): 257-263).

Lipids

Biological lipids are a chemically diverse group of compounds, the common and defining feature of which is their insolubility in water. The biological functions of lipids are equally diverse. Fats and oils are the principal storage forms of energy in many organisms, and phospholipids and sterols make up about half the mass of biological membranes. Other lipids, although present in relatively small quantities, play crucial roles as enzyme cofactors, electron carriers, light-absorbing pigments, hydrophobic anchors, emulsifying agents, hormones, and intracellular messengers (Lodish, H., *Molecular Cell Biology*, 6$^{th}$ ed., St. Martin's Press (2008)).

Fatty Acids

Fatty acids are carboxylic acids with hydrocarbon chains of 4 to 36 carbons. In some fatty acids, this chain is fully saturated (meaning it contains no double bonds) and unbranched; others contain one (monounsaturated) or more double bonds (polyunsaturated). A few contain three-carbon rings or hydroxyl groups. A simplified nomenclature for these compounds specifies the chain length and number of double bonds, separated by a colon; the 16-carbon saturated palmitic acid is abbreviated 16:0, and the 18-carbon oleic acid, with one double bond, is 18:1. The positions of any double bonds are specified by superscript numbers following $\Delta$ (delta); a 20-carbon fatty acid with one double bond between C-9 and C-10 (C-1 being the carboxyl carbon), and another between C-12 and C-13, is designated 20:2 ($\Delta^{9,12}$), for example. The most commonly occurring fatty acids have even numbers of carbon atoms in an unbranched chain of 12 to 24 carbons. The even number of carbons results from the mode of synthesis of these compounds, which involves condensation of acetate (two-carbon) units. (Lehninger et al., *Principles of Biochemistry*, Vol. 1, Macmillan, 2005).

The position of double bonds in unsaturated fatty acids also is irregular; in most monounsaturated fatty acids, the double bond is between C-9 and C-10 ($\Delta^9$), and the other double bonds of polyunsaturated fatty acids are generally $\Delta^{12}$ and $\Delta^{15}$. The double bonds of polyunsaturated fatty acids are almost never conjugated (alternating single and double bonds), but commonly are separated by a methylene group (—CH═CH—CH$_2$—CH═CH—). The physical properties of the fatty acids, and of compounds that contain them, are largely determined by the length and degree of unsaturation of the hydrocarbon chain, i.e., the longer the fatty acyl chain and the fewer the double bonds, the lower the solubility in water. (Lehninger et al., *Principles of Biochemistry*, Vol. 1, Macmillan, 2005).

Fatty Acid Biosynthesis

The irreversible formation of malonyl-CoA from acetyl-CoA is catalyzed by acetyl-CoA carboxylase in what is considered to be the first committed step in fatty acid biosynthesis (FIG. 1). Acetyl-CoA carboxylase contains biotin as its prosthetic group, covalently bound by amide linkage to the s-amino group of a lysine residue on one of the three subunits of the enzyme molecule. The carboxyl group, derived from bicarbonate ($HCO_3^-$), is first transferred to biotin in an ATP-dependent reaction. The biotinyl group serves as a temporary carrier of $CO_2$, transferring it to acetyl-CoA in the second step to yield malonyl-CoA. (Lehninger et al., *Principles of Biochemistry*, Volume 1, Macmillan, 2005).

In contrast to other heterotrophic bacteria, such as *E. coli*, which have to metabolize glucose from media into acetyl-CoA in order to initiate the fatty acid synthesis, in cyanobacteria, the precursor for fatty acid synthesis, i.e., acetyl-CoA, directly comes from the Calvin-Benson cycle which fixes carbon dioxide using energy and reducing power provided by the light reactions of photosynthesis.

The reaction sequence by which the long chains of carbon atoms in fatty acids are assembled consists of four steps: (1) condensation; (2) reduction; (3) dehydration; and (4) reduction. The saturated acyl group produced during this set of reactions is recycled to become the substrate in another condensation with an activated malonyl group. With each passage through the cycle, the fatty acyl chain is extended by two carbons. In many cells, chain elongation terminates when the chain reaches 16 carbons, and the product (palmitate, 16:0) leaves the cycle. The methyl and carboxyl carbon atoms of the acetyl group become C-16 and C-15, respectively, of the palmitate; the rest of the carbon atoms are derived from malonyl-CoA. All of the reactions in the synthetic process are catalyzed by a multi-enzymatic complex, the fatty acid synthase (Lehninger et al., *Principles of Biochemistry*, Volume 1, Macmillan, 2005).

The Elongation Cycle in Fatty Acid Synthesis

Fatty acid synthesis represents a central, conserved process by which acyl chains are produced for utilization in a number of end-products such as biological membranes. The enzyme system, which catalyzes the synthesis of saturated long-chain fatty acids from acetyl CoA, malonyl-CoA, and NADPH, is called the fatty acid synthase (FAS) (FIG. 1). Fatty acid synthases (FASs) can be divided into two classes, type I and II, which are primarily present in eukaryotes and in bacteria and plants respectively. They are characterized by being composed of either large multifunctional polypeptides in the case of type I or consisting of discretely expressed mono-functional proteins in the type II system. (Chan D. and Vogel H, *Biochem J.*, 2010, 430(1):1-19). The fatty acid synthase contains six catalytic activities and contains beta-ketoacyl synthase (KS), acetyl/malonyl transacylase (AT/MT), beta-hydroxyacyl dehydratase (DH), enoyl reductase (ER), beta-ketoacyl reductase (KR), acyl carrier protein (ACP), and thioesterase (TE) (Chirala and Wakil, *Lipids*, 2004, 39(11): 1045-53). It has been shown that the reactions leading to fatty acid synthesis in higher organisms are very much like those of bacteria (Berg et al, *Biochemistry*, $6^{th}$ ed., Macillan, 2008).

Fatty acid biosynthesis is initiated by the fatty acid synthase component enzyme acetyltransferase loading the acyl primer, usually acetate, from coenzyme A (CoA) to a specific binding site on fatty acid synthase (FAS). At the end of the process, termination of chain elongation occurs by removing the product from the fatty acid synthase (FAS) either by transesterification to an appropriate acceptor or by hydrolysis. The respective enzymes are usually palmitoyl transferase and thioesterase. The reaction sequence between initiation and termination involves the elongation of enzyme-bound intermediates by several iterative cycles of a distinct set of reaction steps. Each cycle includes (i) malonyl-transacylation from CoA to the enzyme by malonyl transferase; (ii) condensation of acyl-enzyme with enzyme-bound malonate to 3-ketoacyl-enzyme by 3-ketoacyl synthase, (iii) reduction of the 3-keto- to the 3-hydroxyacyl intermediate by ketoacyl reductase, (iv) dehydration of 3-hydroxyacyl enzyme to 2,3-trans-enoate by dehydratase, and, (v) finally, reduction of the enoate to the saturated acyl-enzyme by enoyl reductase. The prosthetic group, 4'-phosphopantetheine, plays a central role in substrate binding, processing of intermediates, and communicating of intermediates between the various catalytic centers of fatty acid synthase (FAS). This cofactor is bound covalently to a specific serine hydroxyl group of the ACP domain or, depending on the FAS system, to the ACP component of FAS. In some bacteria, the iterative sequence of elongation cycles may be interrupted at a chain length of 10 carbons by one cycle involving an intrinsic isomerase converting the 2-trans- into the 3-cis-decenoyl intermediate, which is subsequently not reduced but further elongated to long-chain monounsaturated fatty acids (Schweizer and Hofmann, *Microbiol Mol Biol Rev.*, 2004, 68(3): 501-17).

Acyl Carrier Protein (ACP)

The acyl carrier protein (ACP), the cofactor protein that covalently binds fatty acyl intermediates via a phosphopantetheine linker during the synthesis process, is central to fatty acid synthesis. It is a highly conserved protein that carries acyl intermediates during fatty acid synthesis. ACP supplies acyl chains for lipid and lipoic acid synthesis, as well as for quorum sensing, bioluminescence and toxin activation. Furthermore, ACPs or PCPs (peptidyl carrier proteins) also are utilized in polypeptide and non-ribosomal peptide synthesis, which produce important secondary metabolites, such as, the lipopeptide antibiotic daptomycin and the iron-carrying siderophore enterobactin (Chan and Vogel, *Biochem. J.*, 2010, 430:1-19).

In yeast and mammals, ACP exists as a separate domain within a large multifunctional fatty acid synthase polyprotein (type I FAS), whereas it is a small monomeric protein in bacteria and plants (type II FAS) (Byers and Gong, *Biochem Cell Biol.*, 2007, 85(6): 649-62).

In *E. coli*, ACP is highly abundant, comprising approximately 0.25% of all soluble proteins and it represents one of four major protein—protein interaction hubs, the others being DNA and RNA polymerases as well as ribosome-associated proteins. In type I FAS systems, ACP is part of large, multi-domain polypeptides that also carry the other protein domains for FA synthesis in a linear fashion. Although the architecture and sequence identity of the type I FAS systems are different from the type II dissociated enzymes, many of the functional units in these complexes are similar. On the other hand, other domains, such as the enoyl reductase and dehydratase enzymes, vary significantly between the type Ia, Ib and II systems (Chan and Vogel, *Biochem. J.*, 2010, 430: 1-19).

Acyl-ACP Thioesterases

The major termination reaction of fatty acid biosynthesis is catalyzed by acyl-acyl carrier protein (acyl-ACP) thioesterases in eukaryotes. Previous studies have shown that the acyl-ACP thioesterase enzyme terminates acyl elongation of a fatty acyl group by hydrolyzing an acyl group on a fatty acid. In plants, an acyl-ACP thioesterase terminates the acyl elongation process by hydrolysis of the acyl-ACP thioester; free fatty acid then is released from the fatty acid synthase. In *E. coli*, the long-chain acyl group is transferred directly from ACP to glycerol-3-phosphate by a glycerol-3-phosphate acyltransferase, and free fatty acids normally are not found as intermediates in lipid biosynthesis. As in most other organisms, the major end products of the plant and *E. coli* fatty acid synthase are usually 16- or 18-carbon fatty acids. Chain length is determined by the 3-ketoacyl-ACP synthases I and II and the glycerol-3-phosphate acyltransferase in *E. coli*. (Voelker and Davies, *J. Bacteriol*, 1994, 17: 7320-7327).

4-Hydroxybenzoyl-CoA Thioesterases (4-HBTs)

During the last century, large quantities of industrially produced 4-chlorobenzoate (4-CBA) or 4-CBA progenitors (herbicides and polychlorinated biphenyl pesticides) have been released into the environment (Cork, D. and Krueger, J. (1991) *Adv. Appl. Microbiol.*, 36:1-66; Furukawa, K. (1994) *Biodegradation*, 5:289-300; Haggblom, M. (1992) *FEMS Microbiol. Rev.*, 9:29-71; Higson, F. (1992) *Adv. Appl. Microbiol.*, 37:135-164; and Zhuang, Z. et al., (2003) *Applied and Environmental Microbiology*, 69: 2707-2711). Within recent years, a variety of soil-dwelling, 4-CBA-degrading microorganisms have been identified that catabolize halogenated hydrocarbons appearing in the environment and use them as the principal source of carbon (Hileman, B. (1993) *Chem. Eng. News*, 71:11-20).

The first step in the biochemical scheme, by which 4-chlorobenzoate is thioesterified with CoA, requires one molecule of $Mg^{2+}$-ATP and is catalyzed by 4-chlorobenzoyl-CoA ligase. The second step is catalyzed by 4-chlorobenzoyl-CoA dehalogenase and involves the hydrolytic substitution of a hydroxyl for a chloro group at the para-position of the aromatic ring. In the third and last step, the thioester linkage between the CoA moiety and the 4-hydroxybenzoyl group is cleaved by 4-hydroxybenzoyl-CoA thioesterase (4-HBT). The genes encoding these three enzymes are organized in an operon under the positive control of 4-chlorobenzoyl-CoA (Dunaway-Mariano, D. and Babbitt, P. (1994) *Biodegradation*, 5:259-276).

U.S. Pat. No. 5,455,167 discloses genes and constructs for expressing genes encoding higher plant acyl-ACP thioesterases, as well as a construct for expressing a gene encoding the *Vibrio harveyi* LuxD acyl transferase (YP_001448362.1 GI:156977456), belonging to Pfam PF02273, in higher plants. PCT Publication No. WO2007/136762 discloses recombinant microorganisms engineered for the fermentative production of fatty acid derivatives, such as, inter alia, fatty alcohols and wax esters, in which the host strain can express a higher plant thioesterase or the *E. coli* TesA acyl-CoA thioesterase. PCT Publication No. WO2008/100251 describes methods for engineering microorganisms that include genes encoding synthetic cellulosomes to produce hydrocarbon products (which may be, inter alia, alkanes, alkenes, alkynes, dienes, fatty acids, isoprenoids, fatty alcohols, fatty acid esters, polyhydroxyalkanoates, organic acids, or the like). The microorganism that contains one or more exogenous nucleic acid sequence encoding a synthetic cellulosome can also include an exogenous thioesterase gene, such as the *E. coli* TesA acyl-CoA thioesterase or a plant thioesterase gene, which can be expressed in the host cells.

SUMMARY

One aspect of the invention is a microorganism comprising at least one recombinant nucleic acid molecule encoding a 4-hydroxybenzoyl-CoA thioesterase (4-HBT). The microorganism can express the gene encoding the 4-hydroxybenzoyl-CoA thioesterase to facilitate the production of one or more fatty acids or fatty acid derivatives, or a combination thereof. In one embodiment of the invention, the 4-hydroxybenzoyl-CoA thioesterase hydrolyzes acyl-ACP. Preferably, but not necessarily, the microorganism is a photosynthetic microorganism.

In most embodiments of the invention, the microorganism includes a recombinant nucleic acid molecule encoding a 4-hydroxybenzoyl-CoA thioesterase and also produces at least one free fatty acid and/or fatty acid derivative in an amount greater than the amount that would be produced by the same microorganism without the recombinant nucleic acid molecule. For example, in some embodiments, the microorganism produces at least 5 mg per liter (for example at least 10 mg per liter, at least 20 mg per liter, at least 30 mg per liter, at least 40 mg per liter, or at least 50 mg per liter) of free fatty acids and/or derivatives over a period from six hours to ten days.

Additionally or alternately, the microorganism includes a recombinant nucleic acid molecule encoding a 4-hydroxybenzoyl-CoA thioesterase and can produce at least one free fatty acid and/or derivative that has an acyl chain length ranging from 8 to 24 carbons (for example, an acyl chain length from 8 to 18 carbons or an acyl chain length from 12 to 16 carbons). For example, at least one free fatty acid and/or derivative produced by such a microorganism can have an acyl chain length of 8, 10, 12, 14, 16, 18, 20, 22, and/or 24 carbons. In cases where the fatty acid derivative comprises a wax ester, the wax ester should comprise ester carbons (A carbons), as well as acyl chain carbons (B carbons). In cases where the fatty acid derivative comprises one or more compounds that do not exhibit a carbonyl group (e.g., fatty alcohols, alkanes, and alkenes), the "acyl" chain length of such compounds should be understood to correspond herein to the total number of carbons in those molecules.

Further, additionally or alternately, the microorganism includes at least one recombinant gene encoding a 4-hydroxybenzoyl-CoA thioesterase and can produce at least one fatty acid derivative such as, but not limited to, one or more fatty aldehydes, fatty alcohols, wax esters, alkanes, alkenes, and/or a combination thereof. For example, the microorganism can produce at least one fatty acid derivative having a total number of carbons from 7 to 36 (for example, from 7 to 34 or from 11 to 32 carbons). Additionally or alternately, at least one fatty acid derivative produced by the microorganism can have a total number of carbons of 7, 8, 9, 10, 11, 12, 13, 14, 15, 16, 17, 18, 19, 20, 21, 22, 23, 24, 26, 28, 30, 32, 34, and/or 36.

Still further, additionally or alternately, the microorganism includes at least one recombinant gene encoding a 4-hydroxybenzoyl-CoA thioesterase and at least 30 weight percent (for example at least 40 wt %, at least 50 wt %, or at least 60 wt %) of the free fatty acids and/or derivatives produced by the microorganism are free fatty acids having an acyl chain length of 8, 10, 12, 14, 16, and/or 18 carbons and/or fatty acid derivatives having a total number of carbons of 7, 8, 9, 10, 11, 12, 13, 14, 15, 16, 17, 18, 19, 20, 21, 22, 23, 24, 26, 28, 30, 32, 34, and/or 36.

Yet further, additionally or alternately, the microorganism includes recombinant nucleic acid molecule encoding an 4-hydroxybenzoyl-CoA thioesterase that is a member of Pfam family PF03061. Yet still further, additionally or alternately, the microorganism encodes a 4-hydroxybenzoyl-CoA thioesterase that includes Pfam domain PF03061, and the microorganism can produce a fatty acid having an acyl chain length of 8, 10, 12, 14, 16, and/or 18 carbons and/or a fatty acid derivative having a total number of carbons from 7 to 36.

Alternately or in addition, the microorganism includes at least one recombinant gene encoding a 4-hydroxybenzoyl-CoA thioesterase having at least 50% amino acid identity (for example, at least 55%, at least 60%, at least 65%, at least 70%, at least 75%, at least 80%, at least 85%, at least 90%, at least 95%, at least 96%, at least 97%, at least 98%, at least 99%, or about 100%, sequence identity) to SEQ ID NO:1 or SEQ ID NO:2. Further additionally or alternately, the microorganism can produce a fatty acid having an acyl chain length of 8, 10, 12, 14, 16, and/or 18 carbons and/or a fatty acid derivative having a total number of carbons from 7 to 36. In some embodiments, the microorganism contains a nucleic acid molecule that includes nucleotide sequence SEQ ID NO:3 or SEQ ID NO:4.

Further provided herein is an isolated or recombinant nucleic acid molecule that comprises a sequence encoding a polypeptide having an amino acid sequence that has at least 97% identity to SEQ ID NO:1. For example, an isolated or recombinant nucleic acid molecule of the invention can comprise a sequence encoding a polypeptide having an amino acid sequence having at least 97%, at least 98%, at least 99%, or about 100%, sequence identity to SEQ ID NO:1. Also provided herein is an isolated or recombinant nucleic acid molecule that comprises a sequence encoding a polypeptide that includes an amino acid sequence that has at least 70%, at least 75%, at least 80%, at least 85%, at least 90%, at least 95%, at least 96%, at least 97%, at least 98%, at least 99%, or about 100%, sequence identity to identity to SEQ ID NO:1, in which the polypeptide can hydrolyze an acyl-ACP substrate. Alternatively or in addition, the isolated or recombinant nucleic acid molecule comprises a sequence encoding a polypeptide that includes an amino acid sequence having at least 70%, at least 75%, at least 80%, at least 85%, at least 90%, at least 95%, at least 96%, at least 97%, at least 98%, at least 99%, or about 100%, sequence identity to identity to SEQ ID NO:1 and, when expressed in a host microorganism, results in production of a free fatty acid or fatty acid derivative by the host microorganism. For example, expression of a polypeptide that has a sequence with at least 70% identity to SEQ ID NO:1 can result in production of at least two fold the amount of a free fatty acid or fatty acid derivative produced by a microorganism identical to the host microorganism in all respects except that it does not express the polypeptide having an amino acid sequence at least 70% identical to SEQ ID NO:1.

Further provided herein is an isolated or recombinant nucleic acid molecule that comprises a sequence encoding a polypeptide having an amino acid sequence that has at least 70% identity to SEQ ID NO:2. For example, an isolated or recombinant nucleic acid molecule of the invention can comprise a sequence encoding a polypeptide having an amino acid sequence having at least 75%, at least 80%, at least 85%, at least 90%, at least 95%, at least 96%, at least 97%, at least 98%, at least 99%, or about 100%, sequence identity to identity to SEQ ID NO:2. Also provided herein is an isolated or recombinant nucleic acid molecule that comprises a sequence encoding a polypeptide that includes an amino acid sequence that has at least 50% identity to SEQ ID NO:2, in which the polypeptide can hydrolyze an acyl-ACP substrate. For example, the isolated or recombinant nucleic acid molecule comprises a sequence encoding a polypeptide that includes an amino acid sequence that has at least 50% identity (for example, at least 55%, at least 60%, at least 65%, at least 70%, at least 75%, at least 80%, at least 85%, at least 90%, at least 95%, at least 96%, at least 97%, at least 98%, at least 99%, or about 100% identity) to SEQ ID NO:2, in which the polypeptide can hydrolyze an acyl-ACP substrate. Alternatively or in addition, an isolated or recombinant nucleic acid molecule of the invention can comprise a sequence having at least 50% amino acid identity (for example, at least 55%, at least 60%, at least 65%, at least 70%, at least 75%, at least 80%, at least 85%, at least 90%, at least 95%, at least 96%, at least 97%, at least 98%, at least 99%, or about 100%, sequence identity) to SEQ ID NO:2 in which expression of the nucleic acid sequence in a host microorganism results in the production of at least one free fatty acid or fatty acid derivative. Expression of the polypeptide that has a sequence with at least 50% identity to SEQ ID NO:2 can result in production of at least two fold the amount of a free fatty acid or fatty acid derivative produced by a microorganism identical in all respects except that it does not express the polypeptide that includes an amino acid sequence at least 50% identical to SEQ ID NO:2.

In some embodiments, a nucleic acid molecule encoding a 4-hydroxybenzoyl-CoA thioesterase can be stably integrated into a chromosome of a microorganism. Additionally or alternately, a nucleic acid encoding a 4-hydroxybenzoyl-CoA thioesterase can be in an autonomously replicating episome. For example, a nucleic acid encoding a 4-hydroxybenzoyl-CoA thioesterase present on an episome and/or integrated into the genome of the microorganism can be an exogenous nucleic acid molecule introduced into the host microorganism (or a progenitor of the host microorganism), and can also be a recombinant nucleic acid molecule produced by genetic engineering.

Further, additionally or alternately, the genetically engineered microorganism can include an expression construct that includes the recombinant nucleic acid molecule encoding the 4-hydroxybenzoyl-CoA thioesterase and one or more additional sequences that regulate expression of the 4-hydroxybenzoyl-CoA thioesterase gene. For example, the expression construct can include a promoter operative in the host cells, where the promoter can be, for example, a bacterial, viral, phage, or eukaryotic promoter. Alternately, the promoter can be a synthetic promoter. Further, a promoter in an expression construct that includes a gene encoding a 4-hydroxybenzoyl-CoA thioesterase can be a constitutive promoter, or, in alternate embodiments, can be an inducible promoter. For example, the inducible promoter can be controlled by a metal or compound such as lactose or a lactose analogue, and/or can be controlled by light and can be, for example, a lac, tac, or trc promoter, a secA promoter, an rbc promoter, a psaAB promoter, or a psbA promoter.

Still further, additionally or alternately, the microorganism of the described invention includes a recombinant nucleic acid molecule encoding a 4-hydroxybenzoyl-CoA thioesterase and further comprises a recombinant nucleic acid molecule encoding an acetyl-CoA carboxylase enzyme and/or a recombinant nucleic acid molecule encoding a β-ketoacyl synthase (KAS). Yet further additionally or alternately, the microorganism of the described invention has attenuated/disrupted expression of one or more genes encoding acyl-ACP synthase, acyl-CoA synthase, acyl-CoA dehydrogenase, glycerol-3-phosphate dehydrogenase, acetaldehyde-CoA dehydrogenase, pyruvate dehydrogenase, or acetate kinase. For example, any of these genes can be knocked out by insertional mutagenesis and/or downregulated via RNA interference or via antisense RNA-mediated gene silencing.

The genetically engineered microorganism in any of the embodiments provided herein can be, for example, a *eubacterium*, archaebacterium, fungus, yeast, heterokont, cyanobacterium, or alga. According to some embodiments of the present invention, the host microorganism is a photosynthetic microorganism, such as a photosynthetic bacterium or alga, including a eukaryotic microalgal species. For example, the genetically modified microorganism can be a species of microalgal genus including, but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* and *Volvox.*

More particularly, the microorganism can be a prokaryotic photosynthetic microorganism. For example, the photosynthetic microorganism can be a species of cyanobacterial genus, including, but not limited to, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.*

According to another aspect, the present invention provides a culture for producing a free fatty acid and/or derivative comprising a population of microorganisms that can comprise a recombinant nucleic acid molecule encoding a 4-hydroxybenzoyl-CoA thioesterase. In certain preferred embodiments, the microorganism is a photosynthetic microorganism and the growth media of the culture does not include a reduced carbon source, or at least a substantial amount of a reduced carbon source, where a substantial amount is an amount that can support growth of the culture in the absence of another energy source.

In one preferred embodiment, the microorganisms in the culture of the present invention can produce (and optionally, but preferably, release and/or secrete) at least one free fatty acid and/or fatty acid derivative. Additionally or alternately, the microorganisms in the culture produce a greater amount of a fatty acid and/or fatty acid derivative than a culture of the same microorganisms that do not include a recombinant nucleic acid molecule encoding a 4-hydroxybenzoyl-CoA thioesterase, in which the culture is identical in other respects. Further additionally or alternately, the microorganisms in the culture includes a recombinant nucleic acid molecule encoding a 4-hydroxybenzoyl-CoA thioesterase, in which the culture can further include at least 5 mg per liter (for example at least 10 mg per liter, at least 20 mg per liter, at least 30 mg per liter, at least 40 mg per liter, or at least 50 mg per liter) of free fatty acids and/or fatty acid derivatives over a period ranging from six hours to ten days. The fatty acids and/or fatty acid derivatives can be present in the media—for example, as precipitates at or near the surface of the media, associated with the media vessel as droplets including suspended droplets (e.g., an emulsion), as a relatively immiscible layer floating on top of the aqueous culture medium, as a "scum", film, gel, semi-solid, colloid, fine particulate, particulate, solid, or aggregate that may be dispersed, suspended, or entrained within the culture medium, associated with the cells of the host microorganism, phase separated in some other fashion, or a combination thereof.

Additionally or alternately, the host microorganism can be a photosynthetic microorganism and the growth medium of the culture may not include a substantial amount of a reduced carbon source, where a substantial amount is an amount that can support growth of the culture in the absence of another energy source. Further additionally or alternately, a culture can be provided with at least one source of inorganic carbon, such as, for example, bicarbonate or carbon dioxide ($CO_2$), and/or the photosynthetic microorganisms in the culture can be exposed to light for at least a portion of the culturing period.

Additionally, a free fatty acid and/or derivative can be isolated from the culture, e.g., from the cells, the growth media, or the whole culture. For example, the isolation can be by organic extraction of whole and/or lysed cells, via removal of free fatty acids and/or derivatives as precipitates (e.g., from the upper layer of the culture media, also termed "skimming"), through the use of particulate adsorbents, bubbles, and/or matrices that can bind the fatty acids or fatty acid derivatives, or combinations thereof.

DETAILED DESCRIPTION OF THE INVENTION

Figure 1:
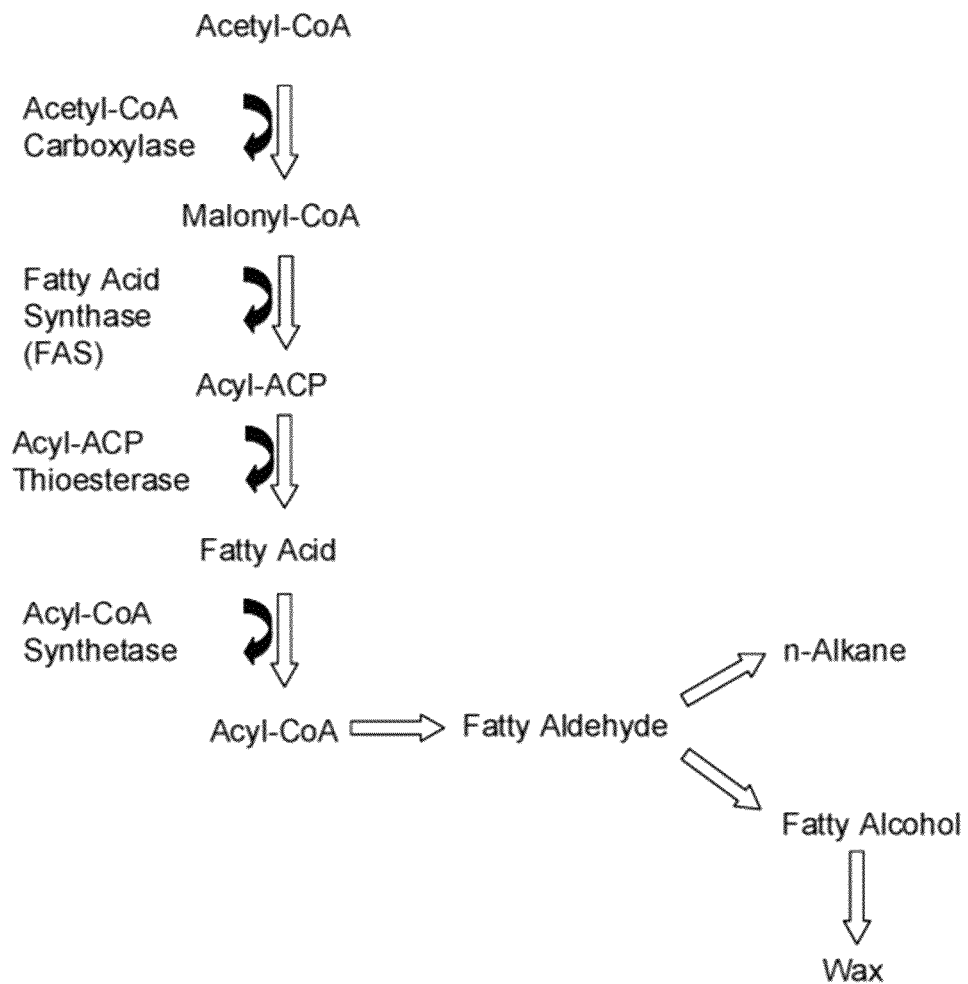
FIG. 1 shows a schematic diagram of the biosynthetic pathway for producing free fatty acids and fatty acid derivatives.

The described invention provides a composition and method for producing one or more free fatty acids and/or derivatives thereof comprising expressing 4-hydroxybenzoyl-CoA thioesterase in a microorganism (e.g., by expressing a recombinant nucleic acid molecule encoding 4-hydroxybenzoyl-CoA thioesterase).

GLOSSARY

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The phrase "conservative amino acid substitution" or "conservative mutation" as used herein refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner can include: a "charged/polar group," including Glu, Asp, Asn, Gln, Lys, Arg, and His; an "aromatic or cyclic group," including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group," comprising Lys, Arg and His; the "negatively-charged sub-group," comprising Glu and Asp; and the "polar sub-group" comprising Asn and Gln. In another example, the aromatic or cyclic group can be sub-divided into sub-groups including: the "nitrogen ring sub-group," comprising Pro, His, and Trp; and the "phenyl sub-group" comprising Phe and Tyr. In another further example, the aliphatic group can be sub-divided into sub-groups including: the "large aliphatic non-polar sub-group," comprising Val, Leu, and Ile; the "aliphatic slightly-polar sub-group," comprising Met, Ser, Thr, and Cys; and the "small-residue sub-group," comprising Gly and Ala. Examples of conservative mutations include amino acid substitutions of amino acids within the sub-groups above, such as, but not limited to:

Alanine (A), Serine (S), Threonine (T);
Aspartic Acid (D), Glutamic Acid (E);
Asparagine (N), Glutamic Acid (Q);
Arginine (R), Lysine (K);
Isoleucine (I), Leucine (L), Methionine (M), Valine (V); and
Phenylalanine (F), Tyrosine (Y), Tryptophan (W).

The term "acyl-acyl carrier protein thioesterase" or "acyl-ACP thioesterase," as used herein, refers to a thioesterase enzyme that hydrolyzes an acyl-ACP ester linkage in preference to other substrates, such as an acyl-CoA substrate and/or a hydroxybenzoyl-CoA substrate (e.g., 4-hydroxybenzoyl-CoA, 2,5-dihydroxybenzoyl-CoA, or the like), and can include an acyl-ACP thioesterase belonging to Protein family (Pfam) PF01643 (at pfam.cgb.ki.set; at pfam.janelia.org/; at pfam.sanger.ac.uk).

The terms "acyl-coenzyme A thioesterase", "acyl-CoA thioesterase", and "acyl-CoA hydrolase," as used herein, refer to a thioesterase enzyme that catalyzes the hydrolysis of the thioester bond present within acyl-CoA ester molecules to yield coenzyme A (CoASH) and the corresponding non-esterified fatty acid.

The term "attenuate," as used herein, means to weaken or reduce in force, intensity, activity, effect, or quantity.

The term "autotroph", as used herein, refers to an organism that produces complex organic compounds (carbohydrates, fats, and proteins) from simple inorganic molecules using energy from light (by photosynthesis) or inorganic chemical reactions. They are typically able to make their own food. Some autotrophs can fix carbon dioxide.

The term "autotrophic," as used herein, refers to an organism that is capable of producing complex organic compounds (carbohydrates, fats, and proteins) from simple inorganic molecules using energy from light (by photosynthesis) and/or inorganic chemical reactions. The term "photoautotrophic," as used herein, refers to an organism capable of producing complex organic compounds (carbohydrates, fats, and proteins) from simple inorganic molecules using energy from light (by photosynthesis). "Phototrophic growth" is growth using light as an energy source.

The term "biofuel," as used herein, refers to any fuel that is obtained from a renewable biological resource.

The term "carbon source," as used herein, refers to a compound that provides carbon skeletons needed for synthesis of new organic molecules.

The term "clade," as used herein, refers to a group of biological taxa or species that share features inherited from a common ancestor. A clade includes an ancestral lineage and all the descendants of that ancestor. The term clade is used also to refer to a grouping of genes or proteins by relatedness (homology) of their sequences.

A gene that is "codon-optimized" for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except for methionine and tryptophan are encoded by more than one codon. For example, arginine, leucine, and serine are encoded by six different codons; and glycine, alanine, valine, threonine, and proline are encoded by four different codons. Many organisms use certain codons to encode a particular amino acid more frequently than others. Without limiting any aspects of the invention to any particular mechanism, it is believed that some tRNAs for a given amino acid are more prevalent than others within a particular organism, and genes requiring a rare tRNA for translation of the encoded protein may be expressed at a low level due in part to a limiting amount of the rare tRNA. Thus, for adequate or optimal levels of expression of an encoded protein, a gene may be "codon-optimized" to change one or more codons to new codons ("preferred codons") that are among those used more frequently in the genes of the host organism (referred to as the "codon preference" of the organism). As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently that the original codon(s), whether or not they are used most frequently in the organism to encode a particular amino acid.

The term "controllable regulatory element" or "regulatory element," as used herein, refers to nucleic acid sequences capable of effecting the expression of the nucleic acids, or the peptide or protein product thereof. Controllable regulatory elements may be operably linked to the nucleic acids, peptides, or proteins of the present invention. The controllable regulatory elements, such as, but not limited to, control sequences, need not be contiguous with the nucleic acids, peptides, or proteins whose expression they control as long as they function to direct the expression thereof. Thus, for example, intervening untranslated yet transcribed sequences may be present between a promoter sequence and a nucleic acid of the present invention and the promoter sequence may still be considered "operably linked" to the coding sequence. Other such control sequences include, but are not limited to, enhancer sequences, sequences regulating translation, sequences regulating mRNA stability, polyadenylation signals, termination signals, and ribosome binding sites.

The term, "endogenous," as used herein, refers to substances originating or produced within an organism. An "endogenous" gene or protein is a gene or protein residing in a species that is also derived from that species.

An "episome" is a nucleic acid molecule that is not integrated into the chromosome or chromosomes of the cell and replicates autonomously in a cell. An "episomal" nucleic acid molecule or sequence is a gene, nucleic acid molecule, or nucleic acid sequence that is integrated into an episome. An example of an episome is a plasmid, which is a circular DNA molecule outside of the chromosome(s) that includes an origin of replication and replicates autonomously within the cell.

"Expression construct" refers to a nucleic acid that has been generated via human intervention, including by recombinant means or direct chemical synthesis, with a series of specified nucleic acid elements that permit transcription and/or translation of a particular nucleic acid in a host cell. The expression construct can be part of a plasmid, virus, or nucleic acid fragment.

The term "exogenous," as used herein, refers to a substance or molecule originating or produced outside of an organism.

The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant cell. An "endogenous" nucleic acid molecule, gene, or protein can represent the organism's own gene or protein as it is naturally produced by the organism.

The term "expressing" or "expression," as used herein, means the transcription and translation of a nucleic acid molecule by a cell. Expression can be, for example, constitutive or regulated, such as, by an inducible promoter (e.g., lac operon, which can be triggered by Isopropyl β-D-1-thiogalactopyranoside (IPTG)).

The term "fatty acid," as used herein, is meant to refer to a non-esterified a carboxylic acid having an alkyl chain of at least 3 carbons (that is, an acyl chain of at least 4 carbons) or its corresponding carboxylate anion, denoted as RCOOH or RCOO— respectively, where R is an alkyl chain of between 3 and 23 carbons. A "free fatty acid" is substantially unassociated, e.g., with a protein, within or outside an organism (e.g., globular and/or micellular storage within an organism, without esterification, can still qualify as a free fatty acid). Thus, a free fatty acid according to the present invention need not necessarily be a strict acid or be structurally "free", but a free fatty acid specifically does not include an acyl moiety whose carboxylate oxygen is covalently linked to any other moiety besides a hydrogen atom, meaning that fatty acid esters are specifically not included in free fatty acids. However, a free fatty acid can advantageously include an acyl moiety containing at least four carbons (for example, at least 6 carbons, for example at least 8 carbons), in which the acyl moiety (i) is covalently linked to a hydrogen atom, (ii) has an ionic charge, to which a counterion can be associated (even if loosely and/or solvent-separated), and/or (iii) is otherwise associated (not covalently) with a moiety other than hydrogen, for example, through an ester bond, such that a free fatty acid is relatively easily transformable into the corresponding acid form or the corresponding ionic form (e.g., through hydrogen-bonding or the like. Nonlimiting examples of counterions can include metals salts (such as calcium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof. The term "free fatty acids" as used herein also refers to fatty acids, which are not covalently bound to any other moiety with the exception of hydrogen (bound by the carboxylic acid group). For example, a free fatty acid is not bound to other molecules such as ACP, coenzyme A (CoA), or glycerol (for example, as part of a triglyceride, diglyceride, monoglyceride, or phospholipid molecule). Free fatty acids contain a carboxyl group (—COOH), which can be ionized into an anionic carboxylate form (R—COO$^-$; R: hydrocarbons).

Fatty acids can have an even or an odd number of carbon atoms (e.g., heptadecanoic=C17) and can also have branched chains (e.g., isopalmitic acid, anteisononadecanoic acid) or carbocyclic units (e.g., sterculic acid, chaulmoogric acid).

In some fatty acids, the hydrocarbon chain is fully saturated (meaning contains no double bonds) and unbranched; others contain one (monounsaturated) or more double bonds (unsaturated). A simplified nomenclature for these compounds specifies the chain length and number of double bonds, separated by a colon; the 16-carbon saturated palmitic acid is abbreviated 16:0, and the 18-carbon oleic acid, with one double bond, is 18:1. The positions of any double bonds are specified by superscript numbers following Δ (delta); a 20-carbon fatty acid with one double bond between C-9 and C-10 (C-1 being the carboxyl carbon), and another between C-12 and C-13, is designated 20:2 (Δ9,12), for example. The most commonly occurring fatty acids have even numbers of carbon atoms in an unbranched chain of 12 to 24 carbons. The even number of carbons results from the mode of synthesis of these compounds, which involves condensation of acetate (two-carbon) units. The position of double bonds is also regular; in most monounsaturated fatty acids, the double bond is between C-9 and C-10 ($\Delta^9$), and other double bonds of polyunsaturated fatty acids are generally $\Delta^{12}$ and $\Delta^{15}$. The double bonds of almost all naturally occurring unsaturated fatty acids are in the cis configuration. (Lehninger et al., *Principles of Biochemistry*, Vol. 1, Macmillan, 2005)

Examples of saturated fatty acids include, but are not limited to, butanoic (butyric) acid (C4), hexanoic (caproic) acid (C6), octanoic (caprylic) acid (C8), decanoic (capric) acid (C10), dodecanoic (lauric) acid (C12), tetradecanoic (myristic) acid (C14), hexadecanoic (palmitic) acid (C16), octadecanoic (stearic) acid (C18), and eicosanoic (arachidic) acid (C20), docosanoic (behenic) acid (C22), tetracosanoic (lignoceric) acid (C24). Examples of unsaturated fatty acids include, but are not limited to, myristoleic acid (C14:1, cis$^{\Delta 9}$), palmitoleic acid (C16:1, cis$^{\Delta 9}$), sapienic acid (C16:1, cis$^{\Delta 6}$), oleic acid (C18:1, cis$^{\Delta 9}$), linoleic acid (C18:2, cis$^{\Delta 9}$, cis$^{\Delta 12}$), α-linoleic acid (C18:3, cis$^{\Delta 9}$, cis$^{\Delta 12}$, CiS$^{\Delta 15}$), arachidonic acid (C20:4, cis$^{\Delta 5}$, cis$^{\Delta 8}$, cis$^{\Delta 11}$, cis$^{\Delta 14}$), eicosapentaenoic acid (C20:5, cis$^{\Delta 5}$, cis$^{\Delta 8}$, cis$^{\Delta 11}$, cis$^{\Delta 14}$, cis$^{\Delta 17}$,), erucic acid (C22:1, cis-$^{\Delta 13}$), and docosahexaenoic acid (C22:6, cis$^{\Delta 4}$, cis$^{\Delta 7}$, cis$^{\Delta 10}$, cis$^{\Delta 13}$, cis$^{\Delta 16}$, cis$^{\Delta 19}$). Long chain fatty acids also can be made from more readily available shorter chain fatty acids (C12-C18) by appropriate chain-extension procedures.

Nonlimiting examples of naturally-occurring branched-chain fatty acids include the iso fatty acids (mainly with an even number of carbon atoms) and the anteiso fatty acids (mainly with an odd number of carbon atoms), polymethyl branched acids in bacterial lipids, and phytol-based acids.

The most common cyclic acids contain a cyclopropane, cyclopropene, or cyclopentene unit. Cyclopropane acids occur in bacterial membrane phospholipids and are mainly C17 or C19 (lactobacillic) acids. The cyclopropane unit, like cis double bond, introduces a discontinuity in the molecule and increases fluidity in the membrane.

The physical properties of the fatty acids, and of compounds that contain them, are determined largely by the length and degree of unsaturation of the hydrocarbon chain. The nonpolar hydrocarbon chain accounts for the poor solubility of fatty acids in water. The longer the fatty acyl chain and the fewer the double bonds, the lower the solubility in water. The carboxylic acid group is polar (and ionized at neutral pH) and accounts for the slight solubility of short chain fatty acids in water. The melting points of fatty acids and of compounds that contain them are influenced also strongly by the length and degree of unsaturation of the hydrocarbon chain. In the fully saturated compounds, free rotation around each of the carbon-carbon bonds gives the hydrocarbon chain great flexibility; the most stable conformation is this fully extended form, in which the steric hindrance of neighboring atoms is minimized. These molecule can pack together tightly in nearly crystalline arrays, with atoms all along their lengths in van der Waals contact with the atoms of neighboring molecules. A cis double bond forces a kink in the hydrocarbon chain. Fatty acids with one or several of such kinks cannot pack together as tightly as fully saturated fatty acids and their interactions with each other are therefore weaker. Because it takes less thermal energy to disorder these poorly ordered arrays of unsaturated fatty acids, they have lower melting points than saturated fatty acids of the same chain length (Lehninger et al., *Principles of Biochemistry*, Vol. 1, Macmillan, 2005).

The term "fatty acid derivative," as used herein, refers to an organic molecule derived from a fatty acid. Examples of fatty acid derivative include, but are not limited to, C1-C5 fatty acid esters such as fatty acid methyl esters and fatty acid ethyl esters, wax esters, fatty alcohols, fatty aldehydes, alkanes, and alkenes.

The term "fatty alcohol," as used herein, refers to an alcohol made from a fatty acid or fatty acid derivative and having the formula ROH. The hydrocarbon chain of the fatty alcohol can be straight or branched. The hydrocarbon chain can be saturated or unsaturated.

The term "fatty aldehyde," as used herein, refers to an aldehyde made from a fatty acid or fatty acid derivative and having the formula RCHO. The hydrocarbon of the fatty aldehyde can be saturated or unsaturated.

The term "gene," as used herein, refers to a nucleic acid molecule that encodes a protein or functional RNA (for example, a tRNA). A gene can include regions that do not encode the final protein or RNA product, such as 5' or 3' untranslated regions, introns, ribosome binding sites, promoter or enhancer regions, or other associated and/or regulatory sequence regions.

The terms "gene expression" and "expression" are used interchangeably herein to refer to the process by which inheritable information from a gene, such as a DNA sequence, is made into a functional gene product, such as protein or RNA.

The term "genetic engineering," as used herein, refers to the use of molecular biology methods to manipulate nucleic acid sequences and introduce nucleic acid molecules into host organisms. The term "genetically engineered," as used herein, means a cell that has been subjected to recombinant DNA manipulations, such as the introduction of exogenous nucleic acid molecule, resulting in a cell that is in a form not found originally in nature.

The term "growth," as used herein, refers to a process of becoming larger, longer or more numerous, or can indicate an increase in size, number, or volume of cells in a cell population.

The term "heterotrophic," as used herein, refers to requiring reduced carbon substrates for growth.

The term "heterotroph," as used herein, refers to an organism that does not produce its own food and must acquire some of its nutrients from the environment, e.g., in the form of reduced carbon.

A "homolog" of a gene or protein refers to its functional equivalent in another species.

The term "hydrocarbon," as used herein, refers to any of the organic compounds made up exclusively of hydrogen and carbon in various ratios.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed.

The terms "4-hydroxybenzoyl-CoA thioesterase", "hydroxybenzoyl-CoA thioesterase", "4-hydroxybenzoate thioesterase", and "4-HBT," as used herein, refer to a thioesterase enzyme (EC 3.1.2.23) that can catalyze the cleavage of the thioester bond of 4-hydroxybenzoyl-CoA to form hydroxybenzoate, the last of the three steps in the pathway converting 4-chlorobenzoate to hydroxybenzoate.

The term "inducer," as used herein, refers to a molecule that can initiate the transcription of a gene, which is controlled by a inducible promoter.

The term "inducible promoter," as used herein, refers to a promoter, whose activity in promoting transcription of a gene to which it is operably linked is controlled by an environmental condition (e.g., temperature, light, or the like) or the presence of a factor such as a specific compound or biomolecule. The term "constitutive promoter" refers to a promoter whose activity is maintained at a relatively constant level in all cells of an organism with little or no regard to cell environmental conditions (as the concentration of a substrate).

The terms "inhibiting", "inhibit," and "inhibition," as used herein, refer to reducing the amount or rate of a process, to stopping the process entirely, or to decreasing, limiting, or blocking the action or function thereof. Inhibition may include a reduction or decrease of the amount, rate, action function, or process by at least 5%, for example at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%, when compared to a reference substance, wherein the reference substance is a substance that is not inhibited.

"Inorganic carbon" is a carbon-containing compound or molecule that cannot be used as an energy source by an organism. Typically "inorganic carbon" is in the form of $CO_2$ (carbon dioxide), carbonic acid, bicarbonate, or carbonate, which cannot be further oxidized for energy or used as a source of reducing power by organisms.

The term "insertional mutagenesis," as used herein, refers to a mutagenesis of DNA by the insertion of exogenous DNA into a gene.

The term "isolate," as used herein, refers to a process of obtaining a substance, molecule, protein, peptide, nucleic acid, or antibody that is substantially free of other substances with which it is ordinarily found in nature or in vivo systems to an extent practical and appropriate for its intended use.

The term "isolated" refers to a material, such as a nucleic acid, a peptide, or a protein, which is: (1) substantially or essentially free from components that normally accompany or interact with it as found in its naturally occurring environment, or (2) if the material is in its natural environment, the material has been synthetically (non-naturally) altered by deliberate human intervention to a composition and/or placed at a location in the cell (e.g., genome or subcellular organelle) not native to a material found in that environment. The term "substantially or essentially free" is used to refer to a material, which is at least 80% free, for example at least 90% free, at least 95% free, or at least 99% free (with percentages being weight percentages only when applicable) from components that normally accompany or interact with it as found in its naturally occurring environment. The isolated material optionally comprises material not found with the material in its natural environment.

The term "heterologous," as used herein, refers to nucleic acids derived from a different species than that into which they are introduced or than they reside in through genetic engineering of the organism or its ancestor. A heterologous protein is derived from a species other than that is produced in or introduced into. A heterologous nucleic acid sequence, gene, or protein, is a nucleic acid sequence, gene, or protein derived from an organism other than that it is introduced into or resides in.

When referring to gene regulatory elements, "heterologous" refers to a gene regulatory element that is operably linked to a gene with which it is not associated in nature. The term "heterologous expression," as used herein, means that a heterologous nucleic acid encoding a protein (e.g., an enzyme) is put into a cell that does not normally make (i.e., express) that protein.

The term "lactose analogue," as used herein, refers to a compound used as a substitute for lactose, wherein the glucose moiety of lactose is replaced by another chemical group. Examples of a lactose analogue include, but are not limited to, isopropyl-β-D-thio-galactoside (IPTG), phenyl-3-D-galactose (phenyl-Gal), and allolactose.

The term "lipid," as used herein, refers to a chemically diverse group of compounds, the common and defining feature being their insolubility in water.

The term "metabolic engineering," as used herein, generally refers to the targeted and purposeful alteration of metabolic pathways found in an organism in order to better understand and utilize cellular pathways for chemical transformation, energy transduction, and supramolecular assembly.

The term "metabolic intermediate," as used herein, refers to a precursor molecule produced by a series of enzymatic reactions, which is altered by the subsequent enzymatic reactions.

The term "microorganism" refers to a living organism so small in size that it is only visible with the aid of a microscope.

The term "mixotrophic," as used herein, refers to cells or organisms capable of using a mix of different sources of energy and carbon, for example, using phototrophy (meaning growth using energy from light) and chemotrophy (meaning growth using energy by the oxidation of electron donors), or between chemical autotrophy and heterotrophy.

The term "nucleic acid," as used herein, refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide," as used herein, refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The term "operably linked," as used herein, refers to a functional linkage between a genetic regulatory element or region and a second nucleic acid sequence, wherein the genetic regulatory element or region promotes, inhibits, terminates, initiates, or mediates transcription, translation, turnover, processing, or transport, of the nucleic acid sequence corresponding to the second sequence.

The term "origin of replication," as used herein, refers to a particular sequence in a genome, chromosome, or episome at which replication of DNA is initiated.

The term "open reading frame," as used herein, refers to a sequence of nucleotides in a DNA molecule that encodes a sequence of amino acids uninterrupted by a stop codon that has the potential to encode at least a portion of a peptide or protein. A complete open reading frame starts with a start codon (typically ATG), is followed by a string of codons each of which encodes an amino acid, and ends with a stop codon (TAA, TAG or TGA). Open reading frames often can be confirmed by matching their sequences to a database of sequenced genes or expressed sequence tags (ESTs).

The term "overexpressed," as used herein, refers to increased quantity of a gene or gene product relative to a quantity of the gene or gene product under normal conditions.

The term "peptide," as used herein, refers to a biopolymer formed from the linking together, in a defined order, of amino acids. The link between one amino acid residue and the next is known as an amide or peptide bond. The term "polypeptide," as used herein, refers to a single chain of amino acids, and a "protein" refers to one or more polypeptides. The terms polypeptide, peptide, and protein are also inclusive of modifications including, but not limited to, glycosylation, lipid attachment, sulfation, gamma-carboxylation of glutamic acid residues, hydroxylation and ADP-ribosylation. Polypeptides may not be entirely linear. For instance, polypeptides may be branched as a result of ubiquitination, and they may be circular, with or without branching, generally as a result of posttranslational events, including natural processing event and events brought about by human manipulation which do not occur naturally.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr/. The latest release of Pfam is Pfam 24.0 (October 2009, 11912 families) based on the UniProt protein database release 15.6, a composite of Swiss-Prot release 57.6 and TrEMBL release 40.6. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. All identified sequences belonging to the family are then used to automatically generate a full alignment for the family (Sonnhammer et al. (1998) *Nucleic Acids Research* 26: 320-322; Bateman et al. (2000) *Nucleic Acids Research* 26: 263-266; Bateman et al. (2004) *Nucleic Acids Research* 32, Database Issue: D138-D141; Finn et al. (2006) *Nucleic Acids Research* Database Issue 34: D247-251; Finn et al. (2010) *Nucleic Acids Research* Database Issue 38: D211-222). By accessing the pfam database, for example, using any of the above-reference websites, protein sequences can be queried against the hidden Markov models (HMMs) using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. The term "gathering threshold (GA)" or "gathering cut-off," as used herein, refers to a search threshold value used to build a full alignment. The gathering threshold is the minimum score that a sequence must attain in order to belong the full alignment of a Pfam entry. The gathering threshold for the 4-hydroxybenzoyl-CoA thioesterase family (PF03061) is 20.6. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

The term "phototroph," as used herein, refers to an organism which uses sunlight as its primary energy source. "Phototrophic" growth or culture means growth or culture in which the organisms use light, and not organic molecules, for energy.

The term "photosynthetic microorganism," as used herein, includes, but is not limited to, all algae, microalgae, and photosynthetic bacteria, which can grow phototrophically.

The term "plasmid," as used herein, refers to a DNA molecule that is separate from, and can replicate independently of, the chromosomal DNA of a cell. It is double stranded and, in many cases, circular.

The term "polypeptide" is used herein to refer to a peptide containing from about 10 to more than about 1000 amino acids.

The term "polynucleotide" or "nucleic acid molecule" refers to a deoxyribopolynucleotide, ribopolynucleotide, or an analog thereof that has the essential nature of a natural deoxyribopolynucleotide or ribonucleotide in that it hybridizes, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes are known to those of skill in the art. The term polynucleotide, as it is employed herein, embraces such chemically, enzymatically or metabolically modified forms of polynucleotides, as well as the chemical forms of DNA and RNA characteristic of viruses and cells, including among other things, simple and complex cells.

The term "primer" refers to a nucleic acid molecule which, when hybridized to a strand of DNA or RNA, is capable of serving as the substrate to which nucleotides are added in the synthesis of an extension product in the presence of a suitable polymerization agent (e.g., a DNA polymerase). In some cases, the primer is sufficiently long to uniquely hybridize to a specific region of a DNA or RNA strand.

The term "promoter," as used herein, refers to a region of DNA proximal to the start site of transcription, which is involved in recognition and binding of RNA polymerase and other proteins to initiate transcription. A given promoter may work in concert with other regulatory regions (enhancers, silencers, boundary elements/insulators) in order to direct the level of transcription of a given gene.

The term "lac promoter," as used herein, refers to a promoter of the lac operon, whose transcription activity is repressed by a repressor protein (i.e., the LacI protein encoded by the lacI gene) but relieved by an inducer, such as, lactose or analogues thereof (e.g., isopropyl-β-D-thiogalactoside (IPTG)). The inducer binds to the repressor protein and prevents it from repressing gene transcription.

The term "tac promoter," as used herein, refers to a strong hybrid promoter composed of the position −35 region of the trp promoter and the position −10 region of the lacIq5 promoter/operator. Expression of the tac promoter is repressed by the LacI protein. The lacIq allele is a promoter mutation that increases the intracellular concentration of the LacI repressor, resulting in strong repression of tac promoter. The transcriptional activity of the tac promoter is controlled by a lactose or analogues thereof.

The term "trc promoter," as used herein, refers to a hybrid promoter sequence of the lac and trp promoters. The transcriptional activity of the trc promoter also is controlled by lactose or analogues thereof. One example of a trc promoter is the trcY promoter (5'-CTGAAATGAGCTGTTGACAATTAATCATCCGGCTCGTAT AATGTGTGGAATTGTGAGCGGATAACAATTTCACACTAAGGAGGAAAAAAA-3'; SEQ ID NO:52).

The term "recombination," as used herein, refers to the process by which pieces of DNA are broken apart and recombined. The term "homologous recombination," as used herein, refers to a type of genetic recombination in which nucleotide sequences are exchanged between two similar or identical molecules of DNA.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of an exogenous or recombinant nucleic acid sequence into the organism, and includes organisms having gene knockouts, targeted mutations and gene replacement, promoter replacement, deletion, or insertion, as well as organisms having exogenous genes that have been introduced into the organism. An exogenous or recombinant nucleic acid molecule can be integrated into the recombinant/genetically engineered organism's genome or in other instances may not be integrated into the recombinant/genetically engineered organism's genome.

The term "recombinant protein," as used herein, refers to a protein produced by genetic engineering.

The term "recombinase," as used herein, refers to an enzyme that catalyzes genetic recombination.

"Reduced carbon" or a "reduced carbon compound" or "reduced carbon source" refers to a carbon-based molecule that includes carbon and hydrogen and can be used as an energy source by an organism, either through oxidation or glycolysis. Non-limiting examples of reduced carbon are sugars (including polysaccharides and starch), alcohols (including glycerol and sugar alcohols), forms of organic acids (e.g., acetate, citrate, succinate, etc.), amino acids, proteins, lipids, and fatty acids. Reduced carbon is sometimes referred to as "organic carbon."

The term "regulatory sequence" (also referred to as a "regulatory region" or "regulatory element") refers to a promoter, enhancer, 5' untranslated region, 3' untranslated region, ribosome binding site, or other segment of DNA or RNA that regulate expression of a proximal gene.

The terms "amino acid residue" and "amino acid" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, for example at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA,* 1989, 89: 10915).

In addition to calculating percent sequence identity, the BLAST algorithm also performs a statistical analysis of the similarity between two sequences (see, e.g., Karlin & Altschul, *Proc. Natl. Acad. Sci. USA,* 1993, 90: 5873-5787). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.,* 1993, 17:149-163) and XNU (Claverie and States, *Comput. Chem.*, 1993, 17:191-201) low-complexity filters may be employed alone or in combination.

As used herein, "sequence identity" or "identity" in the context of two nucleic acid or polypeptide sequences refers to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g., charge and/or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 1988, 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise stated, % homology of a sequence is across the entire length of the query sequence (the comparison window).

The term "substantial identity" of polynucleotide sequences means that a polynucleotide comprises a sequence that has at least 70% sequence identity, for example at least 80% sequence identity, at least 85% sequence identity, at least 90% sequence identity, at least 95% sequence identity, at least 96% sequence identity, at least 97% sequence identity, at least 98% sequence identity, or at least 99% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, for example at least 70%, at least 80%, at least 85%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, for example at least 80%, at least 85%, at least 90%, at least 95%, at least 96%, at least 97%, at least 98%, or at least 99% sequence identity to the reference sequence, over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

A "variant" of a gene or nucleic acid sequence is a sequence having at least 65% identity with the referenced gene or nucleic acid sequence, and can include one or more base deletions, additions, or substitutions with respect to the referenced sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" of the original sequence.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

A "conservative variant" of a polypeptide is a polypeptide having one or more conservative amino acid substitutions with respect to the reference polypeptide, in which the activity, substrate affinity, binding affinity of the polypeptide does not substantially differ from that of the reference polypeptide.

A skilled artisan likewise can produce polypeptide variants having single or multiple amino acid substitutions, deletions, additions, and/or replacements. These variants may include, inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (e) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "specifically hybridizes," as used herein, refers to the process whereby a nucleic acid distinctively or definitively forms base pairs with complementary regions of at least one strand of the nucleic acid target sequence that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 85% sequence identity, at least 90% sequence identity, at least 95% sequence identity, at least 96% sequence identity, at least 97% sequence identity, at least 98% sequence identity, at least 99% sequence identity, or about 100% sequence identity (i.e., complementary) with each other.

The term "stably integrated," as used herein, means that an exogenous or heterologous genetic material is integrated into a host genome and is inherited by the descendants of the cell.

The term "thioesterase (TE)" or "thioester hydrolase," as used herein, refers to a large enzyme group whose members hydrolyze the thioester bond between a carbonyl group and a sulfur atom. They are classified by the Nomenclature Committee of the International Union of Biochemistry and Molecular Biology (NC-IUBMB) into EC (enzyme commission) 3.1.2.1 to EC 3.1.2.27, as well as EC 3.1.2.—for unclassified TEs. Substrates of 15 of these 27 groupings contain coenzyme A (CoA), two contain acyl carrier proteins (ACPs), four have glutathione or its derivatives, one has ubiquitin, and two contain other moieties. In addition, three groupings have been deleted (Cantu et al. (2010) *Protein Science*, 19:1281-1295).

The term "triacylglycerol" or "triglycerides," as used herein, refers to a class of compounds that consist of glycerol (a three carbon trihydroxy alcohol) with a fatty acid linked to each of the three OH groups by an ester bond.

The term "transit peptide," as used herein, refers to a peptide sequence, often at the N-terminus of a precursor protein, which directs a gene product to its specific cellular destination, such as plastid.

The term "underexpressed," as used herein, refers to decreased quantity of a gene or gene product relative to the quantity of a gene or gene product under normal conditions.

The term "vector" is used herein to refer to any agent that acts as a carrier or transporter, such as a phage, plasmid, cosmid, bacmid, phage or virus, to which another genetic sequence or element (either DNA or RNA) may be attached so that sequence or element can be conveyed into a host cell.

The term "expression vector," as used herein, generally refers to a nucleic acid molecule that has been constructed in such as way that, after insertion of a DNA molecule, its coding sequence is properly transcribed into an RNA molecule and the RNA molecule can be optionally translated into a protein. The nucleic acid construct, which can be a vector, frequently is engineered to contain regulatory sequences that act as enhancer and promoter regions, which lead to efficient transcription of the open reading frame carried on the expression vector.

The "Uniprot," or Universal Protein Resource protein database, includes a comprehensive protein databases that draws from Swiss-Prot, TrEMBL (translated EMBL nucleotide sequence data library), and the Protein Sequence Database. Protein sequences can be searched against the Uniprot database at uniprot.org.

The term "wax" or "wax esters," as used herein, refers to esters of long chain fatty acids and monohydric straight chain aliphatic alcohols, which form solids or pliable substances under an identified set of physical conditions.

The term "wild type," as used herein, refers to an organism or phenotype as found in nature.

I. Genetically Engineered Microorganism for Producing Free Fatty Acids and/or Derivatives The described invention provides microorganisms comprising recombinant nucleic acid molecules encoding 4-hydroxybenzoyl-CoA thioesterases (4-HBTs) used for producing free fatty acids and/or free fatty acid derivatives. 4-hydroxybenzoyl-CoA thioesterase genes were identified by a functional screen for increased production of free fatty acids and validated by a specific biochemical assay using acyl-ACP as a substrate. The 4-hydroxybenzoyl-CoA thioesterase family is designated as PF03061 by the Pfam bioinformatics annotated database of protein families (Bateman et al. (2000) *Nucleic Acids Research* 28:263-266; Bateman et al. (2006) *Nucleic Acids Research* 32:D138-D141, Finn et al. (2010) *Nucleic Acids Research* 38:D211-222). Prokaryotic thioesterases expressed in a photosynthetic microorganism as provided herein may have the Enzyme Commission (EC) designation EC 3.1.2.23.

The superfamily of 4-hydroxybenzoyl-CoA thioesterases has been annotated previously in the public database for their hydrolyzing activity toward 4-hydroxybenzoyl-CoA. Based on bioinformatic analysis, biochemical characterization, and expression of identified sequences in microorganisms, the described invention provides that 4-hydroxybenzoyl-CoA thioesterase enzymes also possess hydrolyzing activity toward acyl-ACP substrates and therefore can be used for producing free fatty acids and/or derivatives in microorganisms.

According to one aspect, the present invention provides a microorganism that includes a recombinant nucleic acid molecule that comprises a sequence encoding an 4-hydroxybenzoyl-CoA thioesterase. The genetically engineered microorganism can produce at least one free fatty acid and/or fatty acid derivative. The 4-hydroxybenzoyl-CoA thioesterase, when expressed in a microorganism, can hydrolyze an acyl-ACP molecule.

Additionally or alternately, the amount of at least one free fatty acid and/or fatty acid derivative produced by the genetically engineered microorganism can be at least twice the amount of the free fatty acid and/or fatty acid derivative produced by the same microorganism that does not include an exogenous 4-hydroxybenzoyl-CoA thioesterase gene. For example, the photosynthetic microorganism that includes the recombinant nucleic acid molecule that encodes the 4-hydroxybenzoyl-CoA thioesterase can produce at least 30 mg per liter, for example at least 40 mg per liter or at least 50 mg per liter, of free fatty acids and/or derivatives. For example, the host microorganism can express the thioesterase such that one or more fatty acids and/or fatty acid derivates can be produced.

The genetically engineered microorganism can be any microorganism, including, but not limited to, a heterokonts (including thraustochytrids), fungus, bacterium, microalga, or cyanobacterium. Examples of suitable microbial hosts for use with the disclosed invention include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, and *Saccharomyces*. Examples of particular thraustochytrid hosts include but are not limited to *Schizochytrium* sp. and *Thraustochytrium* sp.

The genetically engineered host organism can additionally or alternately be a photosynthetic microorganism, such as, a microalga. Representative eukaryotic algae that can be useful as host organisms can include, but are not limited to, green algae (chlorophytes), red algae (rhodophytes), diatoms (bacillariophytes), prasinophytes, glaucophytes, chlorarachniophytes, euglenophytes, chromophytes, and dinoflagellates. Non-limiting examples of a microalgal genus that can contain an exogenous nucleic acid molecule encoding a prokaryotic acyl-ACP thioesterase include, but are not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochtysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, and *Volvox*.

Alternately, the microorganism can be a cyanobacterial species. Non-limiting examples of a cyanobacterial genus that can include an exogenous nucleic acid molecule encoding a 4-hydroxybenzoyl-CoA thioesterase include, but are not limited to, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus*. For example, the photosynthetic microorganism can be a *Synechococcus, Synechocystis,* or *Thermosynechococcus* species. Alternatively, the microorganism can be a *Cyanobium, Cyanothece,* or *Cyanobacterium* species, or further alternatively, the microorganism can be a *Gloeobacter, Lyngbya* or *Leptolyngba* species.

The 4-hydroxybenzoyl-CoA thioesterase gene can be any 4-hydroxybenzoyl-CoA thioesterase gene that, when expressed in the microorganism, can result in the production of free fatty acids and/or derivatives by the microorganism. 4-hydroxybenzoyl-CoA thioesterases considered useful herein can include members of the 4-hydroxybenzoyl-CoA thioesterase family (e.g., PF03061; see pfam.cgb.ki.se/ or pfam.janelia.org/ or pfam.sanger.ac.uk/) that, when queried against the Pfam bioinformatics annotated database of protein families, can demonstrate a match with the Pfam 4-hydroxybenzoyl-CoA thioesterase family (PF03061) with a bit score higher than the threshold gathering score (for example, a bit score higher than 20.6), and/or can demonstrate a Pfam-A match with the Pfam 4-hydroxybenzoyl-CoA thioesterase family with an expectation value (e value) of less than 0.01 (Bateman et al. (2000) *Nucleic Acids Research* 28:263-266; Bateman et al. (2006) *Nucleic Acids Research* 32:D138-D141, Finn et al. (2010) *Nucleic Acids Research* 38:D211-222). 4-hydroxybenzoyl-CoA thioesterases expressed in a photosynthetic microorganism as provided herein may have the Enzyme Commission (EC) designation EC 3.1.2.23.

The present invention further relates to microorganisms that include nucleic acid molecules encoding variants of 4-hydroxybenzoyl-CoA thioesterases, e.g., in which the variants have at least 70% identity, for example at least 75%, at least 80%, at least 85%, at least 90%, at least 95%, at least 96%, at least 97%, at least 98%, at least 99%, or about 100% identity, to the amino acid sequences accessed by Genbank Accession Numbers, such as those provided herein, in which the variants possess the acyl-ACP hydrolyzing activity, and expression of the variant in a microorganism can result in production of a free fatty acid and/or derivative in an amount greater than (for example at least twice as much as) that produced by a microorganism that does not include the nucleic acid molecule that encodes the 4-hydroxybenzoyl-CoA thioesterase. Sequence-structure-function relationships for thioesterases have been advanced significantly in recent years (see, for example, Dillon and Bateman, *BMC Bioinformatics* 2004, 5:109; Mayer and Shanklin, *J. Biological Chem.*, 2005, 280: 3621-3627; Mayer and Shanklin, *BMC Plant Biology*, 2007, 7:1).

Additionally or alternately, the genetically engineered microorganism that includes a nucleic acid molecule encoding an 4-hydroxybenzoyl-CoA thioesterase can produce at least one free fatty acid having an acyl chain length of 8 carbons, of 10 carbons, of 12 carbons, of 14 carbons, of 16 carbons, of 18 carbons, of 20 carbons, of 22 carbons, and/or of 24 carbons. Further additionally or alternately, the genetically engineered microorganisms can produce at least one free fatty acid having an acyl chain length from 8 to 18 carbons, for example from 12 to 16 carbons.

While 4-hydroxybenzoyl-CoA thioesterases are known for their activity hydrolyzing 4-hydroxybenzoyl-CoA substrates, as disclosed in the Examples herein, it is now demonstrated that 4-hydroxybenzoyl-CoA thioesterases are also capable of hydrolyzing acyl-ACP substrates having a plurality of different acyl chain lengths. For example, the invention contemplates the use of 4-hydroxybenzoyl-CoA thioesterases that may have substrate preferences for one or more acyl-ACP substrates having acyl chain lengths of 8, 10, 12, 14, 16, 18, 20, 22, and/or 24 carbons. Additionally or alternately, a 4-hydroxybenzoyl-CoA thioesterase can hydrolyze one or more acyl-acyl carrier protein (ACP) substrates having an acyl chain length from 8 to 18 carbons, for example from 12 to 16 carbons. Further additionally or alternately, a 4-hydroxybenzoyl-CoA thioesterase of the present invention can, in some embodiments, have its highest level of activity on an acyl-ACP substrate having an acyl chain length of 8, 10, 12, 14, 16, and/or 18 carbons.

In some embodiments, the microorganism with the recombinant gene expressing a 4-hydroxybenzoyl-CoA thioesterase can produce predominantly free fatty acids having acyl chain lengths of 8, 10, 12, 14, 16 and/or 18 carbons and/or fatty acid derivatives having a total carbon number of 8, 10, 12, 14, 16, 18, 20, 22, 24, 26, 28, 30, 32, 34, and/or 36 carbons. Additionally or alternatively, at least 30 wt %, for example at least 40 wt %, at least 50 wt %, at least 60 wt %, at least 70 wt %, at least 80 wt %, at least 90 wt %, or at least 95 wt %, of the free fatty acids produced by a genetically engineered microorganism as disclosed herein can be fatty acids having an acyl chain length of 8, 10, 12, 14, 16, and/or 18 carbons and/or fatty acid derivatives having a total carbon number of 8, 10, 12, 14, 16, 18, 20, 22, 24, 26, 28, 30, 32, 34 and/or 36 carbons. One or more free fatty acids or fatty acid derivatives produced by the genetically engineered microorganism may be saturated or may have one or more double bonds.

In some embodiments, the genetically engineered microorganism expressing a 4-hydroxybenzoyl-CoA thioesterase can produce free fatty acids and/or fatty acid derivatives of more than one acyl chain length, for example, any combination of two or more, having acyl chain lengths of 8, 10, 12, 14, 16, 18, 20, 22, and/or 24 carbons. In one such embodiment, at least 50 wt %, for example at least 60 wt %, at least 70 wt %, at least 80 wt %, at least 90 wt %, or at least 95 wt %, of the free fatty acids and/or derivatives produced by a genetically engineered microorganism as disclosed herein can have acyl chain lengths of 8, 10, 12, 14, 16, 18, 20, and/or 24 carbons. Additionally or alternatively in such embodiments, at least 50 wt %, for example at least 60 wt %, at least 70 wt %, at least 80 wt %, at least 90 wt %, or at least 95 wt %, of the free fatty acids produced by a genetically engineered microorganism as disclosed herein can be: C8 and C24 fatty acids, C8 and C22 fatty acids, C8 and C20 fatty acids, C8 and C18 fatty acids, C8 and C16 fatty acids, C8 and C14 fatty acids, C8 and C12 fatty acids, or C8 and C10. fatty acids; C10 and C24 fatty acids, C10 and C22 fatty acids, C10 and C20 fatty acids, C10 and C18 fatty acids, C10 and C16 fatty acids, C10 and C14 fatty acids, or C10 and C12 fatty acids; C12 and C24 fatty acids, C12 and C22 fatty acids, C12 and C20 fatty acids, C12 and C18 fatty acids, C12 and C16 fatty acids, or C12 and C14 fatty acids; C14 and C24 fatty acids, C14 and C22 fatty acids, C14 and C20 fatty acids, C14 and C18 fatty acids, or C14 and C16 fatty acids; C16 and C24 fatty acids, C16 and C22 fatty acids, C16 and C20 fatty acids, and C16 and C18 fatty acids; or the like.

Alternatively or in addition, the genetically engineered microorganism can include a nucleic acid molecule encoding a 4-hydroxybenzoyl-CoA thioesterase having an amino acid sequence that has at least 70% identity, for example at least 75%, at least 80%, at least 85%, at least 90%, or at least 95% identity, with SEQ ID NO:1, and the microorganism can produce a fatty acid having an acyl chain length of 8, 10, 12, 14, 16, and/or 18 carbons (optionally with at least 50 wt % of the fatty acids produced having an acyl chain length from 8 to 18 carbons) and/or a fatty acid derivative having a total number of carbons from 7 to 36 (for example from 7 to 32; from 11 to 30; and/or of 7, 8, 9, 10, 11, 12, 13, 14, 15, 16, 17, 18, 20, 22, 24, 26, 28, 30, 32, 34, and/or 36 carbons).

Non-limiting examples of thioesterases having at least 85% identity to SEQ ID NO:1 include: *Bacillus licheniformis* (DSM 13) putative thioesterase YneP (SEQ ID NO:6) having Genbank Accession Number AAU23580 and GenInfo Identifier GI: 52003638; *Bacillus subtilis* (subsp. *natto* BEST195) hypothetical protein BSNT_02984 (SEQ ID NO:7) having Genbank Accession Number BAI85489 and GenInfo Identifier GI: 291484414; *Bacillus subtilis* uncharacterized protein yneP (SEQ ID NO:8) having Genbank Accession Number Q45061 and GenInfo Identifier GI: 257096998; *Bacillus subtilis* (subsp. *spizizenii* str. W23) putative acyl-CoA thioesterase (SEQ ID NO:9) having Genbank Accession Number YP_003866210 and GenInfo Identifier GI:305674538; *Bacillus amyloliquefaciens* DSM7 putative acyl-CoA thioesterase (SEQ ID NO:10) having Genbank Accession Number YP_003920487 and GenInfo Identifier GI:308173782; *Bacillus amyloliquefaciens* FZB42 YneP (SEQ ID NO:11) having Genbank Accession Number YP_001421379 and GenInfo Identifer GI:154686218; *Bacillus subtilis* subsp. *subtilis* str. 168 YneP (SEQ ID NO:12) having Genbank Accession Number CAA97601 and GenInfo Identifier GI:1405456; *Bacillus atrophaeus* 1942 putative acyl-CoA thioesterase (SEQ ID NO:13) having Genbank Accession Number ADP32363 and GenInfo Identifier GI:310868888; *Bacillus pumilus* ATCC 7061 YneP (SEQ ID NO:14) having Genbank Accession Number ZP_03053441 and GenInfo Identifier GI:194014824; *Bacillus pumilus* SAFR-0324-hydroxybenzoyl-CoA thioesterase (SEQ ID NO:15) having Genbank Accession Number YP_001486942 and GenInfo Identifier GI:157692480; *Bacillus* sp. SG-1 hypothetical protein BSG1_15910 (SEQ ID NO:16) having Genbank Accession Number ZP_01858961 and GenInfo Identifier GI:149180457; *Bacillus megaterium* DSM 319 thioesterase family protein (SEQ ID NO:17) having Genbank Accession Number YP_003597734 and GenInfo Identifier GI:295704659; *Bacillus megaterium* QM B1551 thioesterase family protein (SEQ ID NO:18) having Genbank Accession Number YP_003563005 and GenInfo Identifier GI:294499305; *Bacillus coagulans* 36D1 thioesterase superfamily protein (SEQ ID NO:19) having Genbank Accession Number ZP_04433271 and GenInfo Identifier GI:229544212; *Geobacillus thermoglucosidasius* C56-YS93 thioesterase superfamily protein (SEQ ID NO:20) having Genbank Accession Number ZP_06810002 and GenInfo Identifier GI:295400022; *Geobacillus* sp. C56-T3 thioesterase superfamily protein (SEQ ID NO:21) having Genbank Accession Number ADI26934 and GenInfo Identifier GI:297253488; *Geobacillus* sp. Y412MC61 thioesterase superfamily protein (SEQ ID NO:22) having Genbank Accession Number ACX79004 and GenInfo Identifier GI:261376261; *Geobacillus* sp. WCH70 thioesterase superfamily protein (SEQ ID NO:23) having Genbank Accession Number YP_002949888 and GenInfo Identifier GI:239827264; *Geobacillus kaustophilus* HTA426 hypothetical protein GK1562 (SEQ ID NO:24) having Genbank Accession Number YP_147415 and GenInfo Identifier GI:56420097; *Geobacillus* sp. G11MC16 thioesterase superfamily protein (SEQ ID NO:25) having Genbank Accession Number ZP_03147050 and GenInfo Identifier GI:196248349; *Geobacillus thermodenitrificans* NG80-24-hydroxybenzoyl-CoA thioesterase-like protein (SEQ ID NO:26) having Genbank Accession Number YP_001125525 and GenInfo Identifier GI:138895072; and *Bacillus* sp. NRRL B-14911 hypothetical protein B14911_12282 (SEQ ID NO:27) having Genbank Accession Number ZP_01171315 and GenInfo Identifier GI:89098431.

Further additionally or alternatively, a genetically engineered microorganism can include a nucleic acid molecule encoding a 4-hydroxybenzoyl-CoA thioesterase having an amino acid sequence that has at least 70% identity, for example at least 75%, at least 80%, at least 85%, at least 90%, or at least 95% identity, with SEQ ID NO:2, and the microorganism can produce a free fatty acid having an acyl chain length of 8, 10, 12, 14, 16, and/or 18 carbons (for example having an acyl chain length of 8, 12, 16, and/or 18 carbons and/or optionally with at least 50 wt % of the fatty acids produced having an acyl chain length from 12 to 16 carbons) and/or a fatty acid derivative having a total number of carbons from 7 to 36 (for example from 7 to 32; from 11 to 30; and/or of 7, 8, 9, 10, 11, 12, 13, 14, 15, 16, 17, 18, 20, 22, 24, 26, 28, 30, 32, 34, and/or 36 carbons).

Non-limiting examples of thioesterases having at least 30% identity to SEQ ID NO:2 include: *Magnetospirillum magneticum* AMB-1 thioesterase (SEQ ID NO:28) having Genbank Accession Number YP_422578 and GenInfo Identifier GI:83312314; *Magnetospirillum magnetotacticum* MS-1 COG0824: Predicted thioesterase (SEQ ID NO:29) having Genbank Accession Number ZP_00055337 and GenInfo Identifier GI: 23015565; *Burkholderia cenocepacia* MC0-3 tol-pal system-associated acyl-CoA thioesterase (SEQ ID NO:30) having Genbank Accession Number ACA89951 and GenInfo Identifier GI: 169815368; *Rhodopseudomonas palustris* BisA534-hydroxybenzoyl-CoA thioesterase (SEQ ID NO:31) having Genbank Accession Number YP_782882 and GenInfo Identifier GI:115525971; *Burkholderia cenocepacia* HI24244-hydroxybenzoyl-CoA thioesterase (SEQ ID NO:32) having Genbank Accession Number ABK07557 and GenInfo Identifier GI:116646916; *Burkholderia cenocepacia* PC1844-hydroxybenzoyl-CoA thioesterase (SEQ ID NO:33) having Genbank Accession Number ZP_04939537 and GenInfo Identifier GI:254246216; *Magnetospirillum gryphiswaldense* MSR-1 4-hydroxybenzoyl-CoA thioesterase (SEQ ID NO:34) having Genbank Accession Number CAM73991 and GenInfo Identifier GI:144897127; *Burkholderia ambifaria* MEX-5 tol-pal system-associated acyl-CoA thioesterase (SEQ ID NO:35) having Genbank Accession Number ZP_02911196 and GenInfo Identifier GI:171322375; *Burkholderia ambifaria* MC40-6 tol-pal system-associated acyl-CoA thioesterase (SEQ ID NO:36) having Genbank Accession Number ACB63194 and GenInfo Identifier GI:171992275; *Burkholderia ambifaria* AMMD 4-hydroxybenzoyl-CoA thioesterase (SEQ ID NO:37) having Genbank Accession Number YP_772574 and GenInfo Identifier GI:115350735; *Granulibacter bethesdensis* CGD-NIH1 short-chain acyl-CoA hydrolase (SEQ ID NO:38) having Genbank Accession Number YP_744923 and GenInfo Identifier GI:114327766; *Haemophilus somnus* 129PT thioesterase (SEQ ID NO:39) having Genbank Accession Number YP_718466 and GenInfo Identifier GI:113460404; *Haemophilus somnus* 2336 Pol-Pal system-associated acyl-CoA thioesterase (SEQ ID NO:40) having Genbank Accession Number YP_001783484 and GenInfo Identifier GI:170717543; *Proteus mirabilis* HI4320 thioesterase (SEQ ID NO:41) having Genbank Accession Number YP_002150349 and GenInfo Identifier GI:197284477; *Burkholderia ambifaria* IOP40-10 tol-pal system-associated acyl-CoA thioesterase (SEQ ID NO:42) having Genbank Accession Number ZP_02892046 and GenInfo Identifier GI:170701069; *Proteus mirabilis* ATCC 29906 thioesterase (SEQ ID NO:43) having Genbank Accession Number ZP_03841041 and GenInfo Identifier GI:227356655; *Rhodopseudomonas palustris* B is B184-hydroxybenzoyl-CoA thioesterase (SEQ ID NO:44) having Genbank Accession Number YP_531800 and GenInfo Identifier GI:90423430; *Azospirillum* sp. B510 acyl-CoA thioester hydrolase (SEQ ID NO:45) having Genbank Accession Number YP_003448162 and GenInfo Identifier GI:288957821; *Rhodopseudomonas palustris* DX-1 tol-pal system-associated acyl-CoA thioesterase (SEQ ID NO:46) having Genbank Accession Number ZP_06358294 and GenInfo Identifier GI:283840748; *Bradyrhizobium* sp. BTAi1 Thioesterase superfamily (SEQ ID NO:47) having Genbank Accession Number AB Q38791 and GenInfo Identifier GI:146410285; *Rhodospirillum centenum* SW small, thioesterase-like enzyme subunit, putative (SEQ ID NO:48) having Genbank Accession Number YP_002298014 and GenInfo Identifier GI:209965099; *Methylosinus trichosporium* OB3b tol-pal system-associated acyl-CoA thioesterase (SEQ ID NO:49) having Genbank Accession Number ZP_06889725 and GenInfo Identifier GI:296447812; *Rhodopseudomonas palustris* HaA24-hydroxybenzoyl-CoA thioesterase (SEQ ID NO:50) having Genbank Accession Number YP_487867 and GenInfo Identifier GI:86751371; and *Methylobacterium extorquens* PA1 tol-pal system-associated acyl-CoA thioesterase (SEQ ID NO:51) having Genbank Accession Number ABY33133 and GenInfo Identifier GI:163665766.

In some embodiments, the genetically engineered microorganism that includes a 4-hydroxybenzoyl-CoA thioesterase can produce a fatty aldehyde, fatty alcohol, and/or a wax ester, and can optionally include one or more nucleic acid molecules encoding an acyl-CoA reductase, carboxylic acid reductase, acyl-ACP reductase, an fatty aldehyde reductase, an wax synthase, or a combination thereof. Wax esters include an acyl chain (A chain) on the carbonyl side of the ester bond and an ester chain (B chain) connected to the oxygen of the ester bond, one or both of which can be derived from a fatty acid, e.g., generated by a thioesterase such as the 4-hydroxybenzoyl-CoA thioesterase. Wax esters can have a total number of carbons (an A+B "chain length"), for example, from 10 to 36 carbons, for example from 16 to 36 carbons, from 16 to 32 carbons, or from 24 to 32 carbons.

Additionally or alternately, the genetically engineered microorganism that includes a 4-hydroxybenzoyl-CoA thioesterase can produce an alkane and/or alkene and can optionally include at least one nucleic acid molecule encoding a fatty acid decarboxylase, an fatty aldehyde decarboxylase, an acyl-CoA reductase, carboxylic acid reductase, acyl-ACP reductase, or a combination thereof. Alkanes and/or alkenes produced by and/or derived from a photosynthetic microorganism that includes a nucleic acid molecule encoding an 4-hydroxybenzoyl-CoA thioesterase can, for example, have a chain length of 7, 9, 11, 13, 15, 17, 19, 21, and/or 23 carbons (e.g., one or more odd numbered chain lengths from 7 to 17 carbons, from 7 to 15 carbons, or from 11 to 15 carbons).

Further additionally or alternately, a genetically engineered microorganism that can produce a fatty alcohol, fatty aldehyde, wax ester, alkane, or alkene may optionally include a nucleic acid molecule encoding an acyl-CoA synthetase.

The nucleic acid molecule encoding the 4-hydroxybenzoyl-CoA thioesterase can advantageously be stably integrated into the chromosome of the host microorganism, in an autonomously replicating episome, in an expression construct, or a combination thereof. Additionally or alternately, the genetically engineered microorganisms can be transformed with exogenous genes from prokaryotes by the introduction of appropriate nucleic acid expression constructs that can include, in addition to the gene of interest, gene expression sequences and optionally sequences that can mediate recombination into the host chromosome.

Expression constructs can be introduced into prokaryotic and eukaryotic cells via conventional transformation or transfection techniques. The terms "transformation" and "transfection", conjugation and transduction, as used in the present context, are intended to comprise a multiplicity of methods known in the art for the introduction of foreign nucleic acid (for example DNA) into a host cell, including, but not limited to, calcium phosphate or calcium chloride coprecipitation, DEAE-dextran-mediated transfection, lipofection, natural competence, chemically mediated transfer, electroporation, and/or particle bombardment. Suitable methods for the transformation or transfection of host cells can be found in Molecular Cloning—A Laboratory Manual (2010), Cold Spring Harbor Laboratory Press, the contents of which are incorporated by reference herein.

For example, algae and photosynthetic bacteria can be transformed by any suitable method, including, as non-limiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017), electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 1340-649; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly (amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation also can be performed on algal cells, for example after removing or wounding the algal cell wall (e.g., International Publication No. WO 2000/62601; Kumar et al. (2004) *Plant Sci.* 166: 731-738). Biolistic methods are useful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; and International Publication Nos. WO 2003/091413, WO 2005/005643, and WO 2007/133558 (each of which cited reference is incorporated by reference in its entirety).

For optimal expression of a recombinant protein, in many instances it can be beneficial to employ coding sequences that can produce mRNA with codons preferentially used by the host cell to be transformed. Thus, for an enhanced expression of transgenes, the codon usage of the transgene can be matched with the specific codon bias of the organism in which the transgene is being expressed. For example, methods of recoding genes for expression in microalgae are described in U.S. Pat. No. 7,135,290, the content of which is incorporated by reference. All or a subset of the codons of a gene can be changed to incorporate a preferred codon used by the host organism. Additional information for codon optimization is available, e.g., at the codon usage database of Genbank.

In some embodiments, the thioesterase-encoding nucleotide sequence in microorganisms transformed with an isolated nucleic acid molecule including a nucleic acid sequence encoding an 4-hydroxybenzoyl-CoA thioesterase can be operably linked to one or more expression control elements and can optionally be codon-optimized for expression in the microorganism.

Alternatively or in addition, the exogenous nucleic acid molecule as disclosed herein can be cloned into an expression vector for transformation into a microorganism such as, for example, a microalga or a photosynthetic bacterium. The vector can include sequences that promote expression of the transgene of interest (e.g., an exogenous 4-hydroxybenzoyl-CoA thioesterase gene) such as a heterologous promoter, and may optionally include, for expression in eukaryotic cells, without limitation, an intron sequence, a sequence having a polyadenylation signal, etc. Alternately, if the vector does not contain a promoter in operable linkage with the gene of interest, the gene can be transformed into the cells such that it becomes operably linked to an endogenous promoter by homologous recombination or vector integration.

Vectors designed for expression of a gene in microalgae can include a promoter active in microalgae operably linked to the exogenous gene being introduced. A variety of gene promoters and terminators that function in microalgae can be utilized in expression vectors, including, but not limited to, promoters and terminators from prokaryotes or eukaryotes, such as, but not limited to, *Chlamydomonas* and other algae (see, for example, *Plant Cell Physiol* 49: 625-632, 2008), promoters and terminators from viruses, and synthetic promoters and terminators.

For transformation of diatoms, a variety of gene promoters that function in diatoms can be utilized in these expression vectors, including, but not limited to: promoters from *Thalassiosira* and other heterokont algae, promoters from viruses, and synthetic promoters. Promoters from *Thalassiosira pseudonana* that would be suitable for use in expression vectors include, without limitation, an alpha-tubulin promoter, a beta-tubulin promoter, and an actin promoter. Promoters from *Phaeodactylum tricomuturn* that would be suitable for use in expression vectors include, without limitation, an alpha-tubulin promoter, a beta-tubulin promoter, and an actin promoter. The terminators associated with these genes, other diatom genes, or particular heterologous genes can be used to stop transcription and provide the appropriate signal for polyadenylation.

If desired, in order to express the exogenous nucleic acid molecule, such as, 4-hydroxybenzoyl-CoA thioesterase, in the plastid, where the fatty acid biosynthesis occurs in microalgae, a nucleotide sequence encoding a chloroplast transit peptide can be added to the N-terminus of the exogenous nucleic acid molecule. Alternately, the exogenous nucleic acid molecule encoding a 4-hydroxybenzoyl-CoA thioesterase can be introduced directly into the plastid chromosome of microalgae without disrupting photosynthetic capability of the plastid. Methods for plastid transformation are well known for introducing a nucleic acid molecule into a plant cell chloroplast (see, for example, International Publication Nos. WO 2010/019813 and WO 95/16783; U.S. Pat. Nos. 5,451,513, 5,545,817, and 5,545,818; and McBride et al., *Proc. Natl. Acad. Sci. USA* 91:7301-7305 (1994), each of which are incorporated by reference herein).

In some instances, it can be advantageous to express an enzyme, such as, but not limited to, an 4-hydroxybenzoyl-CoA thioesterase, at a certain point during the growth of the genetically engineered host organism to minimize any deleterious effects on the growth of that organism and/or to maximize production of the fatty acid product of interest. In these instances, one or more exogenous nucleic acid molecules encoding a 4-hydroxybenzoyl-CoA thioesterase introduced into the genetically engineered organism can be operably linked to an inducible promoter. The promoter can be, for example, without limitation, a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter; see U.S. Pat. No. 6,379,945), a metallothionien promoter (U.S. Pat. No. 6,410,828), and/or a pathogenesis-related (PR) promoter that can be responsive to a chemical such as, for example, salicylic acid, ethylene, thiamine, or BTH (U.S. Pat. No. 5,689,044). An inducible promoter can be responsive to light or dark (U.S. Pat. Nos. 5,750,385 and 5,639,952), temperature (U.S. Pat. No. 5,447,858; Abe et al., *Plant Cell Physiol.* 49: 625-632 (2008); Shroda et al. *Plant J.* 21: 121-131 (2000)), or the like, or combinations thereof. The foregoing list is meant to be exemplary and not limiting. The promoter sequences can be from any organism, provided that they are functional in the host organism. Inducible promoters, as used in the constructs of the present invention, can use one or more portions/domains of the aforementioned promoters and/or other inducible promoters fused to at least a portion of a different promoter that operates in the host organism to confer inducibility on a promoter that operates in the host species.

For example, for transformation of cyanobacteria, a variety of promoters that function in cyanobacteria can be utilized, including, but not limited to, the lac, tac and trc promoters and derivatives that are inducible by the addition of isopropyl β-D-1-thiogalactopyranoside (IPTG), promoters that are naturally associated with transposon- or bacterial chromosome-borne antibiotic resistance genes (neomycin phosphotransferase, chloramphenicol acetyltransferase, spectinomycin adenyltransferase, etc.), promoters associated with various heterologous bacterial and native cyanobacterial genes, promoters from viruses and phages, and synthetic promoters. One embodiment of such promoter includes an IPTG-inducible trcY promoter (SEQ ID NO:52). Promoters isolated from cyanobacteria that can be used can include, without limitation, secA (secretion; controlled by the redox state of the cell), rbc (Rubisco operon), psaAB (PS I reaction center proteins; light regulated), and psbA (D1 protein of PSII; light-inducible).

Likewise, a wide variety of transcriptional terminators can be used for expression vector construction. Examples of possible terminators include, but are not limited to, psbA, psaAB, rbc, secA, and T7 coat protein.

Transformation vectors can optionally also include a selectable marker, such as, but not limited to, a drug resistance gene, an herbicide resistance gene, a metabolic enzyme or factor required for survival of the host (for example, an auxotrophic marker), and the like, as well as combinations thereof. Transformed cells can optionally be selected based upon the ability to grow in the presence of the selectable marker under conditions in which cells lacking the resistance cassette or auxotrophic marker would not grow. Alternately, a non-selectable marker may be present on a vector, such as a gene encoding a fluorescent protein or enzyme that generates a detectable reaction product.

Expression vectors can be introduced into the microorganisms by standard methods, including, but not limited to, natural DNA uptake, conjugation, electroporation, particle bombardment and abrasion with glass beads, SiC fibers, or other particles. The vectors can be, for example, (1) targeted for integration into the host chromosome by including flanking sequences that enable homologous recombination into the chromosome, (2) targeted for integration into endogenous plasmids by including flanking sequences that enable homologous recombination into the endogenous plasmids, and/or (3) designed such that the expression vectors replicate within the chosen host.

The genetically engineered microorganism can further comprise one or more additional recombinant nucleic acid molecules that may enhance production of fatty acids and/or fatty acid derivatives, such as, for example, a gene encoding an acetyl-CoA carboxylase enzyme and/or a gene encoding a β-ketoacyl synthase (KAS), such as a KAS III, KAS II, or KAS I enzyme. Additionally or alternately, the microorganism can have attenuated expression of a gene encoding acyl-ACP synthase, acyl-CoA synthase, acyl-CoA dehydrogenase, glycerol-3-phosphate dehydrogenase, acetaldehyde-CoA dehydrogenase, pyruvate dehydrogenase, acetate kinase, or the like, or a combination thereof.

In some embodiments, the engineered microorganism can be a photosynthetic microorganism and the culture medium can be a medium that does not include a reduced carbon compound for supplying energy to the genetically engineered photosynthetic microorganism, and yet the culture comprising the microorganism can include at least 5 mg per liter, for example at least 10 mg per liter, at least 20 mg per liter, at least 30 mg per liter, at least 40 mg per liter, or at least 50 mg per liter, of free fatty acids and/or fatty acid derivatives produced by the microorganism.

The recombinant nucleic acid molecule encoding the 4-hydroxybenzoyl-CoA thioesterase can be any as described hereinabove, for example, a member of Pfam family PF03061 and/or, when queried against the Pfam database, is a match with PF03061 with a bit score greater than the gathering threshold value of 20.6. In some examples, the microorganism can include a recombinant nucleic acid molecule encoding a polypeptide that recruits to pfam PF03061 with a bit score of greater than 20.6 and an e value of less than 0.1, in which the polypeptide has an amino acid sequence that has at least 50% identity, at least 55% identity, at least 60% identity, at least 65% identity, at least 70% identity, for example at least 75%, at least 80%, at least 85%, at least 90%, or at least 95% identity, with SEQ ID NO:2, where the rmicroorganism produces at least one free fatty acid or at least one fatty acid derivative. In some examples, the microorganism can include a recombinant nucleic acid molecule encoding a polypeptide that recruits to pfam PF03061 with a bit score of greater than 20.6 and an e value of less than 0.1, in which the polypeptide has an amino acid sequence that has at least 70% identity, at least 75% identity, at least 80% identity, at least 85% identity, at least 90% identity, for example at least 95% identity, at least 96% identity, at least 97% identity, at least 98% identity, at least 99% identity, or about 100% identity, with SEQ ID NO:1, where the microorganism produces at least one free fatty acid or at least one fatty acid derivative.

As mentioned herein, the nucleic acid molecule can be operably linked to a promoter active in a photosynthetic microorganism and optionally one or more additional nucleic acid regulatory sequences, such as, for example, a transcriptional terminator sequence. Additionally or alternately, the nucleic acid molecule can be present on a self-replicating plasmid that is introduced into a photosynthetic microorganism, and/or can be integrated into the genome of a photosynthetic microorganism.

In some embodiments, the fatty acids and/or fatty acid derivatives can be present in the media, for example, as precipitates in or on, at or near the surface of the media, associated with the media vessel as droplets, including suspended droplets (e.g., an emulsion), as a relatively immiscible layer floating on top of the aqueous culture medium, as a "scum", film, gel, semi-solid, colloid, fine particulate, particulate, solid, or aggregate that may be dispersed, suspended, or entrained within the culture medium, associated with the cells of the photosynthetic microorganism, phase separated in some other fashion, or a combination thereof.

In preferred embodiments, at least one free fatty acid produced by a culture as disclosed herein can have an acyl chain length from 8 to 24 carbons, for example from 8 to 18 carbons, from 12 to 16 carbons, or of 8, 10, 12, 14, 16, 18, 20, 22, and/or 24 carbons. In embodiments where at least one fatty acid derivative (such as one or more fatty alcohols, fatty aldehydes, wax esters, alkanes, and alkenes) are produced by a culture as disclosed herein, the at least one fatty acid derivative can have a total number of carbons from 7 to 36, for example from 11 to 34, from 12 to 32, or of 7, 8, 9, 10, 11, 12, 13, 14, 15, 16, 17, 18, 19, 20, 21, 22, 23, 24, 26, 28, 30, 32, 34, and/or 36.

Advantageously, the culture medium can be any suitable for growth of a photosynthetic host microorganism. In one embodiment, the culture can include a source of reduced carbon, such as, for example, one or more sugars or organic acids that can be used by the microorganism for growth, such that the microorganism can grow heterotrophically or mixotrophically. Additionally or alternately, the culture medium does not include a substantial amount of a reduced carbon compound that can be used for the organism as an energy source and/or includes a source of inorganic carbon, such as $CO_2$ or bicarbonate.

II. Methods of Producing Free Fatty Acids and/or Derivatives

An aspect of the present invention relates to a method for producing a free fatty acid and/or derivative in a culture, the method comprising culturing a microorganism that includes at least recombinant one nucleic acid sequence encoding an 4-hydroxybenzoyl-CoA thioesterase in growth media under conditions that allow expression of the 4-hydroxybenzoyl-CoA thioesterase. Expression of the exogenous 4-hydroxybenzoyl-CoA thioesterase gene in the microorganism can result in production of at least one free fatty acid and/or fatty acid derivative.

In one embodiment, the culture that includes the microorganism with the recombinant gene that expresses an 4-hydroxybenzoyl-CoA thioesterase can produce at least twice the amount of the fatty acid and/or derivative, compared to a culture that is identical in all respects except that the microorganism does not include a recombinant nucleic acid sequence encoding a 4-hydroxybenzoyl-CoA thioesterase. For example, the microorganism that includes the recombinant nucleic acid molecule encoding the 4-hydroxybenzoyl-CoA thioesterase can produce (and optionally but preferably release and/or secrete) at least 5 mg per liter, for example at least 10 mg per liter, at least 20 mg per liter, at least 30 mg per liter, at least 40 mg per liter, or at least 50 mg per liter, of free fatty acids and/or fatty acid derivatives.

The method can further comprise isolating/removing the free fatty acid and/or derivative from the culture, e.g., from the cells, the growth media, or the whole culture. For example, the isolation can be by organic extraction of whole or lysed cells, removal of free fatty acids or fatty acid derivatives as precipitates or from the upper layer of the culture media ("skimming"), through the use of particulate adsorbents, bubbles, or matrices that bind the fatty acids and/or derivatives, or the like, or any combination thereof.

The genetically engineered microorganism can be any as described herein that includes a recombinant nucleic acid molecule encoding an 4-hydroxybenzoyl-CoA thioesterase, whose expression can result in production of free fatty acids and/or fatty acid derivatives. The 4-hydroxybenzoyl-CoA thioesterase can be expressed by the microorganism for at least a portion of the time during which the photosynthetic microorganism is cultured and/or upon administering an inducer to the culture. Non-limiting examples of an inducer include lactose or a lactose analogue, such as isopropyl β-D-1-thiogalactopyranoside, and light, which can be provided as sunlight or artificial light, such as, for example, fluorescent light.

Additionally or alternately, the genetically engineered microorganism can be a photosynthetic microorganism and can be grown phototrophically, in which case the growth media typically does not include a substantial amount of (e.g., includes none of) a reduced carbon source. When growing phototrophically, the photosynthetic microorganism uses light as its energy source, and an inorganic carbon source, such as $CO_2$ or bicarbonate, is used for synthesis of biomolecules by the microorganism. Alternately, an organic carbon molecule or compound can be provided in the culture medium of a microorganism grown phototrophically, but it either cannot be taken up or metabolized by the cell for energy or is not present in an amount effective to provide energy sufficient for the growth of the cell culture.

In many embodiments, the culture can include an inorganic carbon source, including, but not limited to, bicarbonate, calcium carbonate, and/or $CO_2$, present in air, or provided in enriched form with respect to ambient $CO_2$, for example, as 5 vol % $CO_2$ in air. Additionally or alternately, the photosynthetic microorganisms can be exposed to light for at least a portion of the culturing period. Artificial light sources can be used as the sole light source or to enhance or extend natural light.

"Culturing" refers to the intentional fostering of growth (increases in cell size, cellular contents, and/or cellular activity) and/or propagation (increases in cell numbers, e.g., via mitosis) of one or more cells by use of selected and/or controlled conditions. The combination of both growth and propagation may be termed "proliferation." Examples of selected and/or controlled conditions can include the use of a defined medium (with known characteristics, such as pH, ionic strength, and carbon source), specified temperature, oxygen tension, carbon dioxide levels, and growth in a bioreactor, inter alia.

Photosynthetic microorganisms, such as, microalgae or cyanobacteria, can be cultured phototrophically, in the absence of a substantial amount of a fixed carbon source, or mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid form (e.g., acetate, citrate, succinate), and/or glycerol. The photosynthetic microorganism, alternately, can be cultured mixotrophically, such that the organism is grown in the presence of light for at least a part of the day, and also provided with one or more sources of reduced carbon. Cells can alternately be grown heterotrophically, where a reduced carbon source is provided in the media for energy and biochemical synthesis. A photosynthetic organism can be grown mixotrophically for a period of time, followed by a period of phototrophic growth, or vice versa.

A variety of media for phototrophic and/or mixotrophic growth of algae and cyanobacteria are known in the art, and media can be optimized to enhance growth or production of fatty acid products for a particular species.

Microorganisms that may be useful in accordance with the methods of the present invention can be found in various locations and environments throughout the world. As a consequence of their isolation from other species and their resulting evolutionary divergence, the particular growth medium for optimal growth and generation of lipid and/or hydrocarbon constituents can vary. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of strains of microorganisms. For example, various fresh water and salt water media can include those described in Barsanti, L. amd Gualtieri, P. (2005) Algae: Anatomy, Biochemistry, and Biotechnology, CRC Press, Taylor & Francis Group, Boca Raton, Fla., USA, which is incorporated herein by reference for media and methods for culturing algae. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (ccap.ac.uk/media/pdfrecipes); and Katedra Botaniky (/botany.natur.cuni.cz/algo/caup-media.html).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Example 6), or a modified medium such as ATCC Medium 854 (BG-11 modified to contain vitamin B12) or ATCC Medium 617 (BG-11 modified for marine cyanobacteria, containing additional NaCl and vitamin B12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation.

In further embodiments, by using the excess amount of metal (e.g., calcium) in the medium, at least a portion of the fatty acid(s) can be sequestered as soap precipitates, which may result in decreasing the toxic effects of free fatty acid(s). Addition of metal (e.g., calcium) in the medium can additionally or alternately increase the tolerance of microorganism in media with a relatively high concentration of free fatty acids. Additionally or alternately, fatty acid-producing strains can advantageously be more robust with excess metal (e.g., calcium) content. Although the excess component is described herein as a metal, it is contemplated that the component can more generally be described as a carboxylate counterion source, for example an soap-forming counterion source, a metal ion source (noted as "metal" herein), a multivalent (i.e., having a valence of +2 or higher) counterion source, a divalent counterion source, or some combination. For production of fatty acids and/or fatty acid derivatives, photosynthetic microorganisms can be grown indoors (e.g., in photobioreactors, in shake flasks, test tubes, vials, microtiter dishes, petri dishes, or the like) or outdoors (e.g., in ponds, canals, trenches, raceways, channels, or the like). Additionally or alternately, a source of inorganic carbon (such as, but not limited to, $CO_2$), including, but not limited to, air, $CO_2$ enriched air, or flue gas, can be supplied to the photosynthetic microorganisms.

Additionally or alternately, the present invention can include one or more of the following embodiments.

Embodiment 1

A microorganism comprising a recombinant nucleic acid molecule encoding a 4-hydroxybenzoyl-CoA thioesterase, wherein expression of the 4-hydroxybenzoyl-CoA thioesterase in the microorganism results in production of at least one free fatty acid and/or fatty acid derivative.

Embodiment 2

The microorganism according to embodiment 1, wherein the 4-hydroxybenzoyl-CoA thioesterase hydrolyzes an acyl-ACP.

Embodiment 3

The microorganism according to any one of the previous embodiments, wherein the at least one fatty acid derivative comprises at least one fatty aldehyde, at least one fatty alcohol, at least one wax ester, at least one alkane, at least one alkene, or a combination thereof, and/or has a total number of carbons from 7 to 36.

Embodiment 4

The microorganism according to any one of the previous embodiments, wherein the microorganism is capable of producing at least one fatty acid having an acyl chain length from 8 to 24 carbons or from 8 to 18 carbons.

Embodiment 5

The microorganism according to any one of the previous embodiments, wherein at least 30 wt % of the free fatty acids produced by the microorganism are free fatty acids having an acyl chain length of 8 carbons, 10 carbons, 12 carbons, 14 carbons, 16 carbons, 18 carbons, or any mixture thereof.

Embodiment 6

The microorganism according to any one of the previous embodiments, wherein the 4-hydroxybenzoyl-CoA thioesterase is prokaryotic and/or has at least 70% amino acid sequence identity, for example at least 75%, at least 80%, at least 85%, at least 90%, at least 95%, at least 96%, at least 97%, at least 98%, at least 99%, or about 100% sequence identity, to SEQ ID NO:1 or SEQ ID NO:2.

Embodiment 7

The microorganism according to any one of the previous embodiments, wherein the nucleic acid molecule encoding the 4-hydroxybenzoyl-CoA thioesterase comprises nucleotide sequence SEQ ID NO:3 or SEQ ID NO:4.

Embodiment 8

The microorganism according to any one of the previous embodiments, wherein the nucleic acid molecule encoding the 4-hydroxybenzoyl-CoA thioesterase is stably integrated into a chromosome of the microorganism and/or is in an expression construct.

Embodiment 9

The microorganism according to embodiment 8, wherein the expression construct comprises a promoter operably linked to the nucleic acid molecule encoding the 4-hydroxybenzoyl-CoA thioesterase, wherein the promoter is functional in the microorganism.

Embodiment 10

The microorganism according to any one of the previous embodiments, wherein the microorganism further comprises at least one additional nucleic acid molecule encoding at least one additional polypeptide such as acetyl-CoA carboxylase or β-ketoacyl synthase (KAS), wherein expression of the additional nucleic acid molecule in the photosynthetic microorganism enhances production of a free fatty acid and/or fatty acid derivative.

Embodiment 11

The microorganism according to any one of the previous embodiments, wherein the microorganism has attenuated expression of at least one gene encoding a protein comprising acyl-acyl carrier protein (ACP) synthase, acyl-CoA dehydrogenase, glycerol-3-phosphate dehydrogenase, acetaldehyde-CoA dehydrogenase, pyruvate dehydrogenase, acetate kinase, and combinations thereof.

Embodiment 12

The microorganism of any of the previous embodiments, wherein the microorganism is a bacterium, a heterokont, a thraustochytrid, or a fungus, and can be a member of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula,* or *Saccharomyces.*

Embodiment 13

The microorganism of any of embodiments 1-11, wherein the microorganism is a photosynthetic microorganism, and can be a microalga or a cyanobacterium.

Embodiment 14

A method for producing a free fatty acid and/or fatty acid derivative in a culture, the method comprising culturing a microorganism in growth media, wherein the microorganism comprises at least one recombinant nucleic acid molecule encoding a 4-hydroxybenzoyl-CoA thioesterase according to any one of the previous embodiments; and wherein the microorganism is grown under a condition that allows expression of the exogenous 4-hydroxybenzoyl-CoA thioesterase gene during a culturing period.

Embodiment 15

The method according to embodiment 14, wherein at least a portion of the free fatty acid and/or fatty acid derivative is secreted into the growth media.

Embodiment 16

The method according to embodiment 14 or embodiment 15, wherein the microorganism is a photosynthetic microorganism, and further wherein the growth medium does not include a substantial amount of a reduced carbon source, wherein the culture is provided with at least one source of inorganic carbon, and/or wherein the culture is exposed to light for at least a portion of the culturing period.

Embodiment 17

The method according to any one of embodiments 14-16, wherein the method further comprises isolating at least one free fatty acid and/or derivative from the microorganism, the growth media, or the whole culture.

Embodiment 18

An isolated or recombinant nucleic acid molecule comprising a sequences that encodes a polypeptide having an amino acid sequence at least 50%, at least 55%, at least 60%, at least 65%, at least 70%, at least 75%, at least 80%, at least 85%, at least 95%, at least 97%, or about 100% identical to SEQ ID NO:2.

Embodiment 19

An isolated or recombinant nucleic acid molecule comprising a sequences that encodes a polypeptide having an amino acid sequence at least 80%, at least 85%, at least 90%, at least 95%, at least 96%, at least 97%, at least 98%, at least 99%, or about 100% identical to SEQ ID NO:1.

Embodiment 20

An isolated or recombinant nucleic acid molecule according to Embodiment 18 or 19, wherein the polypeptide has acyl-ACP thioesterase activity.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference in their entireties.

Nucleic acid and amino acid sequences identified by Accession Numbers or GenInfo Identifiers are also incorporated by reference herein. Accession numbers are unique identifiers for a sequence record publicly available at the National Center for Biotechnology Information internet site maintained by the United States National Institutes of Health, which can be accessed at ncbi.nlm.nih.gov. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appeared in a specific Genbank record. Searching and obtaining nucleic acid or gene sequences or protein sequences based on Accession numbers and GI numbers is well known in the arts of cell biology, biochemistry, molecular biology, and molecular genetics.

It must also be noted that as used herein and in the appended claims, the singular forms "a," "an," and "the"

include plural referents unless the context clearly dictates otherwise. The use of "or" in a listing of two or more items indicates that any combination of the items is contemplated, for example, "A or B" indicates that A alone, B alone, or both A and B are intended. All technical and scientific terms used herein have the same meaning.

All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1

Generation of Metagenomic Library 1.1. Isolation of Metagenomic DNA

In order to isolate metagenomic DNAs that may contain novel thioesterase genes, ~20 liter whole water samples were collected from a fish pond at Pacific Aquafarms located north of the Salton Sea in Southern California.

About 8 L of water was filtered from the above site, using a Millipore Stainless Steel filtration train, through ~20 µm, ~3 µm, ~0.8 µm, and ~0.1 µm filters. A ~0.1 µm filter was placed in an air-tight Ziploc® freezer bag (S.C. Johnson, Racine, Wis.). A section of the filter was added to media for expansion of microorganism populations for producing metagenomic libraries. One filter sample was grown in Luria Broth (LB) medium shaking at ~225 rpm at about 30° C., and another filter sample was grown in Luria Broth (LB) medium shaking at ~225 rpm at about 40° C., both overnight. After the grow-out period, the cell suspensions were collected by centrifugation at ~4,000 g for about 10 mins at room temperature (~20-25° C.). The cell pellets were resuspended in ~50 mM Tris-Cl, pH ~8.0 (containing ~10 mM EDTA, ~100 µg/ml RNase A, ~4 mg/ml Lysozyme, ~100 µg/ml Lysostaphin, and ~500 U/ml Mutanolysin), and incubated at ~37° C. with agitation (~100 rpm). The homogenates were sedimented by centrifugation for about 30 mins at ~16,000 g at ~4° C. The supernatants were transferred to new tubes and mixed with an equal volume of cold (about −20° C.) 100% ethanol to precipitate the DNA. The precipitate was collected by centrifugation at ~16,000 g at ~4° C. or spooled onto a sterile disposable inoculation loop. The DNA was washed then in ~75% ethanol and dried at room temperature and resuspended in ~50 mM Tris-Cl, pH ~8.0, for fractionation and library construction.

1.2 Construction of Metagenomic DNA Library and Functional Screening

Figure 2:
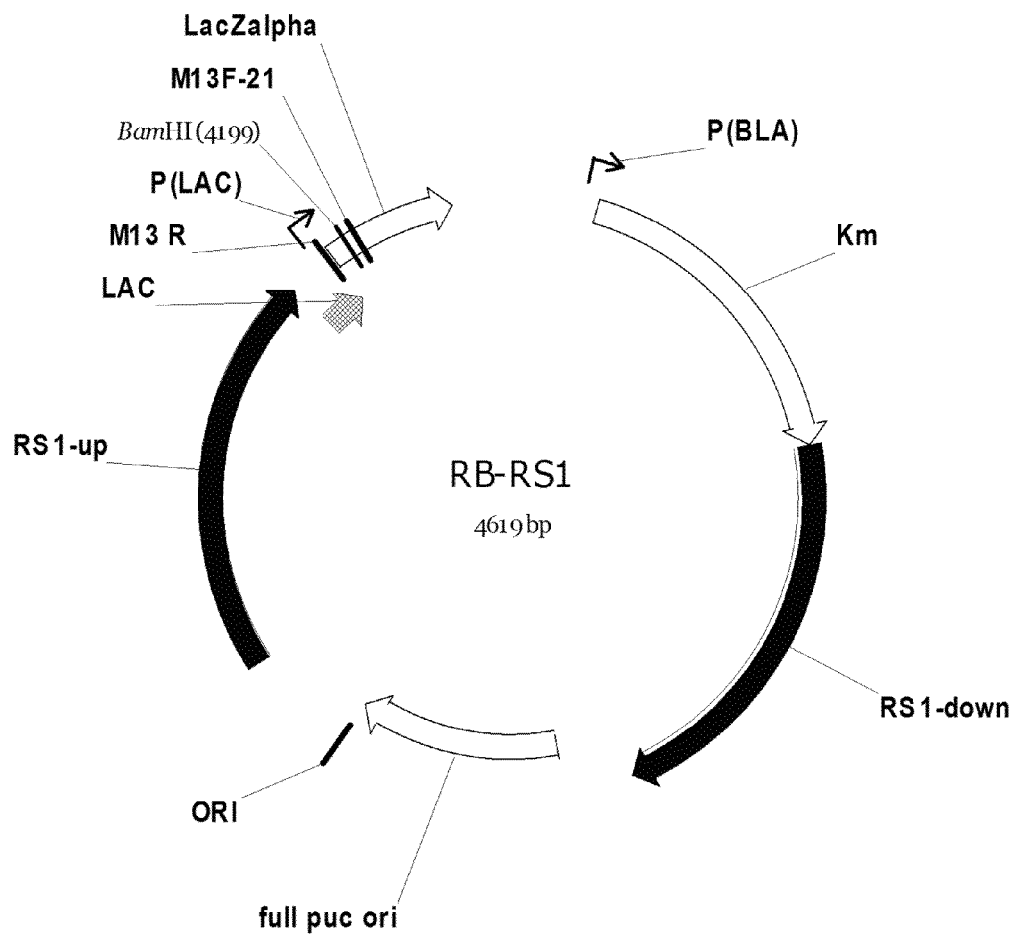
FIG. 2 shows the physical map of the expression vector (RB-RS1) used for constructing a metagenomic library.

The isolated metagenomic DNAs from the ~30° C. amplified metagenomic sample and the ~40° C. amplified metagenomic sample were partially digested with restriction endonuclease Sau3AI and ligated into the BamHI site of bacterial/cyanobacterial expression/integration vector RB-RS1 (SEQ ID NO:5; FIG. 2) to generate ~30° C. and ~40° C. metagenomic libraries. The RB-RS1 expression vector was constructed using a pUC backbone from which the lactamase gene conferring ampicillin resistance was deleted. The vector was built such that the lac promoter, the lac Z alpha gene, and a kanamycin resistance gene were flanked by RS1 "up" sequence and RS1 "down" sequences for homologous recombination into RS1 site in the *Synechocystis* genome (Williams et al. (1988) *Methods in Enzymology*, 167: 766-778). The ~30° C. and ~40° C. libraries were transformed into competent *E. coli* K19 cells, and kanamycin-resistant colonies were screened for production of free fatty acids via a Nile Blue Plate Assay.

A plate-based assay was used to identify recombinant *E. coli* colonies producing free fatty acids on a solid media that contained ~10 µg/mL Nile Blue A (Alfa Aesar #A17174). Nile blue stains polar lipids (fatty acids, phospholipids) in blue. Colonies were examined by visual inspection for staining by positioning plates on a standard light box. Colonies displaying a high level of Nile Blue A staining over background controls were selected, grown up, and further screened to determine the amount of total non-esterified free fatty acid (FFA) using a free fatty acid Detection kit (#SFA-1, Zenbio, Inc, Research Triangle Park, N.C.).

The free fatty acid content of samples exhibiting elevated free fatty acid levels over background controls in the Nile Blue plate assay and by assay with the free fatty acid detection kit were analyzed further by gas chromatography (GC) with flame ionization detection (GC-FID). Two hundred clones showing elevated free fatty acid levels in GC-FID analysis over background controls were selected, and the nucleotide sequences of the clones were determined. Following DNA sequencing, removal of redundant clones, and bioinformatic analysis, a recurring pattern of clones belonging to a family of 4-hydroxybenzoyl-CoA thioesterase genes was observed. Among the family of the 4-hydroxybenzoyl-CoA thioesterase genes, two clones, 340-64 (SEQ ID NO:3) and 3-1 (SEQ ID NO:4), were characterized in more detail.

Example 2

Expression of Metagenomic DNA in *E. coli*

For expression of the prokaryotic thioesterase genes in *E. coli*, ~1.2 mL of 2×YT media containing ~50 ng/ml spectinomycin and ~1 mM Isopropyl β-D-1-thiogalactopyranoside (IPTG) in a glass tube was inoculated with ~30 microliters of a saturated culture of each bacterial strain and cultured for about 24 hours. About 0.6 mL of the culture was removed for biochemical analysis.

Example 3

Analysis of Fatty Acid Samples from *E. coli*

For identification and quantitation of fatty acids produced by the transformed *E. coli* strains, ~0.6 mL of the *E. coli* cultures was added to ~2 mL glass gas chromatography vials with PTFE (polytetrafluoroethylene)-lined caps (National Scientific). Fifty microliters of an internal standard set including the free fatty acids with acyl chain lengths of 9 carbons (C9:0), 13 carbons (C13:0), and 17 carbons (C17:0), each at a concentration of ~600 μg/ml, in hexane, were added to the culture sample, followed by ~50 microliters of ~50% $H_2SO_4$, ~100 microliters of ~5M NaCl, and ~850 microliters of hexane. The final concentration of each internal standard was ~50 μg/ml. The fatty acids for making the internal standard set were purchased from Fluka or Nu Chek Prep. The cultures were vortexed then on a multi-tube vortexer at ~2,500 rpm for ~30 mins. The vials were finally centrifuged for ~3 min at ~2500 rpm to provide good separation between organic and aqueous phases. The hexane layers were sampled by a Gerstel MPS2L Autosampler.

E. coli fatty acid samples were analyzed using an Agilent model 7890A gas chromatograph equipped with an FID (flame ionization detector) that included a J&W Scientific DB-FFAP capillary column (~15 m length, ~0.25 mm internal diameter, ~0.25 μm film thickness) coupled to an Agilent 5975C mass spectrophotometer. The GC oven was programmed as follows: ~140° C. for ~0.5 min., then heated at ~20° C./min. to ~230° C. (hold ~5 min). The injector temperature was kept at ~250° C., and a ~40:1 split ~1 μA injection was used. Helium was used as a carrier gas at a flow rate of about 1.2 ml/min. The analytes were identified by comparison of retention times to individually injected standards. The calibration range for the analytes was ~2 ng/ml to ~200 ng/ml for fatty acids having a chain length of 8 carbons (C8:0) to 16 carbons with one double bond (C16:1) and ~0.5 μg/ml to ~50 μg/ml for fatty acids having a chain length of 18 carbons with no double bond (C18:0) to 18 carbons with two double bonds (C18:2). Spiking and recovery experiments into whole cell culture showed that the extraction method recovered consistently within a range of about 85%-115% of each analyte.

Figure 3:
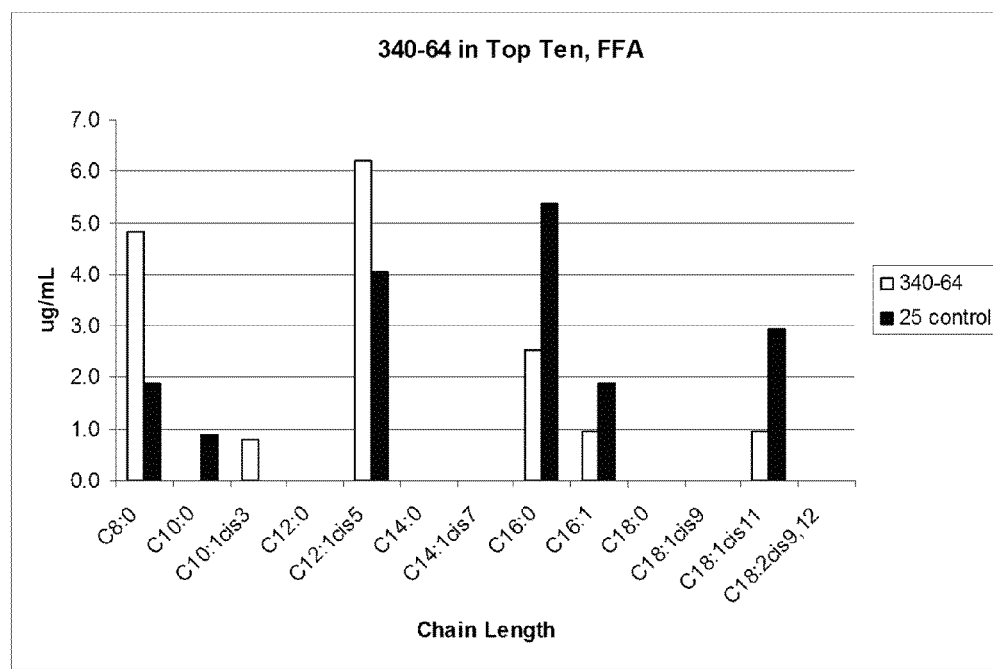
FIG. 3 shows the profile of the free fatty acids (FFA) isolated from the culture of E. coli cells expressing the 340-64 gene (SEQ ID NO:3) compared to a higher plant acyl-ACP thioesterase (25 control).
Figure 4:
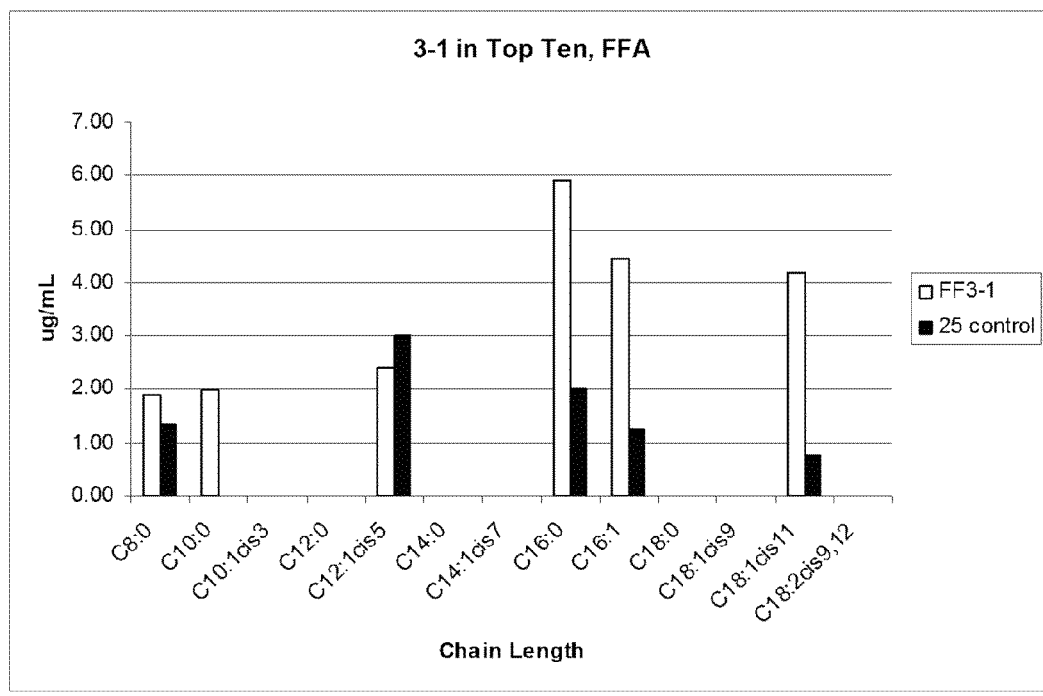
FIG. 4 is a graph of the free fatty acids (FFA) isolated from the culture of E. coli cells expressing the 3-1 gene (SEQ ID NO:4) compared to a control (25 control).
Figure 5:
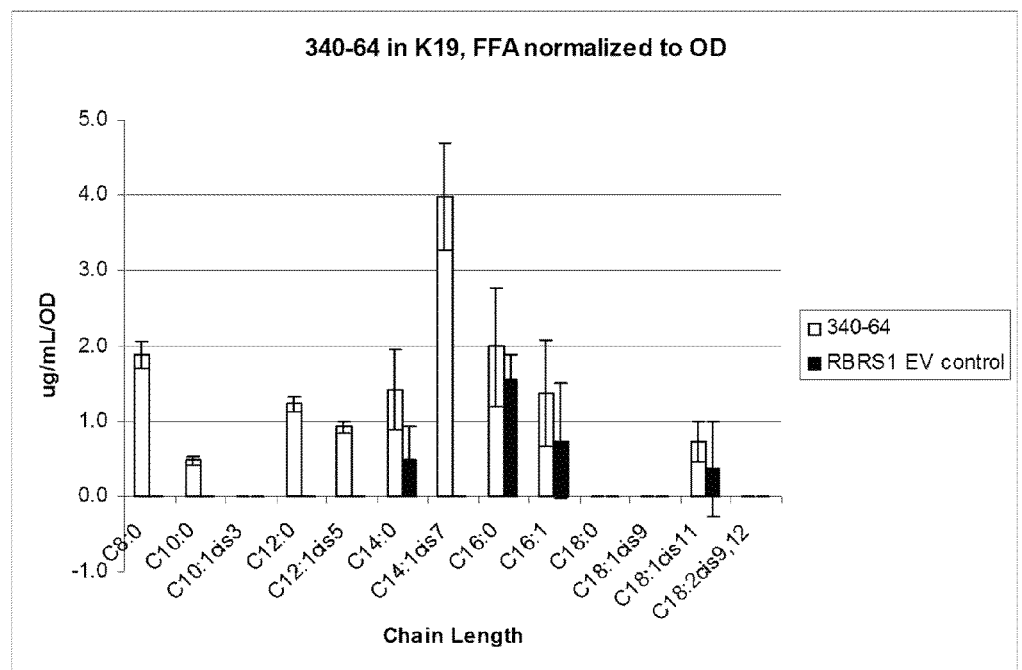
FIG. 5 is a graph of the free fatty acids (FFA) isolated from the culture of E. coli (K19 strain lacking a functional acyl-CoA synthetase) expressing the 340-64 gene (SEQ ID NO:3) compared to a control (RBRS1 empty vector (EV) control). The concentration of free fatty acids (FFA) were normalized to OD of the E. coli cultures.

As shown in FIGS. 3, 4, and 5, expression of the 4-hydroxybenzoyl-CoA thioesterases in E. coli resulted in increased production of free fatty acids in the culture, with the levels of free fatty acids being as high or higher than those produced by E. coli cells expressing a higher plant thioesterase from a Cuphea species (labeled as 25 control). As shown in FIG. 3, expression of the 4-hydroxybenzoyl-CoA thioesterase 340-64 (SEQ ID NO:3) in E. coli led to production of free fatty acids having an acyl chain length of 8, 10, 12, 16, and 18 carbons.

As shown in FIG. 4, the expression of 4-hydroxybenzoyl-CoA thioesterase 3-1 (SEQ ID NO:2) in E. coli also resulted in the production of free fatty acids having acyl chain lengths of 8, 10, 12, 16, and 18 carbons, with the amount of free fatty acids having an acyl chain length of 8, 10, 16, and 18 carbons being higher in the culture containing cells expressing SEQ ID NO:2 compared to a control culture containing cells expressing a Cuphea species higher plant thioesterase (labeled as 25 control).

FIG. 5 shows the level of free fatty acids produced by E. coli K-19 cells (which lack a functional acyl-CoA synthetase, an enzyme on the fatty acid degradation pathway) expressing the 340-644-hydroxybenzoyl thioesterase (SEQ ID NO:3) or an empty vector control (RBRS1 EV control). The amount of free fatty acid was normalized to the O.D. of the K19 cells. Expression of the 340-644-hydroxybenzoyl-CoA thioesterase (SEQ ID NO:3) in K19 cells also increased the level of free fatty acids having acyl chain lengths of 8, 10, 12, 14, 16, and 18 carbons produced by the strain.

Example 4

Acyl-ACP Thioesterase Assay

Because the free fatty acid producing cells were transformed with genes encoding 4-HBTs, not known to generate free fatty acids from acyl-ACP, the enzymes were expressed in E. coli strains for producing the enzymes for use in in vitro assays to determine their thioesterase activity on acyl-ACP substrates.

To this end, E. coli cells were transformed with 340-64 (SEQ ID NO:3), 3-1 (SEQ ID NO:4), or with an empty vector (SEQ ID NO:5) as a control, and expression was induced by adding isopropyl β-D-1-thiogalactopyranoside (IPTG) in the medium of the E. coli culture. The cultures (~10 mls) were inoculated with single colonies and incubated until the OD of the culture reached ~0.6, at which time IPTG was added to a final concentration of ~1 mM, and the cells were allowed to grow overnight. The cells were then pelleted, cell pellets were washed with 1× phosphate buffered saline (PBS) and cell extracts were made by resuspending the pellets in ~0.5 mL lysis buffer xTractor Cell Lysis Buffer (Clontech, Mountain View, Calif.).

The acyl-ACP thioesterase assay was performed as follows: ~5 μL1 of ~10 μM of an *enzymatically synthesized C16* acyl-ACP substrate in a buffer (~100 mM Tris-HCl, pH ~8.0, ~100 mM NaCl) was mixed with ~3 μl of cell extracts from either 3-1 HBT-producing cells, 340-64 HBT-producing cells, or a control extract of E. coli cells not expressing an thioesterase (PE0045). The mixtures were incubated for ~5, ~10, and ~30 mins, and the reactions were stopped by heating up at ~70° C. for ~5 mins. About 10 μl of 2.5× native urea load dye was added to the reaction mixtures. Samples were loaded onto ~20%—2.5M urea native acrylamide gel and run under nondenaturing conditions at ~120 volts for ~60 mins. The gel was stained with Simplyblue™ gel stain (Invitrogen, Carlsbad, Calif.).

Figure 6:
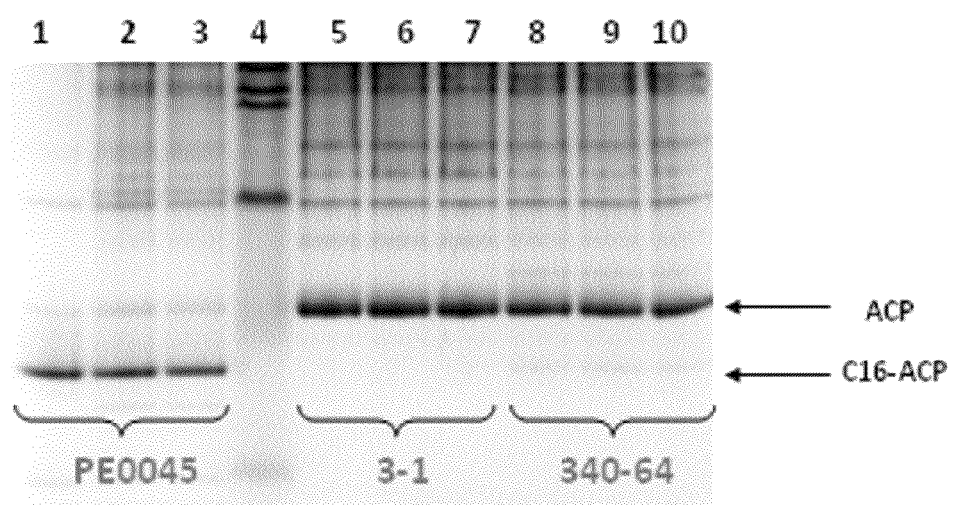
FIG. 6 shows the migration patterns of acyl-ACP substrates in a 20% native acrylamide gel containing 2.5M urea. Acyl-ACP substrates (C16-ACP) were incubated with cell extracts obtained from E. coli expressing different clones (PE0045 (control extract), 3-1 4-HBT (SEQ ID NO:4), or 340-64 4-HBT (SEQ ID NO:3)).

FIG. 6 shows the migration patterns of acyl-ACP substrates in a native acrylamide gel, which were incubated with cell extracts made from E. coli cells expressing different clones, or a control extract (PE0045). Lanes 1-3 show the migration patterns of acyl-ACP substrates (~5 μL1 of ~10 μM) incubated with ~3 μl of xTractor Cell Lysis Buffer (Lane 1) or with a lysate made from the cells containing a control vector (PE0045, ~3 μl), for ~5 mins (Lane 2) or ~10 mins (Lane 3). Lane 4 indicates a protein size marker. Lanes 5-7 (labeled as 3-1) show the migration patterns of acyl-ACP substrates incubated with ~3 μl of extracts (about 5 mg/ml) made from the cells expressing the 3-1 4-hydroxybenzoyl thioesterase (SEQ ID NO:2) for ~5 mins (Lane 5), ~10 mins (Lane 6), and ~30 mins (Lane 7), respectively. Lanes 8-10 show the migration patterns of acyl-ACP substrates incubated with the extracts made from the cells expressing the 340-644-hydroxybenzoyl thioesterase (SEQ ID NO:1) for ~5 mins (Lane 8), ~10 mins (Lane 9), and ~30 mins (Lane 10), respectively.

As shown in FIG. 6, in contrast to a control (acyl-ACP substrate with PE0045 extract), incubation of acyl-ACP substrates with the cell extracts made from the E. coli cells expressing either the 340-64 (SEQ ID NO:1) or 3-1 (SEQ ID NO:2) 4-hydroxybenzoyl-CoA thioesterase led to a dramatic increase in the amount of free ACPs, while decreasing the amount of the ACP substrates conjugated to fatty acids (C16-ACP). These results indicate that both the 3-1 (SEQ ID NO:1) and 340-64 (SEQ ID NO:2) possess a hydrolyzing activity toward the acyl-ACP substrate.

Example 5

Transformation of Cyanobacteria

Plasmids containing the 4-hydroxybenzoyl-CoA thioesterase 340-64 and 3-1 genes are introduced into a cyanobacterial host. *Synechocystis* sp. PCC 6803 cells are transformed essentially according to Zang et al. (*J. Microbiology*, 2007, 45: 241-245, the content of which is incorporated herein by reference in its entirety). Briefly, cells are grown under constant light to an optical density 730 (O.D.$_{730}$) of approximately 0.7 to 0.9 (an OD$_{730}$ of ~0.25 corresponds to ~1×10$^8$ cells/ml) and harvested by centrifugation at ~2,000 g for ~15 mins at room temperature. The cell pellet is resuspended in approximately 0.3 times the growth volume of fresh BG-11 medium and used immediately for transformation. About 1 microgram of plasmid DNA (containing a 4-hydroxybenzoyl-CoA thioesterase gene) is added to ~0.3 ml of cells, gently mixed, and is incubated approximately for ~5 hours with illumination at ~30° C. without agitation. Cells are spread on a filter (Whatmann Nuclepore Polycarbonate Track-Etched membrane, PC ~47 mm, ~0.2 micron) positioned on a ~50 ml BG-11 agar plates and are allowed to recover for about 16 to 24 hours under light, after which the filter is lifted and placed on a fresh BG-11 plate containing spectinomycin (~20 µg/ml) to select for transformants. Resulting colonies are screened further for the presence of the 4-hydroxybenzoyl-CoA thioesterase genes by PCR.

Example 6

Culturing Cyanobacteria

*Synechocystis* cells transformed with the expression constructs comprising the 340-64 (SEQ ID NO:3) and 3-1 (SEQ ID NO:4) genes are cultured phototrophically, in the absence of a reduced carbon source, and using light as an energy source. About ten ml of BG-11 medium containing ~1 mM IPTG in ~20 mL glass vials are inoculated at an OD$_{730nm}$ of ~0.6 and grown for ~6.5 days (~150 rpm) at ~30° C. with constant illumination (~40 µEinsteins m$^{-2}$ sec$^{-1}$). About 0.6 ml of culture is removed for biochemical analysis. The ingredients of the BG-11 medium (ATCC medium: 616 Medium BG-11 for blue-green algae) are as follows:

| | |
|---|---|
| NaNO$_3$ | 1.5 g |
| K$_2$HPO$_4$ | 40 mg |
| MgSO$_4$•7H$_2$O | 75 mg |
| CaCl$_2$•2H$_2$O | 36 mg |
| Citric acid | 6 mg |
| Ferric ammonium citrate | 6 mg |
| EDTA | 1 mg |
| Na$_2$CO$_3$ | 20 mg |
| Trace Metal Mix A5 (see below) | 1 ml |
| Agar (if needed) | 10 g |
| Distilled water | 1 L |

Adjust final pH to ~7.1
Autoclave at ~121° C. for ~15 minutes.

Trace Metal Mix A5 Composition:

| | |
|---|---|
| H$_3$BO$_3$ | 2.86 g |
| MnCl$_2$•4H$_2$O | 1.81 g |
| ZnSO$_4$•7H$_2$O | 0.22 g |
| Na$_2$MoO$_4$•2H$_2$O | 0.39 g |
| CuSO$_4$•5H$_2$O | 79.0 mg |
| Co(NO$_3$)$_2$•6H$_2$O | 49.4 mg |
| Distilled water | 1 L |

Example 7

Analysis of Fatty Acid Samples from Cyanobacteria (*Synechocystis*)

*Synechocystis* fatty acid samples are analyzed on an Agilent model 7890A gas chromatograph equipped with an FID (flame ionization detector) that included a J&W Scientific DB-FFAP capillary column (~15 m length, ~0.25 mm internal diameter, ~0.25 µm film thickness) coupled to an Agilent 5975C mass spectrophotometer. The gas chromatography oven is programmed as follows: ~140° C. for ~0.5 min, then heat at ~20° C./min. to ~230° C. (hold ~5 mins). The injector temperature is kept at ~250° C., and a ~40:1 split ~1.0 µl injection is used. Helium is used as a carrier gas at a flow rate of ~1.2 mL/min. The analytes are identified by comparison of retention times to individually injected standards.

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A microorganism comprising a recombinant nucleic acid molecule encoding a 4-hydroxybenzoyl-coenzyme A (CoA) thioesterase, wherein the 4-hydroxybenzoyl-CoA thioesterase hydrolyzes acyl-acyl carrier protein (acyl-ACP), and wherein expression of the 4-hydroxybenzoyl-CoA thioesterase in the microorganism results in production of at least one free fatty acid and/or fatty acid derivative, and further wherein at least 30 wt % of the free fatty acids produced by the microorganism are free fatty acids having an acyl chain length of 12 carbons, 14 carbons, 16 carbons, or any mixture thereof.

2. The microorganism of claim 1, wherein the at least one-fatty acid derivative comprises at least one fatty aldehyde, at least one fatty alcohol, at least one wax ester, at least one alkane, at least one alkene, or a combination thereof.

3. The microorganism of claim 2, wherein the at least one-fatty acid derivative has a total number of carbons from 7 to 36.

4. The microorganism of claim 1, wherein the microorganism is capable of producing at least one free fatty acid having an acyl chain length from 8 to 24 carbons.

5. The microorganism of claim 1, wherein the 4-hydroxybenzoyl-CoA thioesterase has at least 85% amino acid sequence identity to SEQ ID NO:1 or SEQ ID NO:2.

6. The microorganism of claim 1, wherein the microorganism is a photosynthetic microorganism.

7. The photosynthetic microorganism of claim 6, wherein the photosynthetic microorganism is a microalga of a genus selected from the group consisting of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, and *Volvox*.

8. The photosynthetic microorganism of claim 6, wherein the photosynthetic microorganism is a cyanobacterium.

9. The photosynthetic microorganism of claim 8, wherein the photosynthetic microorganism is a cyanobacterium of a genus selected from the group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, and *Xenococcus*.

10. The microorganism of claim 5, wherein the nucleic acid molecule encoding the 4-hydroxybenzoyl-CoA thioesterase comprises amino acid sequence SEQ ID NO: 1 or SEQ ID NO:2.

11. The microorganism of claim 1, wherein the microorganism further comprises at least one additional nucleic acid molecule encoding at least one additional polypeptide, wherein expression of the additional nucleic acid molecule in the microorganism enhances production of a free fatty acid and/or fatty acid derivative.

12. The microorganism of claim 11, wherein the at least one additional nucleic acid molecule encodes acetyl-CoA carboxylase or β-ketoacyl synthase (KAS).

13. The microorganism of claim 1, wherein the microorganism has attenuated expression of at least one gene encoding a protein selected from the group consisting of acyl-ACP synthase, acyl-CoA dehydrogenase, glycerol-3-phosphate dehydrogenase, acetaldehyde-CoA dehydrogenase, pyruvate dehydrogenase, acetate kinase, and combinations thereof.

14. A method for producing a free fatty acid or a fatty acid derivative in a culture, the method comprising culturing the microorganism of claim 1 in growth media.

15. The method of claim 14, wherein at least a portion of the free fatty acid and/or fatty acid derivative is secreted into the growth media.

16. The method of claim 14, wherein the 4-hydroxybenzoyl-CoA thioesterase has at least 85% amino acid sequence identity to SEQ ID NO:1 or SEQ ID NO:2.

17. The method of claim 14, wherein the microorganism is a photosynthetic microorganism.

18. The microorganism of claim 1, wherein the 4-hydroxybenzoyl-CoA thioesterase belongs to Pfam PF03061.

19. The method of claim 14, wherein the 4-hydroxybenzoyl-CoA thioesterase belongs to Pfam PF03061.

* * * * *